(12) United States Patent
Zeng et al.

(10) Patent No.: US 7,190,452 B2
(45) Date of Patent: Mar. 13, 2007

(54) IMAGING SYSTEMS FOR FLUORESCENCE AND REFLECTANCE IMAGING AND SPECTROSCOPY AND FOR CONTEMPORANEOUS MEASUREMENTS OF ELECTROMAGNETIC RADIATION WITH MULTIPLE MEASURING DEVICES

(75) Inventors: Haishan Zeng, Vancouver (CA); Stephen Lam, Vancouver (CA); Branko Mihael Palcic, Vancouver (CA)

(73) Assignee: Perceptronix Medical, Inc., Vancouver (CA)

( * ) Notice: Subject to any disclaimer, the term of this patent is extended or adjusted under 35 U.S.C. 154(b) by 0 days.

(21) Appl. No.: 11/058,045

(22) Filed: Feb. 14, 2005

(65) Prior Publication Data

US 2005/0203423 A1  Sep. 15, 2005

Related U.S. Application Data

(60) Division of application No. 10/028,568, filed on Dec. 19, 2001, now Pat. No. 6,898,458, which is a continuation-in-part of application No. 09/741,731, filed on Dec. 19, 2000, now Pat. No. 6,826,424.

(51) Int. Cl.
*G01J 3/28* (2006.01)
(52) U.S. Cl. .................................................. 356/326
(58) Field of Classification Search ............ 356/72–73, 356/326
See application file for complete search history.

(56) References Cited

U.S. PATENT DOCUMENTS

| | | | |
|---|---|---|---|
| 4,540,278 A * | 9/1985 | Phillips | 355/55 |
| 4,556,057 A | 12/1985 | Hiruma et al. | 128/303.1 |
| 4,768,513 A | 9/1988 | Suzuki | 128/634 |
| 4,782,819 A | 11/1988 | Adair | 128/6 |
| 4,786,813 A | 11/1988 | Svanberg et al. | 250/461.1 |
| 4,820,046 A * | 4/1989 | Sohma et al. | 356/328 |
| 4,930,516 A | 6/1990 | Alfano et al. | 128/665 |
| 5,042,494 A | 8/1991 | Alfano | 128/665 |
| 5,092,331 A | 3/1992 | Nakamura et al. | 128/634 |
| 5,131,398 A | 7/1992 | Alfano et al. | 128/665 |
| 5,255,087 A | 10/1993 | Nakamura et al. | 358/98 |
| 5,293,872 A | 3/1994 | Alfano et al. | 128/664 |
| 5,348,018 A | 9/1994 | Alfano et al. | 128/665 |
| 5,413,108 A | 5/1995 | Alfano | 128/665 |
| 5,507,287 A | 4/1996 | Palcic et al. | 128/633 |
| 5,590,660 A | 1/1997 | MacAulay et al. | 128/664 |
| 5,647,368 A | 7/1997 | Zeng et al. | 128/665 |

(Continued)

FOREIGN PATENT DOCUMENTS

AU  2474899 A1  8/1999

(Continued)

OTHER PUBLICATIONS

International Search Report, PCT/CA01/01824, Feb. 28, 2003.

(Continued)

*Primary Examiner*—Gregory J. Toatley, Jr.
*Assistant Examiner*—Kara Geisel
(74) *Attorney, Agent, or Firm*—Graybeal Jackson Haley LLP

(57) ABSTRACT

Optical systems that provide for simultaneous images and spectra from an object, such as a tissue sample, an industrial object such as a computer chip, or any other object that can be viewed with an optical system such as a microscope, endoscope, telescope or camera. In some embodiments, the systems provide multiple images corresponding to various desired wavelength ranges within an original image of the object, as well as, if desired, directional pointer(s) that can provide both an identification of the precise location from which a spectrum is being obtained, as well as enhancing the ability to point the device.

6 Claims, 16 Drawing Sheets

U.S. PATENT DOCUMENTS

| | | | |
|---|---|---|---|
| 5,675,378 A | 10/1997 | Takasugi et al. | 348/65 |
| 5,701,903 A | 12/1997 | Sano et al. | 128/665 |
| 5,749,830 A | 5/1998 | Kaneko et al. | 600/160 |
| 5,769,792 A | 6/1998 | Palcic et al. | 600/477 |
| 5,772,580 A | 6/1998 | Utsui et al. | 600/160 |
| 5,827,190 A | 10/1998 | Palcic et al. | 600/476 |
| 5,879,284 A | 3/1999 | Tsujita | 600/109 |
| 5,891,016 A | 4/1999 | Utsui et al. | 600/181 |
| 5,900,942 A | 5/1999 | Spiering | 356/400 |
| 5,971,918 A | 10/1999 | Zanger | 600/160 |
| 5,982,493 A | 11/1999 | Lehnen et al. | 356/375 |
| 5,984,861 A | 11/1999 | Crowley | 600/175 |
| 5,999,844 A | 12/1999 | Gombrich et al. | 600/476 |
| 6,008,889 A | 12/1999 | Zeng et al. | 356/73 |
| 6,021,344 A | 2/2000 | Lui et al. | 600/476 |
| 6,024,920 A * | 2/2000 | Cunanan | 356/73 |
| 6,028,622 A | 2/2000 | Suzuki | 348/65 |
| 6,083,158 A | 7/2000 | Bearman et al. | 600/323 |
| 6,128,085 A * | 10/2000 | Buermann et al. | 356/369 |
| 6,148,227 A | 11/2000 | Wagnieres et al. | 600/476 |
| 6,161,035 A | 12/2000 | Furusawa | 600/476 |
| 6,212,425 B1 | 4/2001 | Irion et al. | 600/476 |
| 6,214,033 B1 | 4/2001 | Ii et al. | 607/89 |
| 2005/0164608 A2 * | 7/2005 | Finarov | 356/73 |

FOREIGN PATENT DOCUMENTS

| | | |
|---|---|---|
| DE | 19646176 A1 | 5/1997 |
| DE | 19819516 A1 | 11/1998 |
| DE | 19842153 A1 | 3/2000 |
| EP | 0385608 | 9/1990 |
| EP | 1058101 A2 | 12/2000 |
| GB | 2254417 | 10/1992 |
| JP | 62217216 A2 | 9/1987 |
| JP | 63201620 A2 | 8/1988 |
| JP | 1136629 A2 | 5/1989 |
| JP | 1136630 A2 | 5/1989 |
| JP | 2096109 A2 | 4/1990 |
| JP | 3097439 A2 | 4/1991 |
| JP | 3097440 A2 | 4/1991 |
| JP | 3097441 A2 | 4/1991 |
| JP | 7155285 A2 | 6/1995 |
| JP | 7155290 A2 | 6/1995 |
| JP | 7155291 A2 | 6/1995 |
| JP | 7250812 A2 | 10/1995 |
| JP | 8000557 A2 | 1/1996 |
| JP | 8140928 A2 | 6/1996 |
| JP | 8140929 A2 | 6/1996 |
| JP | 8224208 A2 | 9/1996 |
| JP | 8224209 A2 | 9/1996 |
| JP | 8224210 A2 | 9/1996 |
| JP | 8224240 A2 | 9/1996 |
| JP | 09131305 A2 | 5/1997 |
| JP | 9131305 A2 | 5/1997 |
| JP | 9131306 A2 | 5/1997 |
| JP | 9131307 A2 | 5/1997 |
| JP | 9131308 A2 | 5/1997 |
| JP | 9131349 A2 | 5/1997 |
| JP | 10014857 A2 | 1/1998 |
| JP | 10014869 A2 | 1/1998 |
| JP | 10024010 A2 | 1/1998 |
| JP | 10057300 A2 | 3/1998 |
| JP | 10127563 A2 | 5/1998 |
| JP | 10151104 A2 | 6/1998 |
| JP | 10165365 A2 | 6/1998 |
| JP | 10201707 | 8/1998 |
| JP | 10201707 A2 | 8/1998 |
| JP | 10225426 A2 | 8/1998 |
| JP | 10295632 A2 | 11/1998 |
| JP | 10328129 A2 | 12/1998 |
| JP | 11113839 A2 | 4/1999 |
| JP | 11223726 A2 | 8/1999 |
| JP | 11244220 A2 | 9/1999 |
| WO | WO 99/16344 | 4/1999 |
| WO | WO 99/37204 | 7/1999 |
| WO | WO 99/39626 | 8/1999 |
| WO | WO 99/53832 | 10/1999 |
| WO | WO 00/21576 | 4/2000 |

OTHER PUBLICATIONS

Jianan Qu, Calum MacAulay, Stephen Lam, Branko Palcic, Haishan Zeng, "Fluorescence in normal and carcinoma bronchial tissue", SPIE 2134A, 236-246 (1994).

Jianan Qu, Calum MacAulay, Stephen Lam and Branko Palcic. "Laser-induced Fluorescence Spectroscopy at Endoscopy", SPIE 2133, 162-169 (1994).

Stephen Lam, Calum MacAulay, Jean LeRiche, Norihiko Ikeda and Branko Palcic, "Fluorescence imaging of early lung cancer", SPIE 2324, 2-7 (1994).

C. MacAulay, S. Lam, J. Qu, C. Man, M. Harries and B. Palcic, "Optical properties of normal malignant tissues in the nasopharynx and larynx", SPIE 2395, 153-157 (1995).

Jianan Qu, Calum MacAulay, Stephen Lam and Branko Palcic, "Mechanisms of ratio fluorescence imaging of diseased tissue," SPIE 2387, 71-79 (1995).

Jianan Qu, Calum MacAulay, Stephen Lam and Branko Palcic, "Laser-induced fluorescence spectroscopy at endoscopy: tissue optics, Monte Carlo modeling, and in vivo measurements", Optical Engineering 34:11, 3334-3343 (1995).

S. Lam and A.E. Profio, "Fluorescence Tumor Detection", Minimally Invasive Techniques in Thoratic Medicine and Surgery, ed. Martin R. Hetzel, Chapman & Hall, London, 179-191 (1995).

Stephen Lam and Heinrich D. Becker. "Future Diagnostic Procedures", Thoracic Endoscopy 6:2, 363-380 (1996).

H. Zeng, A. Weiss, N. MacKinnon, R. Cline, C. MacAulay, "In vivo Fluorescence Spectroscopy of the Gastrointestinal Tract under Multiple Wavelength Excitation", SPIE 2926, 4-8 (1996).

Wolfgang Lohmann, Rainer M. Bohle, Thomas Dreyer, Sabine Haas, Heike Wallenfels, Konrad Schwemmle, Wolf B. Schill, "Breast Cancer: In Vitro Measurements of Native Fluorescence", SPIE 2926, 9-11(1996).

Naser Awadh, Calum MacAulay and Stephen Lam, "Detection and Treatment of Superficial Lung Cancer by Using delta Aminolevulinic Acid: A Preliminary Report", J. Bronch. 4:1, 13-17 (1997).

Stephen Lam and Calum E. MacAulay, "Endoscopic Localization of Preneoplastic Lung Lesions", Clinical and Biological Basis of Lung Cancer Prevention, ed. Y. Martinet et al., Birkhauser Verlag Basel, Switzerland, 231-237 (1998).

Haishan Zeng, Alan Weiss, Richard Cline and Calum E. MacAulay, "Real—time endoscopic fluorescence imaging for early cancer detection in the gastrointestinal tract", Bioimaging 6, 151-165 (1998).

Stephen Lam and Calum MacAulay, "Endoscopic Detection of Preneoplastic Lesions", Lung Tumors: Fundamental Biology & Clinical Management, ed. Brambilla, Marcel Dekker, 473-480 (1998).

Haishan Zeng, Calum E. MacAulay, Stephen Lam and Branko Palcic, "Light induced fluorescence endoscopy (LIFE) imaging system for early cancer detection", SPIE 3863, 275-282 (1999).

Haishan Zeng, Alan Weiss and Calum MacAulay, "System for Fast Measurements of in Vivo Fluorescence Spectra of the Gastrointesinal Tract at Multiple Excitation Wavelengths", Applied Optics 38, 7157-7158 (1999).

Circon advertisement "Selected laparoscopic Products" http://www.circoncorp.com/products/lapr/p-lapr-selected.html Jul. 5, 2001.

* cited by examiner

IMAGING SYSTEMS FOR FLUORESCENCE AND REFLECTANCE IMAGING AND SPECTROSCOPY AND FOR CONTEMPORANEOUS MEASUREMENTS OF ELECTROMAGNETIC RADIATION WITH MULTIPLE MEASURING DEVICES

CROSS-REFERENCE TO RELATED APPLICATIONS

The present application is a Divisional of U.S. patent application Ser. No. 10/028,568, filed on Dec. 19, 2001 now U.S. Pat. No. 6,898,458, which is a Continuation-in-part of U.S. patent application Ser. No. 09/741,731, filed Dec. 19, 2000, now U.S. Pat. No. 6,826,424, issued on Nov. 30, 2004.

FIELD OF THE INVENTION

The present invention relates to electromagnetic radiation measuring devices, and more particularly to methods and apparatus for facilitating contemporaneous measurements of electromagnetic radiation with multiple measuring devices, for producing illuminating radiation for fluorescence and reflectance imaging, for performing both fluorescence and reflectance imaging using the same detectors in an imaging device, for producing a high diagnostic sensitivity image while achieving high diagnostic specificity with spectroscopy, for detecting tissue oxygenation, and for producing a fluorescence image of tissue.

BACKGROUND OF THE INVENTION

Many applications involve taking more than one type of measurement of electromagnetic radiation. For example, some medical imaging applications involve insertion of an endoscope into a cavity or incision in a subject such as a human patient. A flexible endoscope, for example, may include an optics channel through which a first optical fiber bundle conveys illumination light for illuminating internal tissues of the patient, and through which a second, coherent optical fiber bundle conveys light reflected or fluorescently emitted by the internal tissues back up through the endoscope to a measuring device such as a charge-coupled device (CCD) camera. A resulting image of the internal tissues produced by the camera may then be displayed on a monitor for visual inspection by a surgeon or physician, who may be able to identify suspected abnormal or diseased tissue from the displayed image.

Once suspected abnormal tissues have been identified by such visual inspection, it is then desirable to perform additional analysis on the tissue to confirm with greater specificity or accuracy whether it is in fact diseased. For this purpose, spectroscopy is sometimes performed. One existing spectroscopic analysis method involves the insertion of an optical fiber probe through a biopsy channel of the endoscope, which is normally used for insertion through the endoscope of medical tools such as those used for tissue sampling or therapeutic interventions, for example. The presence of this optical fiber probe in the biopsy channel may make it difficult or impossible to insert other tools into the biopsy channel, rendering the biopsy channel unsuitable for its intended purpose. In addition, this procedure may pose inconvenience for the surgeon or physician, who may have to remove medical tools from the biopsy channel in order to insert the optical fiber probe, then remove the probe in order to reinsert the tools when the spectral measurement is completed. Moreover, when the optical fiber probe is inserted through the biopsy channel, the probe typically comes into physical contact with the tissue in order to perform a measurement. Such contact tends to press blood away from the tissue to varying degrees, depending on the amount of pressure applied, which may result in different observed spectra, thereby introducing a source of measurement error.

One existing endoscopic system employs a beam splitter for directing a percentage of radiation received from the tissue for receipt by a spectroscopy device, while allowing the remainder of such radiation to pass through the beam splitter for receipt by a camera. However, it will be appreciated that beam splitters of this nature reduce the intensity of light received across the entire area of the camera. Generally, only a relatively low amount of light from the analyzed tissues enters the endoscope, due to the small circumference of the endoscope, the limited ability to increase the intensity of the illuminating light without causing thermal damage or photobleaching in the tissue, and due to the relatively low intensity of light fluorescently emitted or reflected by the tissue. Accordingly, the CCD camera is already "light hungry". The use of such beam splitters aggravates this problem, resulting in an even darker CCD image, which may necessitate the use of expensive signal amplification devices.

Alternatively, in another existing endoscopic system, a mirror is employed for a somewhat different purpose. The mirror is inserted into the optical path of the light beam from the endoscope so as to reflect the entire beam to a first camera for white light reflectance imaging, and is removed from the optical path so as to allow the entire beam to be received at a second camera for fluorescence imaging. However, this method does not allow for simultaneous measurements by the first and second cameras, which increases the chance that the endoscope or the subject might move between alternate images. This difficulty may not be serious for use in switching between white light reflectance and fluorescence images, however, this method would not be desirable for combined imaging and spectroscopy measurements, as it fails to ensure that the spectroscopy measurement is of the same tissue region that appeared to be of interest in the camera image, which may lead to unreliable spectroscopy results.

Accordingly, there is a need for a more convenient way of performing contemporaneous measurements with multiple measuring devices, such as an imaging device and a spectroscopy device for example, without significantly compromising endoscopic imaging quality or reliability of the spectroscopy results.

Additionally, existing endoscopic systems have failed to utilize the full potential of combined imaging and spectroscopy. In particular, for systems involving multi-spectral-channel imaging devices, such as white light reflectance RGB color CCD cameras and dual channel fluorescence imaging cameras for example, the ability to increase the diagnostic sensitivity of such devices by adjusting the gain relationships between different imaging channels is constrained by conventional wisdom, which indicates that any increase in the diagnostic sensitivity of the imaging device by gain relationship adjustment results in a corresponding decrease in specificity of diagnosis. In other words, increasing the diagnostic sensitivity of a dual channel fluorescence imaging device, for example, will produce more "false positive" diagnoses, as a result of tissues that appear from the image alone to be diseased or malignant when in fact they are benign or even normal. The desire to avoid such erroneous diagnoses therefore places limitations on the ability to adjust the diagnostic sensitivity of the imaging device.

Thus, there is a need for a way to produce images of higher diagnostic sensitivity without unduly reducing the specificity or accuracy of diagnoses.

In addition, an endoscopic imaging system preferably involves both white light reflectance color imaging to produce a normal view in which the appearance of an internal organ is familiar to the surgeon or physician, and fluorescence imaging for better diagnostic accuracy. For white light reflectance imaging, an image of the tissue of interest is taken while the tissue is being irradiated with white light. For fluorescence imaging, the tissue is irradiated with excitation light, typically short wavelength light, which may range from blue to ultraviolet depending on the application. In order to avoid the necessity of injecting the tissue with drugs containing fluorescent substances, the trend has been toward autofluorescence imaging. When tissues are irradiated with short wavelength excitation radiation, the tissues tend to emit fluorescence light which typically ranges from 450 to 750 nm and peaks at green wavelengths from 510 to 530 nm, for example. It has been found that abnormal tissues such as diseased or cancerous tissues tend to emit significantly lower intensities of such autofluorescence light at green wavelengths than normal tissues. Abnormal or suspicious tissues therefore tend to appear darker in a corresponding fluorescence image of the tissues at green wavelengths. Thus, different illumination spectra are required for reflectance and fluorescence imaging, namely, a white light or other illumination spectrum for reflectance imaging and at least a short-wavelength excitation spectrum for fluorescence imaging.

Most existing systems for reflectance and fluorescence imaging are either inconvenient to switch between reflectance and fluorescence imaging, or fail to adequately correct the fluorescence image to compensate for geometric factors, or both.

More particularly, to switch between white light reflectance and fluorescence imaging, many systems require a user of the system, such as a surgeon or physician, to manually disconnect a first light source and first RGB CCD camera used for white light reflectance imaging from the endoscope, and to connect a second separate light source and second fluorescence camera to the endoscope for fluorescence imaging. Such manual disconnection and connection of light sources and cameras are time-consuming and inconvenient to the user, and increase the duration and discomfort to the patient being examined.

With respect to correction of the fluorescence image to compensate for geometric factors, it has been found that using only a single short-wavelength illumination waveband is disadvantageous for fluorescence imaging. Although tissue abnormality or disease may cause a given point in the fluorescence image to appear dark, alternatively, normal tissue may also appear dark if it is simply further away from the tip of the endoscope than other points in the tissue, or alternatively normal tissue may appear dark due to partial obstruction or other geometrical factors, such as curved tissue surfaces, folds, polyps, or the angle of the endoscope relative to the tissue surface, for example. Thus, it is not possible to determine from a green fluorescence image alone whether or not a particular point in the tissue appears dark because it is abnormal, or whether it appears dark merely because of its distance or geometrical positioning relative to the endoscope tip.

Some systems have attempted to address the latter difficulty by additionally measuring autofluorescence at red wavelengths, as autofluorescence intensities of normal and abnormal tissues are more similar at red and longer wavelengths than they are at green wavelengths. The resulting red autofluorescence image may be used to correct the green autofluorescence image for the geometry of the tissue. For example, if the red autofluorescence image is displayed as a red image on a display screen, and the green autofluorescence image is superposed over the red image, then if a given point in the tissue is normal tissue but appears dark in the green image due to geometric factors, then that point will also appear dark in the red image, and will therefore appear dark in the superposition of the two images. However, if a given point in the tissue appears dark in the green image because it is abnormal or diseased, then that point will probably appear bright in the red image, and will therefore appear as a red spot in the superposed image. Unfortunately, however, red autofluorescence occurs at much lower intensities than green autofluorescence, and accordingly, the red image suffers from a low signal-to-noise ratio. In addition, although red autofluorescence emission intensities are similar for normal and abnormal tissues, there is still some difference between the two. Thus, this method tends to suffer from significant measurement error.

One existing system, recently designed in part by some of the inventors of the present invention, has partly addressed both of the above difficulties. An arc lamp directs input radiation onto a cold mirror, which reflects near ultraviolet and visible light to an optical system, while transmitting over 90% of infrared (IR) radiation away from the optical system to prevent heat damage of the optical system due to continuous IR irradiation. The radiation from the cold mirror passes through a long wave pass (LP) filter which transmits visible light through the optical system while attenuating ultraviolet wavelengths. The visible light from the LP filter is then directed through one of a plurality of different filters on a rotary filter wheel. One of the filters generates uniform white light for normal reflectance imaging of the tissue. Another of the filters is a notch-band filter for fluorescence imaging. This way, one light source provides illumination for both white light reflectance imaging and fluorescence imaging, eliminating the need to switch the endoscope between two light sources.

The notch-band filter transmits blue wavelengths shorter than 450 nm, and also transmits red wavelengths longer than 590 nm, which also include some IR wavelengths due to the imperfection of the cold mirror. The notch-band filter attenuates green wavelengths between 450 nm and 590 nm, in order to prevent reflection by the tissue of such wavelengths which would interfere with the ability to measure autofluorescence emission by the tissue at these wavelengths. The blue wavelengths excite the tissue resulting in autofluorescence emission by the tissue at the green wavelengths, which may then be measured to produce a green autofluorescence image. The red wavelengths are used to illuminate the tissue to produce a separate red reflectance image of the tissue, simultaneously with the production of the green autofluorescence image. The red reflectance image has much greater intensity than a red autofluorescence image, and therefore has an improved signal-to-noise ratio, thus reducing errors. The red and green images are then superposed on a display, to provide an improved correction for geometric factors.

However, the single optical system light source employed in the above method tends to be inflexible in at least some respects. For example, because both the blue light used for excitation and the red light used for correction must pass through a single notch-band filter, the selection of wavelengths to be used for excitation and correction is limited by manufacturing constraints on such filters. For example, it may be desirable to use NIR radiation rather than red radiation to provide the reflectance image for correction purposes, as diseased and normal tissues exhibit even more similar reflectance intensities at some NIR wavelength bands than at red wavelengths. However, it may not be feasible to design a single filter with a wider notch-band, to attenuate wavelengths from 450 to 750 nm, for example. Simply eliminating the cold mirror and transmitting all infrared wavelengths through the optical system would be undesirable, as it may cause heat damage to other filters on the rotary filter wheel such as the reflectance imaging filter for example, and may also cause such damage to lenses and other components in the optical system.

Thus, in addition to the deficiencies in existing endoscopic imaging and spectroscopy systems referred to above, there is also a need for an improved illumination source suitable for both reflectance and fluorescence imaging.

Similarly, existing cameras for reflectance and fluorescence imaging are often large and heavy due to the significant number of moving parts they contain in order to switch between reflectance and fluorescence imaging. Such cameras are therefore difficult for a physician or surgeon to wield. Thus, there is also a need for an improved, more light-weight and compact camera capable of performing both reflectance imaging and fluorescence imaging without unduly increasing the size and weight of the camera.

Finally, it is known that cancerous tissues exhibit hypoxia, which is caused by increased oxygen consumption due to rapid growth of cancerous cells. However, other unrelated chromophores tend to overwhelm and obscure the effects of hypoxia at visible imaging wavelengths, with the result that conventional endoscopic imaging systems have typically been unable to detect tissue oxygenation status. Accordingly, there is a need for a way to take advantage of this property of cancerous tissues to improve diagnostic accuracy in endoscopic imaging systems.

SUMMARY OF THE INVENTION

The present invention provides these and other needs by providing optical systems that provide for simultaneous images and spectra from an object, such as a tissue sample, an industrial object such as a computer chip, or any other object that can be viewed with an optical system such as a microscope, endoscope, telescope or camera. In some embodiments, the present invention further provides systems that provide multiple images corresponding to various desired wavelength ranges within an original image of the object, as well as, if desired, directional pointer(s) that can provide both an identification of the precise location from which a spectrum is being obtained, as well as enhancing the ability to point the device.

In one aspect, the invention provides a method and apparatus for facilitating contemporaneous measurements of electromagnetic radiation with multiple measuring devices. The method involves causing first and second adjacent groups of rays of an electromagnetic radiation beam to be directed for receipt by first and second measuring devices respectively. The apparatus includes a beam-directing device locatable to cause the first and second adjacent groups of rays to be directed in this manner.

Thus, a first group of rays may be directed for receipt by a spectrometer, for example, while the second, adjacent group of rays may be directed to an imaging device such as a camera. In such a case, none of the second group of rays would be directed to the spectrometer, and accordingly, the second group of rays may arrive essentially undiminished at the camera, resulting in a brighter image than would be possible using a semi-transparent beam splitter, for example. In many applications, this may eliminate the need for expensive signal amplification devices, such as image intensifiers, which introduce noise, and which also increase the cost and weight of the imaging device. In addition, the image produced by such an imaging device in response to the second group of rays will have a black spot corresponding to the original paths of the first group of rays which have been directed to the other measuring device, e.g. the spectrometer. Thus, by observing the location of the black spot in the image produced in response to the second group of rays, an observer such as a surgeon or physician for example, will immediately know the precise point that is being sampled by the spectrometer and will therefore know whether the spectrometer is measuring a point in the desired area of interest, such as a suspicious looking area in the image produced in response to the second group of rays. In addition, this method may be effectively used to allow for both the first and second measuring devices, such as a camera and a spectrometer for example, to simultaneously produce measurements from a single electromagnetic radiation beam, without the need to produce a second separate beam, using a semitransparent beam splitter or an optical fiber passing through the biopsy channel of an endoscope, for example. Also, more accurate spectra may be obtained without a fiber probe touching the tissue.

Preferably, causing the adjacent groups of rays to be directed in the above manner involves directing the first group of rays for receipt by the first measuring device. The beam-directing device may be locatable to achieve this.

More particularly, directing the first group of rays preferably involves locating a reflective surface in the electromagnetic radiation beam to reflect the first group of rays from the beam, while permitting the second group of rays to bypass the reflective surface. The beam-directing device may include a reflective surface locatable in the beam for this purpose.

The method may further involve receiving the electromagnetic radiation beam from an imaging channel of an endoscope. For example, the electromagnetic radiation beam may be received at an input port of a housing. In such an embodiment, causing the first and second adjacent group of rays to be directed to the first and second measuring devices may involve directing the first group of rays toward a spectrometer port of the housing, and directing the second group of rays toward an imaging device. Directing the first group of rays may involve reflecting the first group of rays within the housing, and may additionally or alternatively involve focusing the first group of rays onto the spectrometer port. The second group of rays may be received at a charge-coupled device (CCD) within the housing.

Similarly, the apparatus may include a housing in which the beam-directing device is locatable. The housing may have an input port configured to receive the electromagnetic radiation beam from the imaging channel of the endoscope and to direct the beam to the beam-directing device.

In addition to the input port, the housing may have a first measurement port, such as the spectrometer port for example, for providing the first group of rays to the first measuring device, in which case the beam-directing device may be locatable in the housing to receive the electromagnetic radiation beam from the input port and to direct the first group of rays to the first measurement port.

The apparatus may include a lens locatable within the housing to focus the first group of rays onto the first measurement port.

The method may further involve receiving the first and second adjacent groups of rays at the measuring devices. For example, the first group of rays may be received at a spectroscopy device and the second group of rays may be received at an imaging device. In this regard, the apparatus may include at least one of the first and second measuring devices, such as an imaging device for example, or a spectroscopy device, for example.

The method may also involve directing respective wavelength ranges of incident radiation in the second group of rays onto respective corresponding detector areas in one of the measuring devices. For example, this may involve directing four wavelength ranges of the incident radiation onto four respective corresponding detector areas in the one of the measuring devices. In this regard, the apparatus may further include a radiation direction system configured to direct the respective wavelength ranges of incident radiation in the second group of rays onto the respective corresponding detector areas of the imaging device.

In accordance with another aspect of the invention, there is provided a method and apparatus for producing a high diagnostic sensitivity image while achieving high diagnostic specificity with spectroscopy. The method involves selectively adjusting a gain of an imaging device in at least one wavelength range relative to a gain of the imaging device in at least one other wavelength range to produce an improved image of an object, and measuring a spectrum of radiation from a point in an area of the object appearing in the improved image. The apparatus includes at least two detectors for receiving radiation in respective wavelength ranges, at least one of the detectors having a selectively adjustable gain adjustable to produce an improved image of an object in response to input radiation. The apparatus further includes a housing containing the detectors and having a first measurement port for providing at least some of the input radiation to a spectrometer to facilitate measurement of a spectrum of the input radiation from a point in an area of the object appearing in the improved image. The apparatus may also include a processor circuit configured to selectively adjust the gain in one of the detectors relative to the gain of at least one other of the detectors to produce the improved image of the object.

Thus, the gains of the imaging device may be selectively adjusted to produce an improved image. In this regard, the gains of the imaging device may be adjusted to different relative levels than those used in existing systems, if desired. The resulting higher diagnostic sensitivity may be achieved without loss of specificity of diagnosis, due to the use of spectroscopy to reduce the occurrence of false positive diagnoses.

Selectively adjusting gain may involve adjusting at least one of a red wavelength range gain and a green wavelength range gain to produce a desired red-to-green signal ratio for fluorescence imaging of the object. The processor circuit may be configured to perform such selective adjustment. For example, using the combined fluorescence and red reflectance method described earlier herein to normalize the fluorescence image, the red-to-green signal ratio may be increased to higher levels than previously used, to provide greater red intensity of suspicious tissue areas in the superposition of the green fluorescence and red reflectance images, while using spectroscopy to reduce the occurrence of false positive diagnoses which would otherwise have resulted from increasing this red-to-green signal ratio.

Similarly, selectively adjusting gain may involve adjusting at least one of red, green and blue wavelength range gains to produce a desired color balance for white light reflectance imaging of the object. The processor circuit may be configured to selectively adjust such gains.

Preferably, selectively adjusting gain involves setting the gains in the at least one wavelength range and in the at least one other wavelength range to a first set of gain levels to enhance display of abnormal areas of the object in a fluorescence image of the object, and further involves setting the gains to a second set of gain levels to enhance the display of the abnormal areas of the object in a reflectance image of the object. The processor circuit may be configured to set such gain levels.

Preferably, the detectors include four detectors for receiving radiation in four respective wavelength ranges, such as a blue range, a green range, a red to near infrared range, and a second near infrared range, for example. The apparatus may further include a radiation direction system within the housing, configured to direct the four respective wavelength ranges of incident radiation received from the object onto the four respective corresponding detectors.

For example, the radiation direction system may include a first partially reflecting device, a second partially reflecting device, a third partially reflecting device and a reflector. The first partially reflecting device is locatable to reflect the first wavelength range of the incident radiation to the first detector and to transmit other wavelengths. The second partially reflecting device is locatable to reflect the second wavelength range of radiation transmitted by the first partially reflecting device to the second detector and to transmit other wavelengths. The third partially reflecting device is locatable to reflect the third wavelength range of radiation reflected by the second partially reflecting device to the third detector and to transmit other wavelengths. The reflector is locatable to reflect radiation transmitted by the third partially reflecting device to the fourth detector.

The apparatus preferably includes respective bandpass filters having respective negligible out-of-band transmission characteristics. Such a bandpass filter is preferably being interposed between the second partially reflecting device and the second detector, between the third partially reflecting device and the third detector, and between the reflector and the fourth detector.

It has been found that a combination of detectors and a radiation direction system as described above is advantageous for allowing combined fluorescence and reflectance imaging with a single imaging device, and does not necessarily require any moving parts in the imaging device itself, thereby reducing the weight and cost of the imaging device.

Alternatively, the radiation direction system may include a prism system configured to direct the respective wavelength ranges of the incident radiation onto the respective corresponding detectors.

In accordance with a further aspect of the invention, there is provided a method and apparatus for producing illuminating radiation for fluorescence and reflectance imaging. The method involves selectively producing first and second spectral distributions of electromagnetic radiation for fluorescence/NIR reflectance imaging and white light reflectance imaging respectively. The first spectral distribution includes an excitation component received from a first optical subsystem of an optical system and a near infrared (NIR) component received from a second optical subsystem of an optical system. The second spectral distribution includes a white light illumination component received from the first optical subsystem. The apparatus includes the optical system including the first and second optical subsystems, operable to selectively produce the first and second spectral distributions.

Thus, greater flexibility may be achieved by the use of first and second optical subsystems. For example, if desired, a longer wavelength normalization component such as a selected band of NIR radiation may be employed, to provide enhanced correction for geometric factors in a fluorescence image due to the greater similarity of the reflectance spectra in the selected NIR wavelength range of normal and abnormal tissues. In such an exemplary system, because the NIR component is received from the second optical subsystem, there is no need for the NIR component to travel through the first optical subsystem, thereby preventing unnecessary heating damage to components of the first optical subsystem.

In addition, because the first and second optical subsystems are provided in a single optical system, fluorescence and reflectance imaging may be achieved without the need to manually disconnect one light source and connect another to the endoscope.

Selectively producing the first and second spectral distributions preferably involves receiving the white light illumination component and the excitation component at the first optical subsystem, and receiving the NIR component at the second optical subsystem. Selectively producing may then further involve transmitting the excitation component from the first optical subsystem and the NIR component from the second optical subsystem in a first operational mode for fluorescence/NIR reflectance imaging, and transmitting the white light illumination component from the first optical subsystem while blocking the NIR component in a second operational mode for white light reflectance imaging.

Similarly, with respect to the apparatus, the first optical subsystem is preferably operable to receive the white light illumination component and the excitation component, to transmit the excitation component in a first operational mode for fluorescence imaging, and to transmit the white light illumination component in a second operational mode for white light reflectance imaging. Likewise, the second optical subsystem is preferably operable to receive the NIR component, to transmit the NIR component in the first operational mode and to block the NIR component in the second operational mode.

Selectively producing may further involve directing radiation transmitted by the first and second optical subsystems along a common optical path.

In this regard, the optical system may include a combiner locatable to direct the radiation transmitted by the first and second optical subsystems along the common optical path. For example, the combiner may include a dichroic reflecting device locatable to transmit radiation transmitted by the first optical subsystem along the path and to reflect radiation transmitted by the second optical subsystem along the path. The optical system preferably includes a lens locatable in the path to focus the radiation transmitted by the first and second optical subsystems onto an exit port.

The apparatus may include an optical fiber bundle, an open end of which acts as the exit port. For example, this may include an illumination optical fiber bundle of an endoscope.

The method preferably further involves receiving input radiation including the excitation, NIR and white light illumination components, providing the excitation and white light illumination components to the first optical subsystem, and providing the NIR component to the second optical subsystem.

Similarly, the apparatus preferably includes at least one electromagnetic radiation source for providing the white light illumination component and the excitation component to the first optical subsystem and for providing the NIR component to the second optical subsystem.

The electromagnetic radiation source may include a beam splitter operable to receive input electromagnetic radiation, to reflect the white light illumination component and the excitation component for receipt by the first optical subsystem and to transmit the NIR component for receipt by the second optical subsystem. If so, then the optical system preferably includes a redirecting device, such as an optical fiber bundle or a liquid light guide for example, locatable to receive the NIR component from the beam splitter and to redirect the NIR component to the second optical subsystem.

The electromagnetic radiation source may also include a lamp operable to provide the input electromagnetic radiation to the beam splitter.

Producing the first spectral distribution may involve producing, as the excitation component, radiation having blue and shorter wavelengths, and may also involve producing, as the NIR component, radiation including wavelengths between about 750 nm and at least about 900 nm.

Producing the second spectral distribution may involve producing, as the white light illumination component, visible light. For example, this may include wavelengths from 400 nm to 700 nm. The optical system is preferably operable to produce such components.

More particularly, producing the first spectral distribution preferably involves producing, as the excitation component, a short wavelength component sufficiently short to cause fluorescence in an object, and producing, as the NIR component, a long wavelength component longer than fluorescence emission wavelengths of the object. Advantageously, this may permit a complete full wavelength range fluorescence spectrum to be measured by the spectroscopy device without interference from the reflected NIR component radiation. Producing such components preferably further involves producing the first spectral distribution to have an intensity at the fluorescence emission wavelengths sufficiently below an intensity of fluorescence radiation emitted by the object in response to the short wavelength component to permit detection of the fluorescence radiation. For example, where the object is tissue, the first spectral distribution may be produced to have negligible intensity at green wavelengths and at red and NIR wavelengths shorter than 750 nm, to avoid any appreciable reflectance by the object at the fluorescence emission wavelengths, which would introduce measurement error. The optical system is preferably operable to produce the first spectral distribution in this manner.

In one embodiment of the invention, for example, producing the first spectral distribution involves producing radiation consisting essentially of the short and long wavelength components, the short wavelength component consisting essentially of radiation having wavelengths between about $4\frac{1}{2} \times 10^2$ nm and about $4 \times 10^2$ nm, and the long wavelength component consisting essentially of radiation having wavelengths between about $7\frac{1}{2} \times 10^2$ nm and at least about $9 \times 10^2$ nm. The optical system may be operable to produce this distribution.

The optical system preferably includes a filter system.

The first optical subsystem may include a filtering device operable to transmit the excitation component while attenuating other wavelengths in the first operational mode and operable to transmit the white light illumination component in the second operational mode. For example, such a filtering device may include a blue bandpass (BP) filter for transmitting the excitation component in the first operational mode, and a color balance filter interchangeable with the blue BP filter, for transmitting the white light illumination component in the second operational mode.

Similarly, the second optical subsystem may include a filtering device operable to transmit the NIR component while attenuating other wavelengths in the first operational mode and operable to block the NIR component in the second operational mode. For example, such a filtering device may include at least one of a longpass (LP) filter and a bandpass (BP) filter for transmitting the NIR component in the first operational mode, and a light stopper interchangeable with the at least one filter, for blocking the NIR component in the second operational mode.

If desired, the apparatus may include an electromagnetic radiation source locatable to produce input electromagnetic radiation for receipt by the optical system.

An imaging system may be provided including an apparatus for producing illuminating radiation as described above and further including a radiation direction system configured to direct respective wavelength ranges of incident radiation received from an object illuminated by the apparatus device onto respective corresponding detector areas of an imaging device.

Similarly, in accordance with another aspect of the invention, there is provided an imaging system for performing both fluorescence imaging and reflectance imaging using the same detectors in the imaging device. The imaging system includes an apparatus for producing illuminating radiation as described above, and further includes a plurality of detectors for receiving radiation from an object illuminated by the apparatus, and a radiation direction system. The radiation direction system is configured to direct respective wavelength ranges of the radiation onto the plurality of detectors respectively, to define for each of the detectors a spectral response range with which the radiation from the object is convoluted. Advantageously, embodiments of such a system may be produced which allow for convenient automated switching between fluorescence and reflectance imaging modes, without the need to manually disconnect and reconnect different illuminating radiation sources or imaging devices. Similarly, the radiation direction system may permit the manufacture of light-weight and inexpensive cameras or other imaging devices suitable for both fluorescence and reflectance imaging, that do not require moving parts to switch between fluorescence and reflectance imaging modes.

The radiation direction system is preferably configured to direct a first of the wavelength ranges less than $5\times10^2$ nm to a first of the detectors, to direct a second of the wavelength ranges between $5\times10^2$ nm and $6\times10^2$ nm to a second of the detectors, to direct a third of the wavelength ranges between $6\times10^2$ nm and $8\times10^2$ nm to a third of the detectors, and to direct a fourth of the wavelength ranges between $8\times10^2$ nm and $9\times10^2$ nm to a fourth of the detectors.

The plurality of detectors preferably includes four detectors for receiving radiation in four respective wavelength ranges.

Preferably, at least one of the detectors has a selectively adjustable gain adjustable to produce an improved image of an object in response to input radiation.

In accordance with another aspect of the invention, there is provided a method and apparatus for detecting tissue oxygenation. The method involves producing a first signal in response to radiation reflected by tissue in a first near infrared wavelength band, and producing a second signal in response to radiation reflected by the tissue in a second near infrared wavelength band selected such that a ratio of an absorption coefficient of oxyhemoglobin to an absorption coefficient of deoxyhemoglobin in the second wavelength band is different than the ratio in the first wavelength band. The first and second signals are operable for use in producing an oxygenation image of the tissue. The apparatus includes first and second detectors operable to produce the first and second signals respectively.

In this regard, it is noted that cancerous tissues exhibit hypoxia caused by increased oxygen consumption due to rapid growth of cancerous cells, and therefore contain more deoxyhemoglobin than oxyhemoglobin. Therefore, because the signals are produced in response to two wavelength bands in which the ratios of the absorption coefficient of oxyhemoglobin to that of deoxyhemoglobin are different, cancerous tissues will tend to reflect with a different intensity relative to normal tissue in one of the wavelength bands than in the other wavelength band. This allows the signals to be combined, if desired, to produce an oxygenation image of the tissue in which cancerous regions are highlighted, to increase diagnostic accuracy. Indeed, either of these signals taken alone could be used to produce an oxygenation image, however, it would be undesirable to do so as the combination of the two signals serves to correct or normalize for geometric factors, as discussed above.

In addition, it is noted that the heme proteins, i.e. oxyhemoglobin and deoxyhemoglobin, tend to dominate the reflectance spectra at near infrared wavelengths. Therefore, producing signals in response to radiation reflected by the tissue in two different near infrared wavelength bands serves to minimize measurement errors that would result if either or both of the signals were produced in response to other wavelengths such as visible wavelengths, at which other tissue chromophores dominate or contribute significantly to the reflectance spectra.

Producing the first and second signals preferably involves directing the radiation reflected by the tissue in the first and second near infrared wavelength bands to a first detector and a second detector respectively. This may involve directing to the first detector, as the radiation reflected by the tissue in the first near infrared wavelength band, radiation in a near infrared wavelength band in which the absorption coefficient of deoxyhemoglobin is greater than the absorption coefficient of oxyhemoglobin. Similarly, this may involve directing to the second detector, as the radiation reflected by the tissue in the second near infrared wavelength band, radiation in a near infrared wavelength band in which the absorption coefficient of oxyhemoglobin is greater than the absorption coefficient of deoxyhemoglobin. The apparatus may include a radiation direction system configured to direct the radiation in the above manners.

Such embodiments may permit even greater diagnostic accuracy. For example, in a near infrared wavelength band in which the absorption coefficient of deoxyhemoglobin is greater than that of hemoglobin, such as 750–800 nm for example, cancerous tissues, which contain more deoxyhemoglobin due to hypoxia, appear darker than normal tissues. Conversely, in a near infrared wavelength band in which the absorption coefficient of oxyhemoglobin is greater than that of deoxyhemoglobin, such as 800–900 nm for example, cancerous tissues appear brighter than normal tissue as they contain relatively less oxyhemoglobin than normal tissues. Thus, signals representing the reflectances of tissues in two such wavelengths may be combined to produce an oxygenation image providing even greater contrast between cancerous and normal tissues.

The method preferably further involves producing the oxygenation image of the tissue in response to the first and second signals. This may involve causing the first signals to be provided to a first color channel input of a multicolor display device, and causing the second signals to be provided to a second color channel input of the display device. The apparatus may include a processor circuit configured to produce the oxygenation image, and the processor circuit may also be configured to cause the signals to be provided to the respective color channel inputs.

For example, the first signals, such as those produced in response to reflectance by the tissue in a first near infrared wavelength band in which the absorption coefficient of deoxyhemoglobin is greater than that of oxyhemoglobin, may be provided to the green channel input of a color monitor, to produce a green image in which normal tissues appear bright green while cancerous tissues appear dark. Simultaneously, the second signals, such as those produced in response to reflectance in a second wavelength band in which the absorption coefficient of oxyhemoglobin is greater than that of hemoglobin, may be provided to the red channel input of the color monitor, to produce a red image in which cancerous tissues appear bright red while normal tissues appear dark. Thus, in the superposition of these two images on the monitor, normal tissues appear bright green, while cancerous tissues appear bright red. Points in the tissue that are not cancerous but appear dark due to geometrical factors will appear dark in both the green and red colors.

Alternatively, or in addition, producing the oxygenation image may involve, for each point in the tissue, causing a corresponding pixel of a multi-pixel display device to be illuminated with a brightness proportional to a ratio of a strength of the first signal corresponding to the point to a strength of the second signal corresponding to the point. The processor circuit may be configured to achieve this.

Similarly, producing the oxygenation image may involve producing third signals such that for each point in the tissue, a strength of the third signal corresponding to the point is proportional to a ratio of a strength of the first signal corresponding to the point to a strength of the second signal corresponding to the point, and causing the third signals to be provided to a third color channel input of the display device. The processor circuit may be configured to produce the third signals and to cause them to be provided to the third color channel input.

The apparatus preferably includes third and fourth detectors operable to produce respective signals in response to electromagnetic radiation in respective third and fourth wavelength bands.

In such a case, the radiation direction system is preferably configured to direct the radiation in the third and fourth wavelength bands onto the third and fourth detectors. For example, such a radiation direction system may include first, second and third partially reflecting devices and a reflector, configured in a similar manner to the radiation direction system described above in connection with the previous aspect of the invention.

In accordance with another aspect of the invention, there is provided a method, apparatus, computer readable medium and signal for producing a fluorescence image of tissue. The method involves producing ratio signals such that for each point in the tissue, a strength of the ratio signal corresponding to the point is proportional to a ratio of an intensity of reflectance of the point in a first near infrared (NIR) wavelength band to an intensity of fluorescence of the point. The method further involves causing the ratio signals to be provided to an input of a display device to produce the fluorescence image of the tissue. The apparatus includes a processor circuit configured to carry out the method. The computer readable medium provides codes for directing a processor circuit to produce the fluorescence image, and similarly, the signal is embodied in a carrier wave and includes code segments for directing a processor circuit to implement the method.

Causing the ratio signals to be provided to the input may involve causing the ratio signals to be provided to a first color channel input of a multicolor display device. The method may further involve causing fluorescence signals produced in response to the fluorescence to be provided to a second color channel input of the display device, and similarly, may involve causing NIR reflectance signals produced in response to the reflectance in the first NIR wavelength band to be provided to a third color channel input of the display device. For example, the ratio signals, the fluorescence signals and the NIR reflectance signals may be provided to a blue channel input, a green channel input and a red channel input respectively of the display device.

In accordance with another aspect of the invention, there is provided a method, apparatus, computer readable medium and signals for producing a fluorescence image of tissue. The method involves causing fluorescence signals produced in response to fluorescence of the tissue to be provided to a first color channel input of a multicolor display device, causing first near infrared (NIR) reflectance signals produced in response to reflectance of the tissue in a first NIR wavelength band to be provided to a second color channel input of the display device, and causing second NIR reflectance signals produced in response to reflectance of the tissue in a second NIR wavelength band to be provided to a third color channel input of the display device. The apparatus includes a processor circuit configured to carry out the method. The computer readable medium provides codes for directing a processor circuit to produce the fluorescence image, and similarly, the signal is embodied in a carrier wave and includes code segments for directing a processor circuit to implement the method.

Causing the signals to be provided to the inputs may involve causing the fluorescence, first NIR reflectance and second NIR reflectance signals to be provided to a green channel input, a red channel input and a blue channel input respectively of the display device.

In accordance with another aspect of the invention, there is provided a method and apparatus for performing both fluorescence imaging and reflectance imaging using the same detectors in an imaging device or camera. The method involves sharing detectors in a multi-spectral-channel imaging device for both fluorescence imaging and reflectance imaging, generating a desired detection spectral profile for each imaging channel by convoluting the illumination controlled, tissue remittance spectrum with the spectral response of each individual imaging channel, and coordinating detector gain adjustment and illumination mode switching through computer control.

Turing to some further aspects, the invention also provides a light beam detection system comprising: a) an area sized to receive the light beam, b) a beam separator disposed in the area to separate a small portion of the light beam from a remainder of the light beam to provide a separated light beam and a remainder light beam and transmit the separated light beam to a spectroscopy device, c) an imaging device disposed in the area to operably receive the remainder light beam to provide an image therefrom, and d) a spectroscopy device optically connected to the beam separator to receive the separated light beam to provide a spectrum therefrom. In some embodiments, the spectroscopy device can be located outside of the light beam and the beam separator comprises a light redirection device sized and located to intercept a small area of the light beam and change the direction of such small area toward the spectroscopy device, and wherein the light redirection device imparts a small residual image in the remainder light beam corresponding to the location of the light redirection device in the light beam. If desired, the light redirection device and the small residual image can be located substantially in the center of the light beam.

The light redirection device can separate substantially all light incident on the light redirection device from the remainder light beam, and can be a measurement port of the spectroscopy device, a mirror, a prism, a light guide, or a lens. The beam separator can be a beam splitter. The beam separator can be a beam splitter that intercepts a large portion of the light beam such that the beam splitter does not leave a significant residual image in the remainder light beam, and wherein the beam splitter transmits substantially more than about 50%, 80% or 90% of the electromagnetic radiation in the light beam to the imaging device and reflects substantially less than about 50%, 20% or 10% of the electromagnetic radiation in the light beam to the spectroscopy device.

The imaging device can be a pixelated detector such as a CCD, an intensified CCD, a CID, a CMOS, a photodiode array, and a photomultiplier array, or a non-pixelated detector such as a film camera. The spectroscopy device can be a spectrometer, a scanning monochromater coupled with a single channel detector, an imaging spectrograph coupled with an array detector, or an interferometer based Fourier transform (FT) type spectrometer.

In some embodiments, the beam separator can be located in substantially a same image plane as the imaging device, substantially in front of and either abutting or not touching the imaging device, or behind the imaging device. The system can further comprise a first focusing element such as a lens or curved mirror in front of the beam separator and a second focusing element between the beam separator and the imaging device, the first focusing element and the second focusing element located to provide a first conjugate image plane substantially at the beam separator and a second conjugate image plane substantially at the imaging device.

The system can further comprise a display device operably connected to the imaging device to display an image from the imaging device or a display device operably connected to the spectroscopy device to display a spectrum from the spectroscopy device. The device can be a single or multiple display devices operable to contemporaneously display both the image from the imaging device and the spectrum from the spectroscopy device. The system can also further comprise a light collection port sized to receive the light beam directly from a sample and an optical relay system operably connected between the light collection port and the area to transmit the light beam to the area.

The system can still further comprise an image separator comprising a plurality of light selection elements that separates the image into a plurality of selected wavelength region images wherein each selected wavelength region image corresponds to a different wavelength region of the range of wavelengths in the light beam. The image separator can comprise a plurality of imaging beam splitters each of which selects for different selected wavelength regions to provide the selected wavelength region images and directs the selected wavelength region images to different imaging devices. The different imaging devices can be different regions of a single imaging detector or multiple detectors.

The imaging beam splitters can disposed linearly along the light beam or there can be at least three imaging beam splitters disposed to reflect the selected wavelength region images in at least three different radial directions and the different imaging devices can be disposed radially about the light beam to receive the selected different wavelength images. The imaging beam splitters can be disposed alternatingly such that a first sub-set of the imaging beam splitters direct a first set of selected wavelength region images in a first direction and a second sub-set of the imaging beam splitters direct a second set of selected wavelength region images in a second direction that can be substantially 180° away from the first direction.

The imaging beam splitters can select for all desired wavelength region or select for all but one desired, non-selected different wavelength region to provide a non-selected wavelength region image, wherein the image separator further comprises an imaging device located in the light beam and behind the imaging beam splitters to directly receive the non-selected wavelength region image. The different wavelength regions can comprise at least two of UV to blue light, visible light, near-infrared light and infrared light. The display device can be operably connected to the image separator to contemporaneously display at least two images selected from the UV to blue light, visible light, near-infrared light and infrared light, and can be further able to contemporaneously display the spectrum from the spectroscopy device.

The system can further comprise a controller operably connected to the imaging device and the spectroscopy device and containing computer-implemented programming that controls the imaging device and the spectroscopy device, and if desired controls the selection and display of different wavelength regions.

In other aspects, the present invention provides image and spectral detection systems comprising an image detector disposed substantially coplanar with a light collection element for a spectroscopy device, the image detector and the light collection element together sized to receive a light beam. The image detector and the light collection element can be, for example, side-by-side, the light collection element can be encompassed by the image detector, the light collection element can be located substantially in the center of the image detector, the light collection element can be a measurement port for a spectroscopy device located immediately behind the image detector, the light collection element can be an input end of a light guide that transmits collected light to a remotely located spectroscopy device, the light collection element can be a focusing element that transmits collected light to a remotely located spectroscopy device, or the light collection element can be a mirror that transmits collected light to a remotely located spectroscopy device. Further, the imaging device can be able to determine spectra and the light collection element can comprise a portion of the imaging device dedicated to spectral determination. The image detector can have an area to receive the light beam and the light collection element that can be less than about 5% or 3% of the area of the image detector.

In still other aspects, the present invention provides imaging systems able to provide a plurality of images corresponding to different wavelength regions of an initial image. The imaging system can comprise an image separator comprising a light beam path and a plurality of imaging beam splitters disposed in the light beam path, each of the imaging beam splitters selecting for different selected wavelength regions of the initial image to provide corresponding different selected wavelength region images and directing the different selected wavelength region images to different imaging devices. The system can further comprise at least one display device operably connected to display at least one of the different selected wavelength region images from the different imaging devices.

In still other aspects, the present invention provides methods making and using the devices and systems and the like described herein. For example, the methods can comprise detecting a light beam comprising: a) separating via a beam separator a small portion of the light beam from a remainder of the light beam to provide a separated light beam and a remainder light beam, b) transmitting the separated light beam to a spectroscopy device optically connected to the beam separator, and, c) transmitting the remainder light beam to an imaging device optically connected to receive the remainder light beam and to provide an image therefrom. The method can further comprise displaying on a display device a spectrum from the spectroscopy device and the image from the imaging device, and if desired imparting via the light redirection device a small residual image in the remainder light beam corresponding to the location of the light redirection device in the light beam. The small residual image can be imparted substantially in the center of the light beam or elsewhere as desired.

The methods can also provide a plurality of images derived from different wavelength regions of an initial image, the methods comprising a) passing a light beam carrying the initial image along a light beam path in an image separator comprising a plurality of imaging beam splitters disposed in the light beam path, b) selecting different selected wavelength regions of the initial image via the imaging beam splitters to provide selected wavelength region images, and, c) directing the selected wavelength region images to different imaging devices.

In still other aspects, the present invention provides means plus function and step plus function embodiments of the various systems, features, devices, methods, etc., herein.

These and other aspects, features and embodiments are set forth within this application, including the following Detailed Description and attached drawings. The present invention comprises a variety of aspects, features and embodiments; such multiple aspects, features and embodiments can be combined and permuted in any desired manner. In addition, various references are set forth herein, including in the Cross-Reference To Related Applications, that discuss certain compositions, apparatus, methods or other information; all such references are incorporated herein by reference in their entirety and for all their teachings and disclosures, regardless of where the references may appear in this application.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

The present invention is directed to systems, apparatus and methods that simultaneously provide both high quality images and spectra of a given object or sample, wherein the light removed from the light beam for the spectral determination does not significantly detract from the quality of the image, and can, if desired, provide an aiming pointer helpful both for aiming the optical device in general and for determining the precise location from which the spectra is being taken. If desired, the systems can provide multiple images, for example relating to different wavelength regions of light emanating from the sample, and/or different spectra. The systems and methods can be advantageously used with optical systems such as telescopes, microscopes, cameras, endoscopes and other imaging devices.

The devices comprise an area that receives a light beam emanating from a sample (for example, due to fluorescence or reflectance). Within the area are a beam separator that directs a portion of the light beam to a spectroscopy device and that passes the remainder of the light beam onto an imaging device. Typically, the imaging device is maintained directly in the light beam and the spectroscopy device is located outside the light beam, but both can be maintained outside the light beam, the imaging device can be the device located outside the light beam, or other arrangements can be provided if desired. The spectroscopy device can be any desired device capable of providing a spectrum from the light beam, such as a scanning monochromater coupled with a single channel detector, an imaging spectrograph coupled with an array detector, an interferometer based Fourier transform (FT) type spectrometer, or other desired devices. Similarly, the imaging device can be any desired imager, such as a pixilated imaging device such as a CCD, an intensified CCD, a CMOS, a CID (charge injection device), a photodiode array, a photomultiplier array, or a non-pixelated device such as a film camera.

Figure 1:
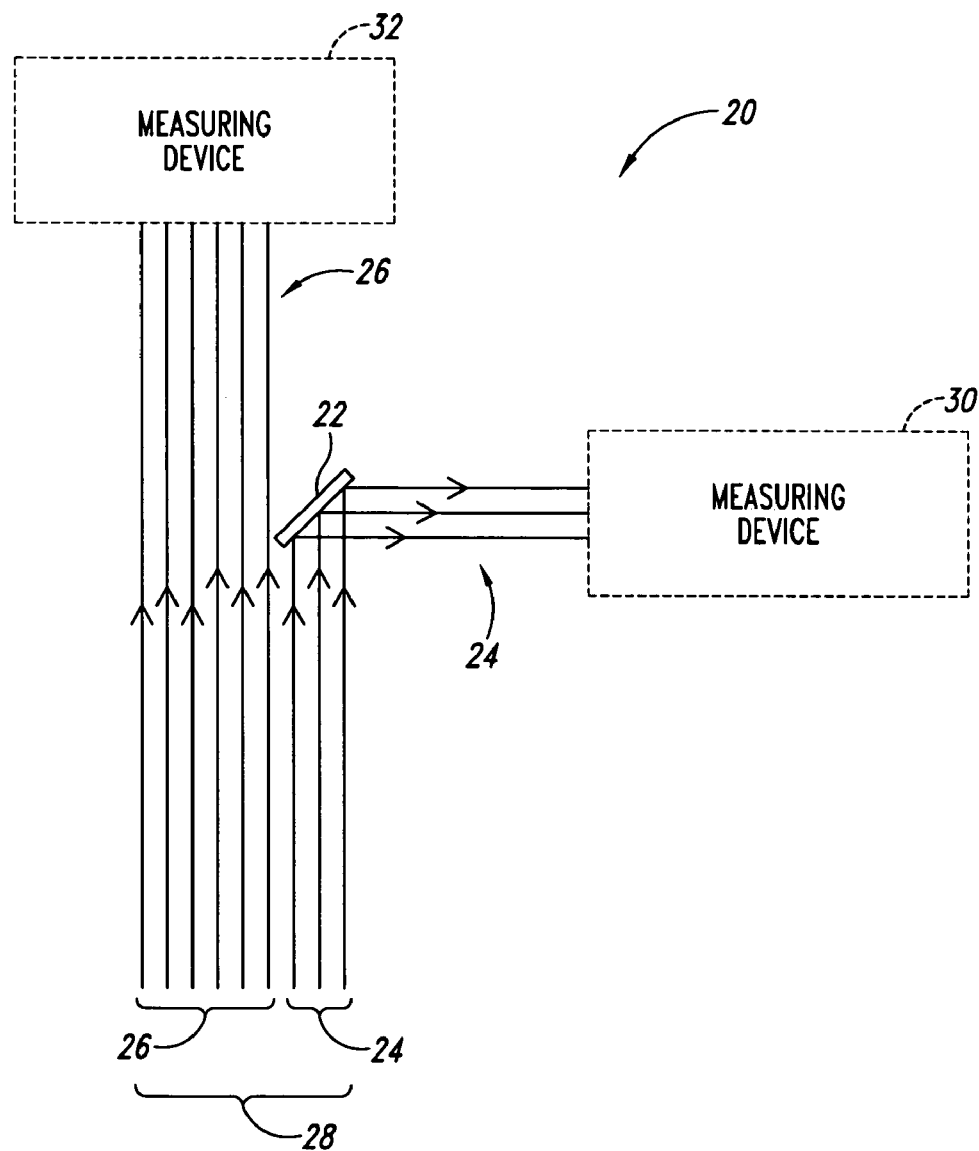
FIG. 1 is a schematic representation of an apparatus for facilitating contemporaneous measurements of electromagnetic radiation with multiple measuring devices, according to a first embodiment of the invention.

Referring to FIG. 1, an apparatus for facilitating contemporaneous measurements of electromagnetic radiation with multiple measuring devices, according to a first embodiment of the invention is shown generally at 20. The apparatus 20 includes a beam-directing device 22 locatable to cause first and second adjacent groups 24 and 26 of rays of an electromagnetic radiation beam 28 to be directed for receipt by first and second measuring devices 30 and 32 respectively.

System

Figure 2:
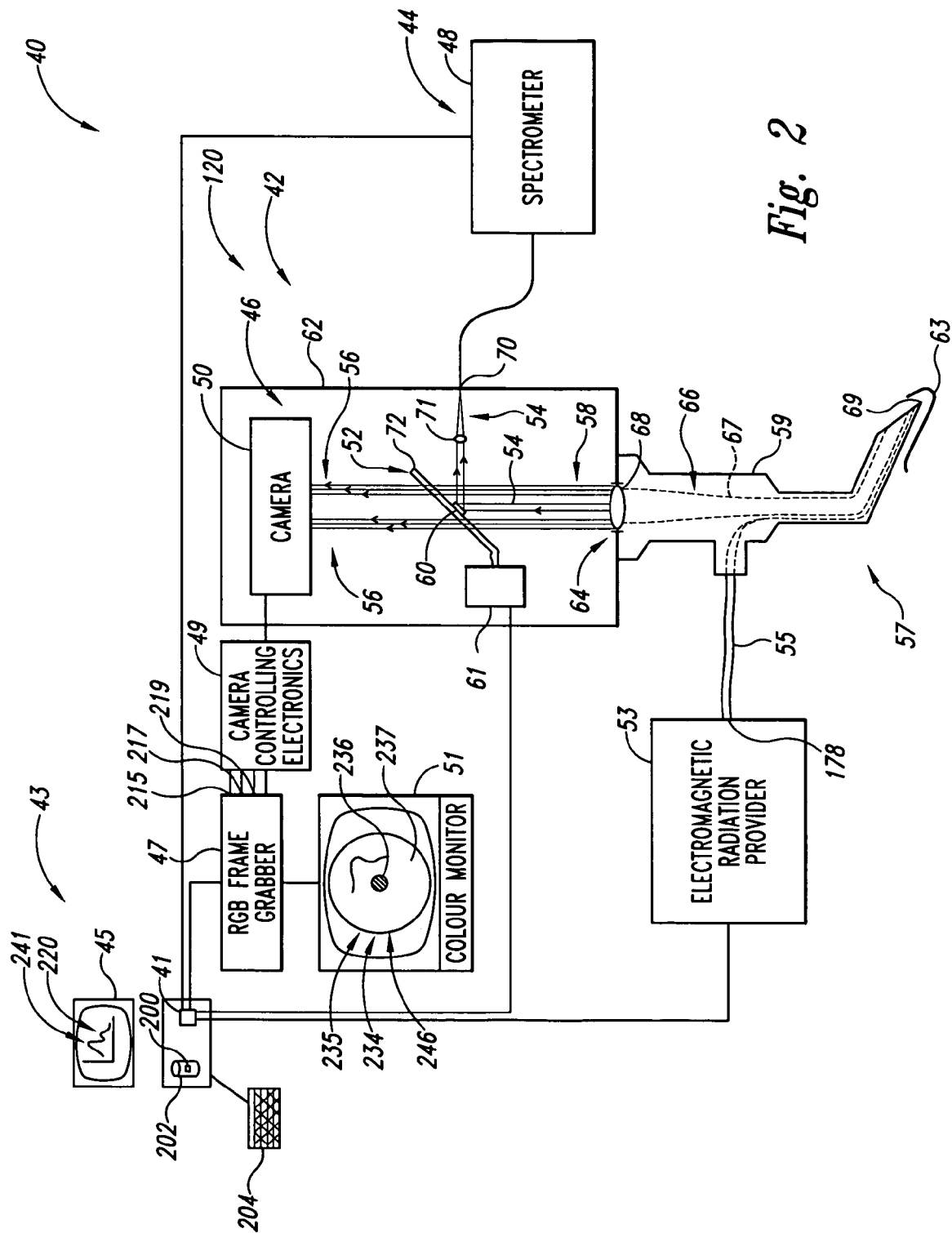
FIG. 2 is a block diagram of system including an apparatus for facilitating contemporaneous measurements of electromagnetic radiation with multiple measuring devices, according to a second embodiment of the invention.

Referring to FIG. 2, an electromagnetic radiation measuring system is shown generally at 40. The system 40 includes an apparatus 42 for facilitating contemporaneous measurements of electromagnetic radiation with multiple measuring devices, according to a second embodiment of the invention. The system 40 includes first and second measuring devices 44 and 46, which in this embodiment include a spectrometer 48 and an imaging device, which in this embodiment is a charge-coupled device (CCD) camera 50, respectively. The apparatus 42 includes a beam-directing device 52 locatable to cause first and second adjacent groups 54 and 56 of rays of an electromagnetic radiation beam 58 to be directed for receipt by the first and second measuring devices 44 and 46 respectively.

The system 40 further includes a processor circuit 41, which in this embodiment is housed within or outside a general-purpose computer 43 which includes a monitor 45. The processor circuit 41 is in communication with the spectrometer 48, and is programmed or configured to display, on the monitor 45, a graphical representation of spectra measured by the spectrometer.

The processor circuit 41 is also in communication with an RGB color frame grabber 47 and with camera controlling electronics 49 for controlling the CCD camera 50. Generally, the camera controlling electronics serve to control four individual CCD detector areas within the CCD camera 50, described in greater detail below, by synchronizing their signals and adjusting their gains. The camera controlling electronics 49 also transmit signals from the individual CCDs to the RGB color frame grabber 47, which digitizes such signals and transmits data representing digital color images to the processor circuit 41. The processor circuit is additionally in communication with a color monitor 51 used for displaying color images measured by the CCD camera.

The processor circuit 41 is also in communication with an apparatus for producing illuminating radiation for fluorescence and reflectance imaging, which in this embodiment is an electromagnetic radiation provider 53. The electromagnetic radiation provider 53 provides illumination electromagnetic radiation, via an optical fiber bundle 55 to a viewing device 57, which in this embodiment includes an endoscope 59. The optical fiber bundle 55 extends through the endoscope 59, to direct the illumination radiation onto an object 63 to be viewed by the system 40. In this embodiment, the object 63 includes human or animal tissues and organs. More generally, however, throughout this specification, including the claims, the word "object" is used in an optical sense to mean anything viewed, imaged or measured by the system 40.

The processor circuit 41 is in further communication with a motion mechanism 61 operable to move the beam-directing device 52 into and out of the path of the beam 58 as desired. The motion mechanism may include a solenoid or a motor, for example. Alternatively, the beam-directing device 52 may be permanently fixed in the path of the beam 58.

Camera Module

Figure 3:
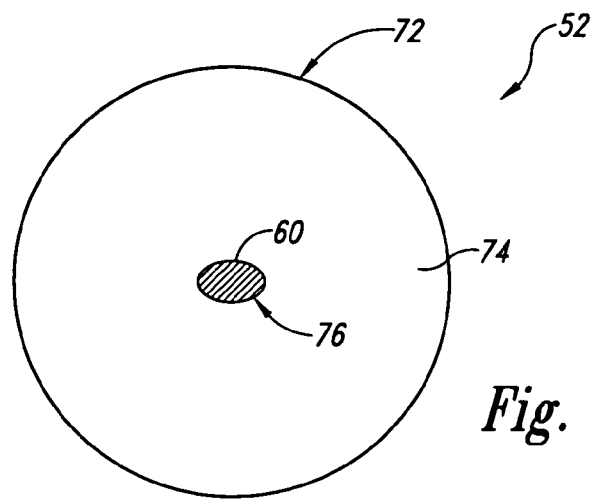
FIG. 3 is a view of a beam-directing device of the apparatus shown in FIG. 2.

Referring to FIGS. 2 and 3, in this embodiment, the beam-directing device 52 is locatable to direct the first group 54 of rays for receipt by the first measuring device 44. To achieve this, the beam-directing device 52 includes a reflective surface 60 locatable in the beam 58 to reflect the first group 54 of rays from the beam 58 while permitting the second group 56 of rays to bypass the reflective surface 60.

In this embodiment, the apparatus 42 further includes a housing 62 in which the beam-directing device 52 is locatable. The housing has an input port 64 configured to receive the electromagnetic radiation beam 58 from an imaging channel 66 of the endoscope 59, and to direct the beam 58 to the beam-directing device 52. The imaging channel 66 includes a coherent optical fiber bundle 67 attached at one end to the input port 64 through an eyepiece 68 of the endoscope 59. An opposite end of the coherent optical fiber bundle 67 extends through the endoscope 59 to a tip 69 thereof, in proximity to the object 63. Alternatively, however, the imaging channel may include a rigid optical path in the endoscope 59.

In this embodiment, the housing 62 also has a first measurement port 70 for providing the first group 54 of rays to the first measuring device 44, or more particularly, to the spectrometer 48. The beam-directing device 52 is thus locatable in the housing to receive the beam 58 from the input port 64 and to direct the first group 54 of rays to the first measurement port 70.

The apparatus 42 in the present embodiment also includes a lens 71 locatable within the housing 62 to focus the first group 54 of rays onto the first measurement port 70.

In this embodiment the CCD camera 50 and the motion mechanism 61 are also housed within the housing 62.

Beam-directing Device

Referring to FIGS. 2 and 3, the beam-directing device is shown in greater detail at 52 in FIG. 3 and includes a removable mirror 72. The removable mirror 72 includes a transparent glass plate 74. In this embodiment, the reflective surface 60 includes a reflective coating on a central region 76 of the glass plate 74. More particularly, in this embodiment, the reflective coating reflects nearly 100% of visible and near infrared wavelengths of electromagnetic radiation incident thereon. Apart from the central region 76 having the reflective surface 60 thereon, the remainder of the glass plate 74 is coated with an anti-reflection coating to increase its transmittance of electromagnetic radiation to nearly 100%.

In this embodiment, the reflective surface 60 is elliptical in shape so that the reflected beam 54 has a circular cross-section when the removable mirror 72 is positioned at a 45 degree inclination to the incident electromagnetic radiation beam 58.

Alternatively, other types of beam-directing devices may be substituted. For example, the reflective surface 60 need not be at the center of the removable mirror 72. More generally, other types of reflective surfaces or other types of beam-directing devices, may be substituted to cause the first and second adjacent groups 54 and 56 of rays to be directed for receipt by the first and second measuring devices 44 and 46 respectively.

CCD Camera

Figure 4:
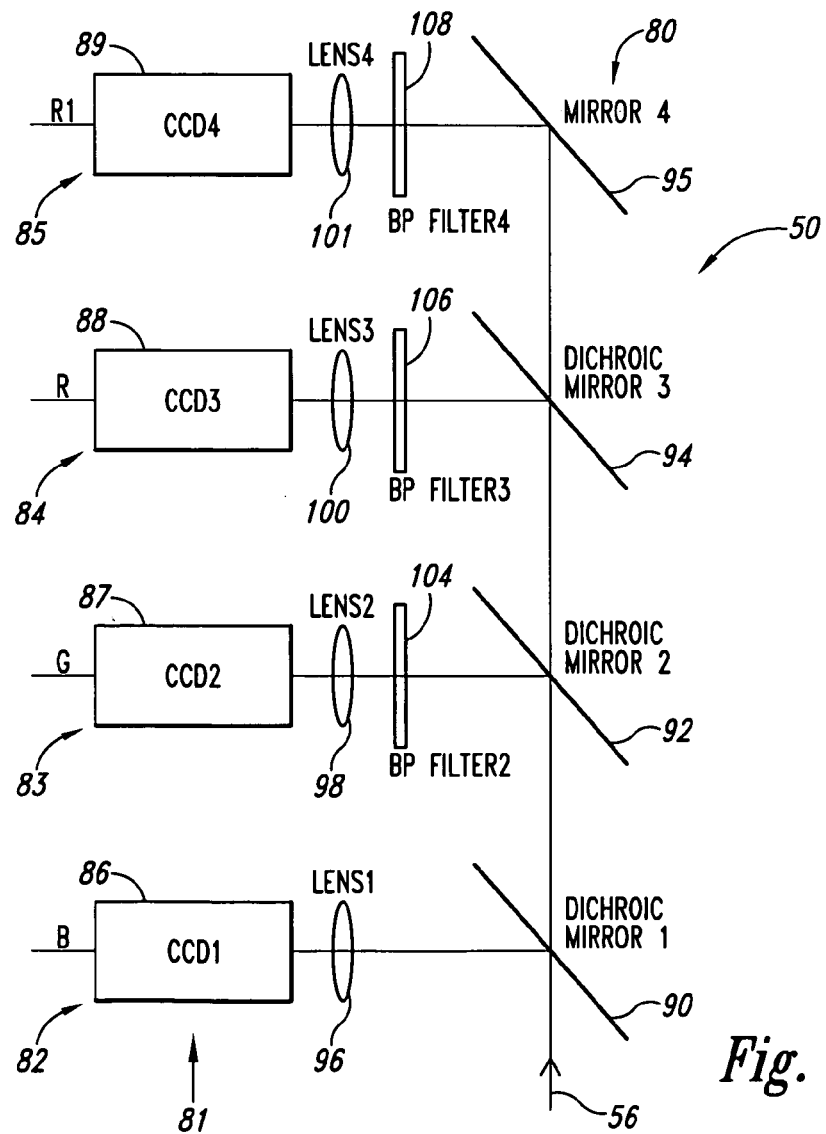
FIG. 4 is a schematic representation of an imaging device of the system shown in FIG. 2, having a radiation direction system.

Referring to FIGS. 2 and 4, the imaging device, or more particularly the CCD camera, is shown generally at 50 in FIG. 4. In this embodiment, the CCD camera 50 includes a radiation direction system shown generally at 80 configured to direct respective wavelength ranges of incident radiation in the second group 56 of rays onto respective corresponding detector areas 81 of the CCD camera 50. More particularly, the radiation direction system 80 is configured to direct four wavelength ranges of the incident radiation onto four respective corresponding detector areas 82, 83, 84 and 85 in the CCD camera 50. The detector areas 82, 83, 84 and 85 in the present embodiment include individual first, second, third and fourth detectors 86, 87, 88 and 89 respectively, which in this embodiment are individual charge-coupled devices. Alternatively, however, other types of detector areas, such as different regions of a single CCD for example, may be substituted.

Referring to FIG. 4, in this embodiment, the radiation direction system 80 includes a first partially reflecting device 90, a second partially reflecting device 92, a third partially reflecting device 94 and a reflector 95. The first partially reflecting device 90 is locatable so as to reflect a first wavelength range of the incident radiation to the first detector area 82 and to transmit other wavelengths. More particularly, the first partially reflecting device 90 includes a dichroic mirror which reflects electromagnetic radiation having wavelengths less than or equal to 500 nm, i.e. blue and shorter wavelength radiation, to the first detector area 82, and which transmits wavelengths longer than 500 nm toward the second partially reflecting device 92.

The second partially reflecting device 92 is locatable to reflect a second wavelength range of radiation transmitted by the first partially reflecting device 90 to the second detector area 83 and to transmit other wavelengths. More particularly, in this embodiment the second partially reflecting device 92 includes a dichroic mirror that reflects electromagnetic radiation having wavelengths less than or equal to 600 nm and transmits radiation having wavelengths longer than 600 nm.

The third partially reflecting device 94 is locatable to reflect a third wavelength range of radiation transmitted by the second partially reflecting device 92 to the third detector area 84 and to transmit other wavelengths. More particularly, in this embodiment the third partially reflecting device 94 includes a dichroic mirror that reflects electromagnetic radiation having wavelengths less than or equal to 800 nm and transmits radiation having wavelengths longer than 800 nm.

The reflector 95 is locatable to reflect radiation transmitted by the third partially reflecting device 94 to the fourth detector area 85.

Figure 6:
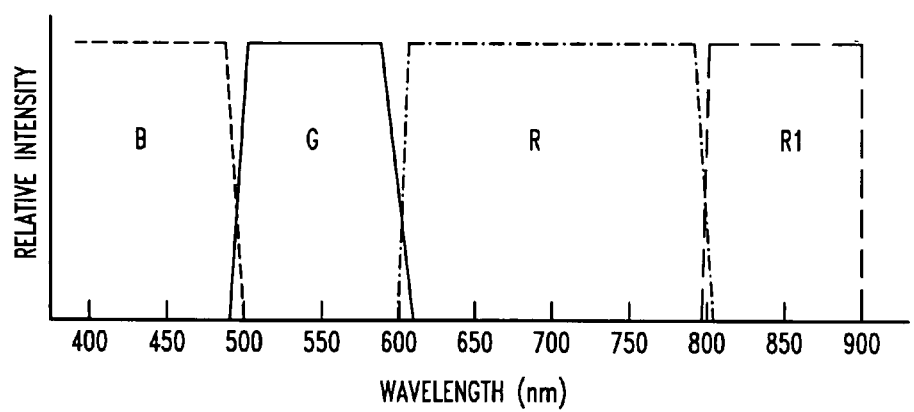
FIG. 6 is a graphical representation of spectral responses of four imaging channels of the imaging device shown in FIG. 4.

Thus, referring to FIGS. 4 and 6, the effect of the first, second and third partially reflecting devices 90, 92 and 94 and the reflector 95 is to direct "blue" electromagnetic radiation having wavelengths shorter than 500 nm to the first detector area 82, to direct "green" radiation having wavelengths between 500 and 600 nm to the second detector area 83, to direct "red" and near infrared (NIR) radiation having wavelengths between 600 nm and 800 nm to the third detector area 84, and to direct NIR radiation having wavelengths longer than 800 nm to the fourth detector area 85. This leads to four imaging channels, blue (B), green (G), red/NIR (R), and NIR (R1) having spectral responses as shown in FIG. 6. Thus, when the object 63 is illuminated by the electromagnetic radiation provider 53, radiation from the object is received at the detectors, and more particularly, the radiation direction system 80 is thus configured to direct respective wavelengths of the radiation from the object onto the plurality of detectors, to define for each of the detectors a spectral response range shown in FIG. 6, with which the radiation from the object is convoluted. This optical configuration of the camera facilitates performance of both fluorescence imaging and reflectance imaging with the same detectors, when used together with the electromagnetic radiation provider 53 shown in FIG. 9.

Referring back to FIG. 4, in this embodiment, the CCD camera 50 further includes a plurality of lenses and filters. For example, first, second, third and fourth lenses 96, 98, 100 and 101 are configured to focus radiation received from the radiation direction system 80 onto the first, second, third and fourth detector areas 82, 83, 84 and 85 respectively.

Referring back to FIG. 4, in this embodiment the radiation direction system 80 further includes a bandpass (BP) filter 104 having negligible out-of-band transmission characteristics, interposed between the second partially reflecting device 92 and the second detector area 83. More particularly, the BP filter 104 is a green bandpass filter which transmits radiation between 500 and 600 nm, and which transmits less than one part in $10^5$ of radiation outside this wavelength range. The BP filter 104 facilitates accurate fluorescence imaging by preventing measurement errors that would otherwise be introduced by reflected excitation light and NIR light, without detracting from the performance of the CCD camera 50 for white light reflectance imaging.

Similarly, in this embodiment the radiation direction system includes a BP filter 106 having negligible out-of-band transmission characteristics, interposed between the third partially reflecting device 94 and the third detector area 84. More particularly, the BP filter is a red-NIR bandpass filter which transmits radiation between 600 nm and 800 nm, and which transmits less than one part in $10^5$ outside this wavelength range. The BP filter 106 facilitates accurate red/NIR image acquisition in the 600 to 800 nm wavelength band by preventing measurement errors that would otherwise be introduced by reflected excitation light or other light outside this band, without detracting from the performance of the CCD camera 50 for white light reflectance imaging.

Similarly, in this embodiment the radiation direction system includes a BP filter 108 having negligible out-of-band transmission characteristics, interposed between the reflector 95 and the fourth detector area 85. More particularly, the BP filter 108 is a NIR bandpass filter which transmits radiation between 800 nm and 900 nm, and which transmits less than one part in $10^5$ outside this wavelength range. This facilitates accurate NIR image acquisition in the 800 to 900 nm wavelength band by preventing measurement errors that would otherwise be introduced by reflected excitation light or other light outside this wavelength band.

The BP filters 104, 106 and 108 provide for enhanced color separation beyond that provided by the first, second and third partially reflecting devices themselves. Such enhanced color separation is particularly advantageous in the present embodiment, where the CCD camera 50 is to be used for both reflectance and fluorescence imaging. In contrast, a conventional RGB color CCD camera used for white light reflectance imaging, for example, typically has out-of-band transmission characteristics as high as 10%, which would significantly increase measurement errors in a fluorescence image produced with the second detector area 83 and red/NIR reflectance images produced with the third and fourth detector areas 84 and 85. Thus, the negligible out-of-band transmission characteristics of the filters 104, 106 and 108 allow the CCD camera 50 to be used for both white light reflectance imaging and for fluorescence/NIR reflectance imaging, without the serious measurement errors that would result if a conventional RGB camera were used for this purpose. Alternatively, other combinations of lenses or filters may be substituted or such lenses and filters may be omitted, potentially resulting in lower image quality and increased measurement error.

In this embodiment, the CCD camera 50 as described above is designed to facilitate three imaging modalities: 1) conventional white light reflectance imaging; 2) fluorescence imaging; and 3) NIR reflectance imaging.

The third imaging modality, referred to herein as NIR reflectance imaging, is a new imaging modality designed to assess the blood flow and oxygenation status of tissues under viewing for further diagnostic accuracy improvement.

Figure 5:
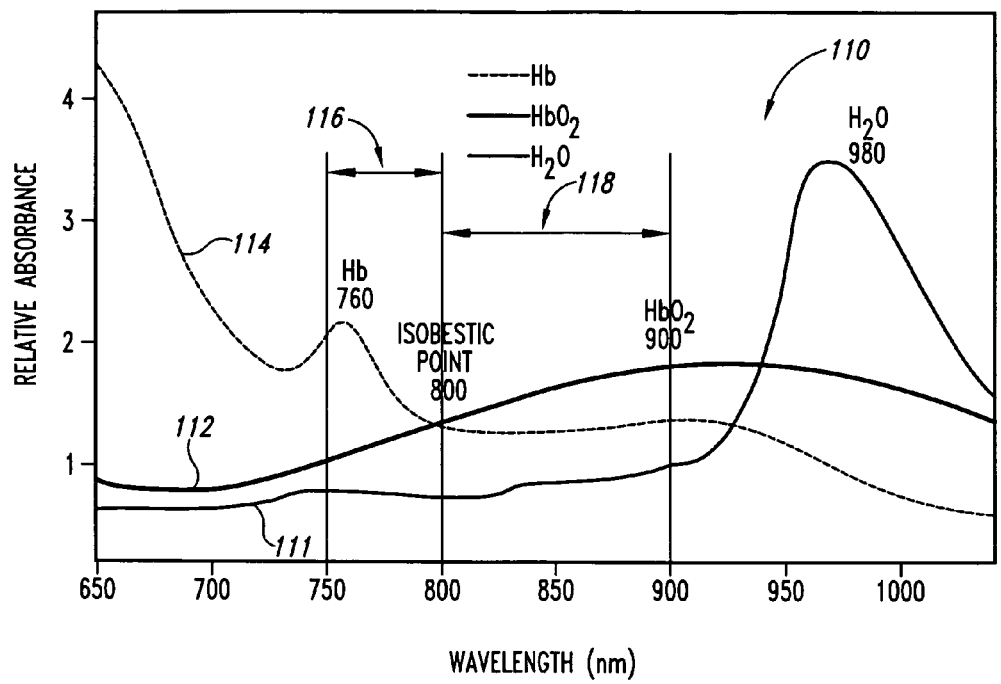
FIG. 5 is a graphical representation of absorption spectra of three major tissue chromophores (oxyhemoglobin, deoxyhemoglobin, and water) in the near infrared (NIR) wavelength range.

Referring to FIG. 5, the absorption spectra of major tissue chromophores (oxyhemoglobin ($HbO_2$), deoxyhemoglobin, (Hb), and water ($H_2O$)) in the NIR wavelength range are shown generally at 110. A water absorption spectrum 111 is relatively flat between 700 nm and 900 nm, rises sharply after 920 nm and peaks at 980 nm. An oxyhemoglobin absorption spectrum 112 increases slowly with wavelengths starting from 700 nm and reaches a maximum at about 900 nm. A deoxyhemoglobin absorption spectrum 114 has a peak at 760 nm and then decreases until 900 nm. The absorption coefficients of oxyhemoglobin and deoxyhemoglobin are equal (an isobestic point) at 800 nm.

To visualize the differences of oxygenation status between cancerous tissue and normal tissue, in this embodiment, the tissue is illuminated with near infrared radiation, as discussed in greater detail below in the context of the electromagnetic radiation provider 53. Two distinct NIR wavelength bands are selected for NIR reflectance imaging of the tissue: a first NIR wavelength band 116 from 750 nm to 800 nm, where deoxyhemoglobin absorption is higher than that of oxyhemoglobin, and a second NIR wavelength band 118 from 800 nm to 900 nm, where oxyhemoglobin absorption is higher than that of deoxyhemoglobin. Water absorption is almost constant across the first and second NIR wavelength bands 116 and 118. Cancerous tissue contains more deoxyhemoglobin than oxyhemoglobin as compared to normal tissue due to hypoxia, therefore, in an image of the tissue in the first NIR wavelength band 116, cancerous tissue appears darker than normal tissue. In contrast, in an image of the tissue in the second NIR wavelength band 118, cancerous tissue appears brighter than normal tissue.

The present embodiment of the invention allows such images of the tissue to be produced. More particularly, due to the configuration of the CCD camera 50, the radiation direction system 80 and the BP filters 106 and 108, the CCD camera 50 acts as an apparatus for detecting tissue oxygenation status, the apparatus including a first detector (i.e. the third detector 88) operable to produce a first signal in response to radiation reflected by tissue in the first NIR wavelength band 116, and a second detector (i.e. the fourth detector 89) operable to produce a second signal in response to radiation reflected by the tissue in the second near infrared wavelength band 118, which is selected such that a ratio of an absorption coefficient of oxyhemoglobin to an absorption coefficient of deoxyhemoglobin in the second wavelength band is different than the ratio in the first wavelength band, the first and second signals being operable for use in producing an oxygenation image of the tissue.

These signals may then be combined, by using the signals produced by the third detector 88 to produce a green image of the tissue, and using the signals produced by the fourth detector 89 to produce a red image superimposed on the green image, for example. Such a combination distinguishes cancerous tissue from normal tissue quite clearly, as the normal tissues will tend to appear bright green while the cancerous tissues tend to appear bright red.

Alternatively, other ways of combining the reflectance information of the tissue in the first and second NIR wavelength bands may be substituted. In addition, although the above-noted selection of the first and second NIR wavelength bands serves to produce an optimal distinction between cancerous and normal tissues, alternatively, any other two suitable near infrared wavelength bands may be substituted, provided the ratio of the absorption coefficient of oxyhemoglobin to deoxyhemoglobin in one band is different from that in the other. Preferably, the absorption coefficient of water should be roughly equal in the two NIR wavelength bands, in order to avoid significant measurement errors resulting from absorption of chromophores other than oxyhemoglobin and deoxyhemoglobin.

Although it would be possible to observe reflectance of the tissue in only one near infrared wavelength band rather than two, this would not be desirable, as the second near infrared wavelength band in the present embodiment allows for normalization or correction for geometrical factors.

For example, there are at least two alternative reasons why a given point in the tissue may appear dark in the first NIR wavelength band. On the one hand, the tissue may be diseased or abnormal at that point and may therefore exhibit hypoxia. On the other hand, however, the tissue may be normal, but may simply be further away from the tip of the endoscope than other points in the tissue, or alternatively light from that point in the tissue may be reduced by partial obstruction or other geometrical factors, such as curved tissue surfaces, folds, polyps, or the angle of the endoscope relative to the tissue surface, for example. It is not possible to determine the cause of such a dark region from the reflectance intensity of the region in a single wavelength band.

However, although abnormal or diseased tissue has a lower reflectance than normal tissue in the first NIR wavelength band 116, such diseased tissue will have a higher reflectance than normal tissue in the second NIR wavelength band 118. Thus, in order to produce a normalized oxygenation image to correct for geometrical factors, in the present embodiment, the tissue is simultaneously observed by the third and fourth detectors 88 and 89 in the first and second NIR wavelength bands 116 and 118 respectively. In the previous example, where the signals produced by the third detector 88 are used to produce a green image and the signals produced by the fourth detector 89 are used to produce a red image, any normal tissue that appears dark in the green image only because of geometrical factors will also appear dark in the red image, as geometrical factors are typically wavelength-independent. However, tissue that appears dark in the green image because it is cancerous will appear bright in the red image due to the hypoxia of the cancerous tissue and the lower absorption coefficient of deoxyhemoglobin in the second NIR wavelength band.

In addition to the utility of the third and fourth detectors in the NIR reflectance imaging modality described above, these detectors also allow for improvements in the fluorescence imaging modality. More particularly, a fluorescence image may be normalized or corrected for geometrical factors using NIR reflectance images, which are better-suited for this purpose than the visible red light reflectance images previously used by the present inventors to normalize fluorescence images, due to the greater similarity of reflectances of normal and diseased tissues at NIR wavelengths as compared to visible wavelengths.

The conceptual basis for normalization of the fluorescence image is similar to that described above in connection with the NIR reflectance modality. Abnormal or diseased tissue fluoresces with significantly lower intensity than normal tissue and therefore, diseased tissue appears dark in a fluorescence image. Normal tissue may also appear dark in a fluorescence image due to geometrical factors. However, diseased tissue will reflect NIR radiation at intensities somewhat similar to those of normal tissue, as the differences between the NIR reflectance intensities of normal and abnormal tissues are much smaller than the differences between the fluorescence emission intensities of normal and abnormal tissues. Thus, in order to normalize the fluorescence image to correct for geometrical factors, in the present embodiment, the tissue is simultaneously illuminated with blue light to induce fluorescence in the tissue, and with near infrared radiation longer than 750 nm to produce an NIR reflectance image of the tissue. The production of such illuminating radiation is discussed in further detail below in the context of the electromagnetic radiation provider 53.

Referring back to FIG. 4, the configuration of the CCD camera 50, the radiation direction system 80 and the filters 104, 106 and 108 allow radiation fluorescently emitted by the tissue to be received at the second detector 87, while NIR radiation reflected by the tissue between 750 and 800 nm is received at the third detector 88, and NIR radiation reflected by the tissue between 800 and 900 nm is received at the fourth detector 89. The signals produced by the fourth detector 89 may then be used to generate a visible red image of the tissue on a display screen. The signals produced by the second detector 87 may be used to simultaneously generate a green fluorescence image superimposed over the red reflectance image. Thus, if a given point is dark in the fluorescence image simply because it is farther away from the endoscope tip or due to other geometrical factors, then that point also appears dark in the NIR reflectance image, and therefore appears dark in the superposition of the two green and red images. However, if a given point in the tissue appears dark in the fluorescence image because it is abnormal or diseased, then that point is likely to appear bright in the NIR reflectance image, and therefore appears as a red spot in the superposed image.

Alternatively, the signals produced by the third detector 88 may be used to normalize the fluorescence image, although the signals produced by the fourth detector 89 are preferred as the intensity changing trends from normal tissue to cancerous tissue for the fluorescence and NIR reflectance images are in the opposite direction if the signals produced by the fourth detector are used: as tissue changes from normal to diseased tissue, its fluorescence decreases, while its reflectance in the second NIR wavelength band 118 increases. Therefore, for normalization purposes, the signals produced by the fourth detector 89 provide better contrast between cancerous tissue and normal tissue than the signals produced by the third detector 88 in response to reflectance by the tissue in the first NIR wavelength band, in which the transition from normal to diseased tissue is in the same direction (decreasing in intensity) as fluorescence.

Figure 7:
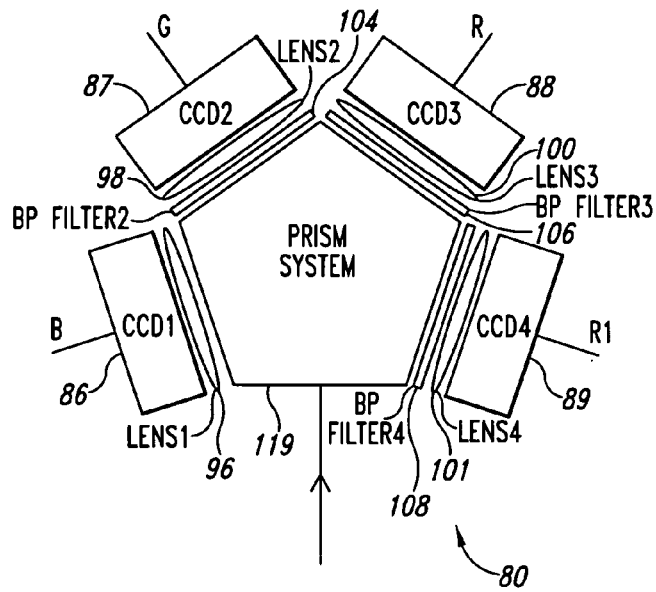
FIG. 7 is a schematic representation of an imaging device of the system shown in FIG. 2, having a radiation direction system according to a third embodiment of the invention.

Referring to FIG. 7, in an alternative embodiment of the invention, the radiation direction system 80 may include a prism system 119 configured to direct the respective wavelength ranges of the incident radiation, i.e. the second group 56 of rays, onto the respective corresponding detector areas. As in the embodiment shown in FIG. 4, BP filters 104, 106 and 108 are preferably placed in front of corresponding detectors 87, 88 and 89 for optimal fluorescence and NIR reflectance detection.

Diagnostic Sensitivity Adjustment

Referring back to FIGS. 2 and 4, an apparatus for producing a high diagnostic sensitivity image while achieving high diagnostic specificity with spectroscopy is shown generally at 120 in FIG. 2. In this embodiment the apparatus 120 includes the CCD camera 50. The apparatus 120 includes at least two detectors for receiving radiation in respective wavelength ranges. More particularly, the apparatus includes the first, second, third and fourth detectors 86, 87, 88 and 89 for receiving radiation in four respective wavelength ranges, namely, blue (B), green (G), red/NIR (R) and NIR (R1) respectively, as described above.

At least one of the detectors has a selectively adjustable gain adjustable to produce an optimized image of the object 63 in response to input radiation. More particularly, in this embodiment each of the individual detectors 86, 87, 88 and 89 has an adjustable gain, adjustable to produce an optimized image of tissue observed by the endoscope 59 in response to the electromagnetic radiation beam 58 received from the endoscope.

In this embodiment, the apparatus 120 further includes the housing 62 containing the detectors 86, 87, 88 and 89 and having the first measurement port 70 for providing at least some of the input radiation to the spectrometer 48 to facilitate measurement of a spectrum of the input radiation from a point in an area of the object 63, i.e. the tissue, appearing in the optimized image.

In the present embodiment, the processor circuit 41 shown in FIG. 2 is programmed or configured to control the camera controlling electronics 49 to selectively adjust the diagnostic sensitivity, which in this embodiment is achieved by adjusting the gain, in at least one of the detectors 86, 87, 88 and 89 relative to the gain of at least one other of the detectors 86, 87, 88 and 89 to produce the improved image of the object.

More particularly, in this embodiment the processor circuit 41 is configured to selectively adjust at least one of a near infrared (NIR) wavelength range gain and a green wavelength range gain to produce a desired NIR-to-green gain ratio, and therefore, a desired NIR-to-green signal ratio for fluorescence imaging of the object 63 at a desired diagnostic sensitivity.

Such selective diagnostic sensitivity adjustment is particularly advantageous where the tissue is illuminated with an excitation and a NIR component, as described in greater detail below, in connection with the electromagnetic radiation provider 53. In existing systems, the green gain is set relatively high for fluorescence imaging, as the intensity of radiation fluorescently emitted by the tissue is typically low. If the red-to-green gain ratio, and therefore, the red-to-green signal ratio is too low, then potentially diseased areas might appear dark rather than red in the superposed image, resulting in undesirable "false negative" diagnoses. Conversely, in existing systems it has been viewed as desirable to prevent the red-to-green gain ratio, and therefore, the red-to-green signal ratio, from being too high, to prevent normal tissues from appearing red rather than green, which would result in too many "false positive" diagnoses. However, the present embodiment of the invention effectively removes this limitation, by providing some of the electromagnetic radiation beam 58 to the spectrometer 48 via the first measurement port 70, in order to use simultaneous fluorescence spectroscopy to achieve higher diagnostic specificity. Therefore, a broader range of relative gain relationships of the second, third and fourth detectors 87, 88 and 89 is available in the present embodiment of the invention than would have been previously possible.

Thus, in this embodiment, in which the signal from the fourth detector 89 is used to normalize the fluorescence image, the processor circuit 41 is configured to selectively adjust the gains of the second or green detector 87 and the fourth detector 89 to pre-defined levels in order to produce an improved fluorescence image of the tissue. It will be appreciated that these pre-defined levels will depend to varying extents on the particular characteristics of the detectors 86, 87, 88 and 89, of the electromagnetic radiation provider 53 and of the endoscope 59, and therefore will vary from system to system. These pre-defined levels are determined empirically in each such system by performing a statistically significant number of imaging and spectroscopy tests with varying gain ratios and confirming the results of each test with biopsy test results, in order to arrive at the improved diagnostic sensitivity levels for the particular system. Alternatively, if desired, pre-defined gain levels for a "typical" system may be stored by the manufacturer of the apparatus 120 in a computer-readable storage medium readable by the processor circuit 41, thereby removing the need to perform such empirical tests, although such "typical" pre-defined levels will not necessarily take into account the unique characteristics of the particular system.

Similarly, in this embodiment the processor circuit 41 is also configured to selectively adjust red, green and blue wavelength range gains to produce a desired color balance for white light reflectance imaging of the object. Once again, such gains may be set to pre-defined levels, which may be obtained by empirical testing of the particular system or which may alternatively be stored on a computer-readable storage medium based on previous testing of a typical system.

In this embodiment the apparatus 120 is used for fluorescence imaging, white light reflectance imaging and NIR reflectance imaging. Therefore, in this embodiment the processor circuit 41 is configured to set the gains in the at least one of the detectors and in the at least one other of the detectors to a first set of gain levels to enhance display of abnormal areas of the object in a fluorescence image of the object, and is configured to set the gains to a second set of gain levels to enhance display of the abnormal areas of the object in a white light reflectance image of the object. In the present embodiment, fluorescence imaging and NIR reflectance imaging may be performed simultaneously, and therefore the gain levels for fluorescence imaging may also be used for NIR reflectance imaging. Alternatively, however, the processor circuit may be configured to set the gains to a third set of gain levels to enhance display of the abnormal areas of the object in a NIR reflectance image of the object.

Spectrometer

Figure 8:
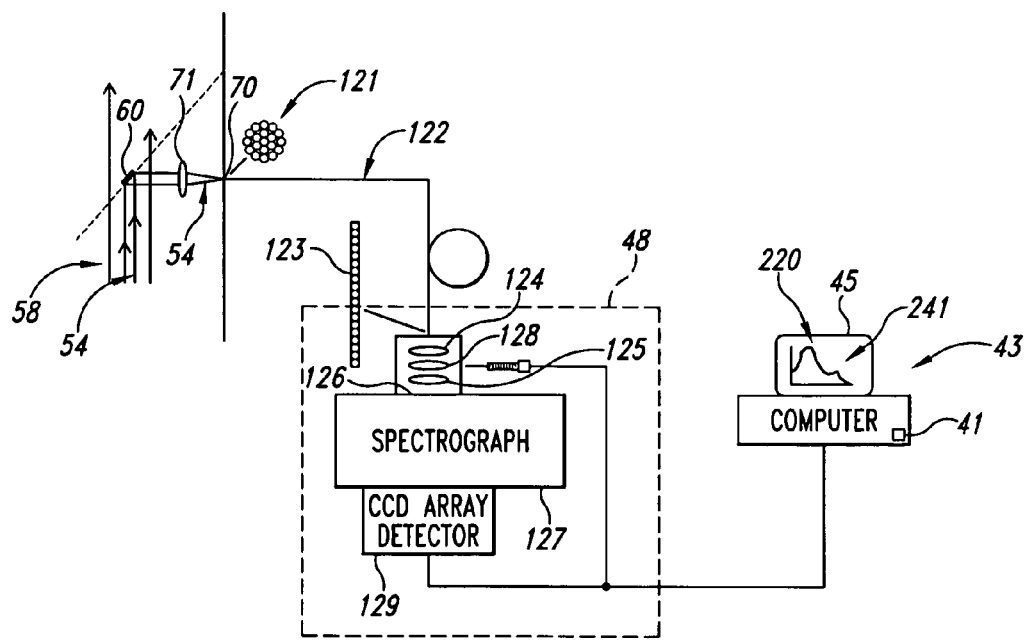
FIG. 8 is a schematic representation of a spectrometer of the system shown in FIG. 2.

Referring to FIGS. 2 and 8, the spectrometer is shown generally at 48 in FIG. 8. As described above in connection with FIGS. 2 and 3, the first group 54 of rays of the electromagnetic radiation beam 58 is directed by the reflective surface 60 and lens 71 to the first measurement port 70. In this embodiment, a first open end 121 of an optical fiber bundle 122 is connected to the first measurement port 70 for providing the first group 54 of rays to the spectrometer 48. In the present embodiment the optical fibers at the first open end 121 of the optical fiber bundle 122 are arranged in a circular configuration, to correspond to the shape of the reflective surface 60 as imaged onto the first measurement port 70 by the lens 71. However, at a second open end 123 of the optical fiber bundle 122 which is connected to the spectrometer 48, the individual optical fibers are rearranged into a linear configuration.

In this embodiment, the linear second open end 123 of the optical fiber bundle enters the spectrometer 48 and projects light received from the first measurement port 70 onto first and second lenses 124 and 125, which image the linear second open end 123 onto an entrance slit 126 of a spectrograph 127. In addition, a filter 128 is removably interposed between the two lenses 124 and 125. In this embodiment the filter 128 is a longpass (LP) filter passing electromagnetic radiation longer than 475 nm and having negligible transmission characteristics at shorter wavelengths. More particularly, in this embodiment the filter 128 is a GG475 Schott glass filter, although alternatively, other suitable filters may be substituted.

The filter 128 is interposed between the two lenses during fluorescence/NIR reflectance imaging of the object 63 with the endoscope 59, to block reflections of the short-wavelength excitation radiation used to induce fluorescence in the object. For white light reflectance imaging of the object, the filter 128 is removed from its position between the two lenses. To achieve this, the filter 128 includes a solenoid switch and a control device in communication with the processor circuit 41 of the computer 43, which is programmed to control the solenoid switch to insert the filter 128 between the lenses 124 and 125 for fluorescence/NIR reflectance spectroscopy and to remove it for visible reflectance spectroscopy. Alternatively, other means of moving the filter 128 may be substituted, or alternatively the filter 128 may be omitted if only visible reflectance spectroscopy is desired, or permanently fixed if only fluorescence/NIR reflectance spectroscopy is desired.

The spectrograph 127 is in communication with a CCD array detector 129 for producing an image representing intensity at each wavelength received by the spectrometer 48. The CCD array detector 129 captures a spectrum image from the spectrograph 127, and vertically bins the image to provide a high signal to noise ratio spectrum. The CCD array detector 129 is in communication with the processor circuit 41 of the computer 43, which is programmed to display the spectrum in real time on the monitor 45.

Electromagnetic Radiation Provider

Figure 9:
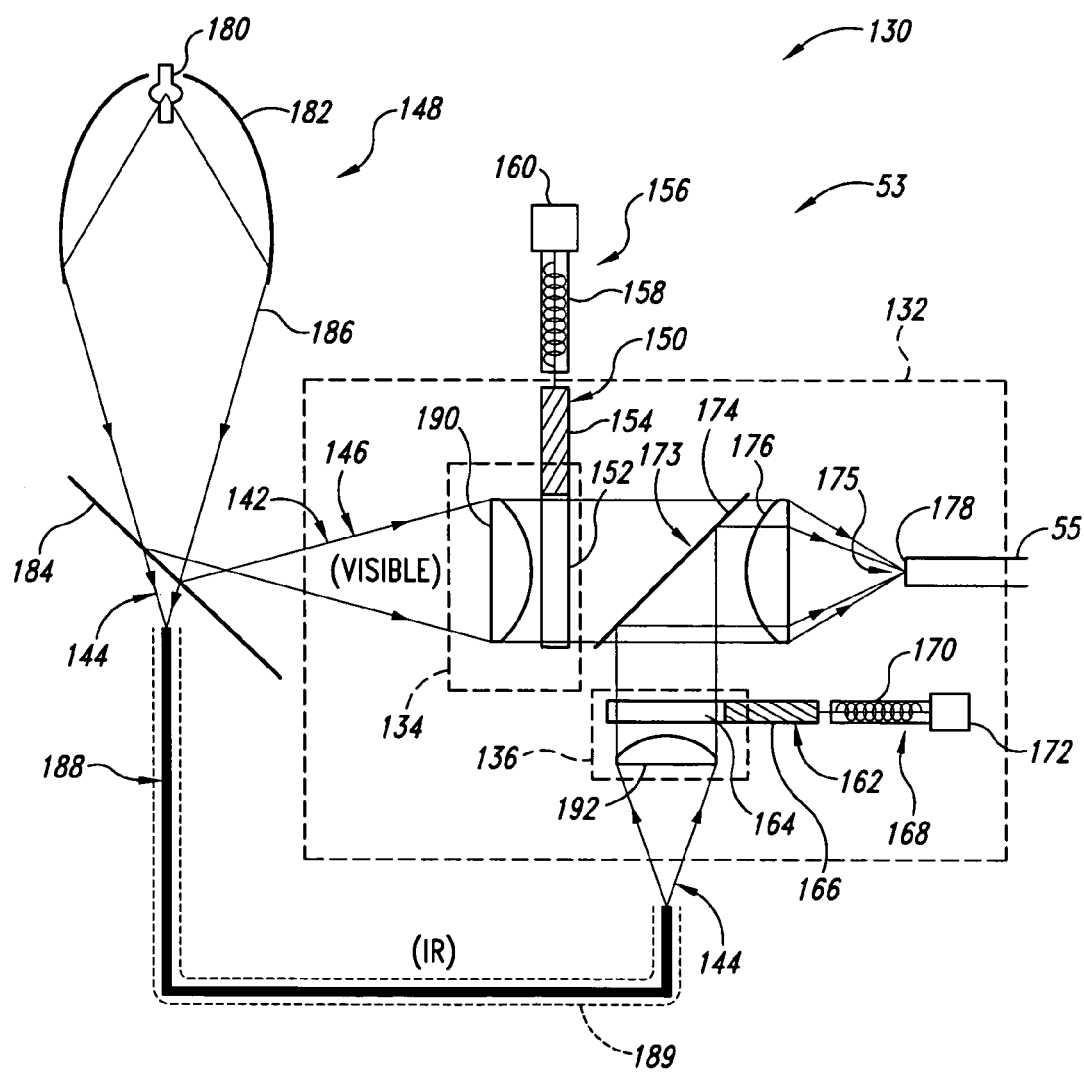
FIG. 9 is a schematic representation of an apparatus shown in FIG. 2 for producing illuminating radiation for fluorescence and reflectance imaging, according to a fourth embodiment of the invention.

Referring to FIGS. 2, 9, 10 and 11, an apparatus for producing illuminating radiation for fluorescence and reflectance imaging is shown generally at 130 in FIG. 9. In this embodiment the apparatus 130 includes the electromagnetic radiation provider 53 shown in FIG. 2. The electromagnetic radiation provider 53 includes an optical system shown generally at 132 in FIG. 9, which includes first and second optical subsystems 134 and 136, operable to selectively produce first and second spectral distributions such as those shown generally at 138 in FIG. 10 and at 140 in FIG. 11 for example, for fluorescence/NIR reflectance imaging and white light reflectance imaging respectively. The first spectral distribution 138 shown in FIG. 10 includes an excitation component 142 received from the first optical subsystem 134, and a NIR component 144 received from the second optical subsystem 136. The second spectral distribution 140 shown in FIG. 11 includes a white light illumination component 146 received from the first optical subsystem 134.

Although an excitation component alone would suffice for basic fluorescence imaging, it has been found that using only a single short-wavelength excitation waveband is disadvantageous, as it fails to account for the geometry of the tissue being imaged. Thus, in the present embodiment, to correct for geometrical factors as discussed above in the context of the CCD camera 50, for fluorescence imaging, the tissue is simultaneously irradiated with the excitation component 142 and the NIR component 144 shown in FIG. 10. More particularly, in this embodiment the NIR component 144 includes radiation in a NIR reflectance waveband between 750 nm and 900 nm. This additional reflectance waveband may be used to illuminate the tissue to produce two NIR reflectance images (in the first and second NIR wavelength bands 116 and 118, between 750 nm and 800 nm and between 800 nm and 900 nm respectively) of the tissue, simultaneously with producing the fluorescence image of the tissue. One of the NIR reflectance images may then be used to correct or normalize the fluorescence image for the geometry of the tissue. The two NIR images may also be used to display a NIR reflectance image representing tissue oxygenation status, for further improvement in diagnostic accuracy, as discussed in greater detail above.

The present embodiment of the invention provides greater flexibility than previously existing systems, by virtue of the first and second optical subsystems. For example, in the present embodiment the use of the NIR component 144 to normalize a fluorescence image provides enhanced correction for geometric factors compared to systems employing visible red normalization components, due to the greater similarity of the reflectance spectra in NIR wavelength ranges of normal and abnormal tissues than at shorter visible red wavelengths. Also, the use of NIR radiation longer than 750 nm as the NIR component 144 allows for a full wavelength range fluorescence spectrum ranging from 450 nm to 750 nm to be measured. Additionally, in the present embodiment, because the NIR component 144 is received from the second optical subsystem 136, the NIR component 144 does not travel through the first optical subsystem 134, thereby preventing unnecessary heating damage to components of the first optical subsystem. Alternatively, the use of first and second optical subsystems allows for greater flexibility in selecting other wavelength ranges for the excitation and normalization components, which, in contrast with previously existing systems, do not have to be provided using a single optical filter.

In addition, because the first and second optical subsystems 134 and 136 are provided in a single optical system 132, fluorescence and reflectance imaging may be achieved without the need to manually disconnect one light source and connect another to the endoscope 59.

Figure 10:
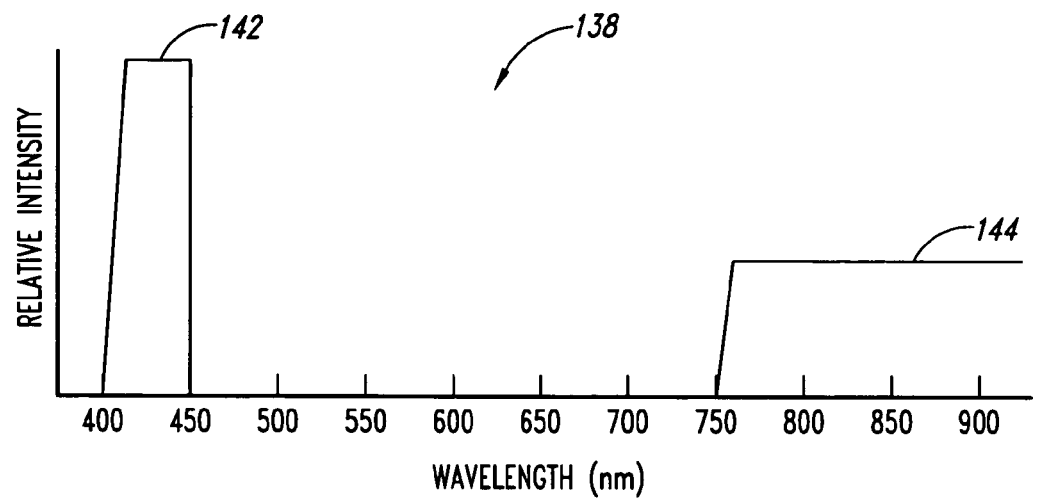
FIG. 10 is a graphical representation of a first spectral distribution for fluorescence/NIR reflectance imaging, produced by the apparatus shown in FIG. 9.
Figure 11:
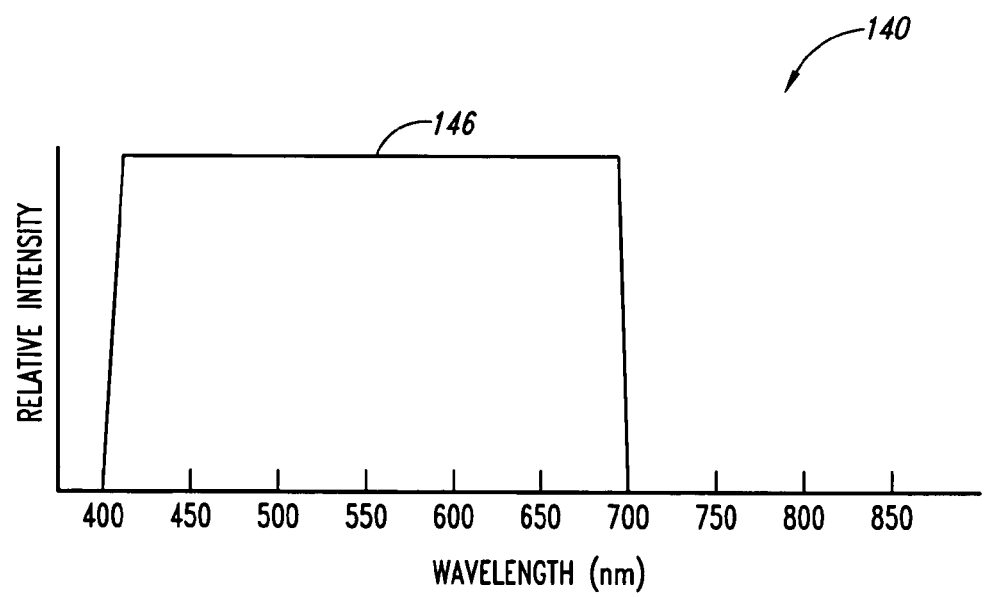
FIG. 11 is a graphical representation of a second spectral distribution for white light reflectance imaging, produced by the apparatus shown in FIG. 9.

Referring to FIGS. 9, 10 and 11, in this embodiment, the first optical subsystem 134 is operable to receive the white light illumination component 146 and the excitation component 142. The first optical subsystem 134 is operable to transmit the excitation component 142 in a first operational mode for fluorescence imaging, and to transmit the white light illumination component 146 in a second operational mode for white light reflectance imaging.

Similarly, the second optical subsystem 136 is operable to receive the NIR component 144. The second optical subsystem 136 is operable to transmit the NIR component in the first operational mode and to block the NIR component in the second operational mode.

Generally, in the present embodiment the optical system 132 includes a filter system. More particularly, in this embodiment the first optical subsystem 134 includes a filtering device 150 operable to transmit the excitation component 142 while attenuating other wavelengths in the first operational mode. The filtering device 150 is operable to transmit the white light illumination component 146 in the second operational mode. More particularly, in this embodiment the filtering device 150 includes two interchangeable filters, namely, a blue bandpass (BP) filter 152 for transmitting the excitation component 142 in the first operational mode, and a color balance filter 154 interchangeable with the blue BP filter, for transmitting the white light illumination component in the second operational mode.

More particularly, in the first operational mode, the blue BP filter 152 is placed in the path of the radiation received by the first optical subsystem. In this embodiment, the blue BP filter 152 passes electromagnetic radiation wavelengths between 400 nm and 450 nm, to provide the excitation component 142. The blue BP filter 152 has negligible out-of-band transmission characteristics, transmitting less than one part in $10^5$ of electromagnetic radiation outside the 400 to 450 nm wavelength band. This blue transmission band has been found to be suitable for exciting fluorescence emission in tissues, and unlike ultraviolet radiation for example, does not cause appreciable damage to the irradiated tissues. Alternatively, however, other transmission wavebands and out-of-band transmission characteristics may be selected if desired. Thus, in the first operational mode, the filter 152 ensures that the first optical subsystem 134 transmits only the excitation component 142 of the radiation received by the first optical subsystem.

In the second operational mode, the color balance filter 154 is placed in the path of the radiation received by the first optical subsystem 134. In this embodiment, the color balance filter is designed to transmit, as the white light illumination component 146, a flat spectral distribution of visible light ranging from 400 nm to 700 nm, to provide the second spectral distribution 140 for illuminating the tissue for white light reflectance imaging. The color balance filter 154 has negligible out-of-band transmission characteristics. It will be appreciated that in order to ensure this flat spectral output, the color balance filter 154 is designed to compensate for the particular spectrum of the radiation received by the first optical subsystem 134, which in turn depends on the particular source 148 that is employed. Alternatively, other types of color balance filters may be substituted to provide the second spectral distribution for illumination of the tissue for white light reflectance imaging. Or, as a further alternative, the color balance filter may be omitted entirely if the spectral distribution of the input radiation received by the first optical subsystem is already suitable for white light reflectance imaging of the tissue.

Referring to FIG. 9, in this embodiment, the second optical subsystem 136 includes a filtering device shown generally at 162 operable to transmit the NIR component 144 while attenuating other wavelengths in the first operational mode. The filtering device 162 is operable to block the NIR component in the second operational mode.

More particularly, in this embodiment the filtering device 162 includes two interchangeable filters, namely, a NIR longpass (LP) filter 164 for transmitting the NIR component 144 in the first operational mode, and a light stopper 166 interchangeable with the LP filter, for blocking the NIR component in the second operational mode.

In the first operational mode, the NIR LP filter 164 is placed in the path of input radiation received by the second optical subsystem 136. The NIR LP filter transmits wavelengths longer than 750 nm, and has negligible transmission characteristics at shorter wavelengths. Alternatively, other types of filter, such as a NIR BP filter for example, may be substituted in the first operational mode if desired.

In the second operational mode, the light stopper 166 is placed in the path of the input radiation received by the second optical subsystem 136. The light stopper effectively blocks all wavelengths received by the second optical subsystem 136. Alternatively, other types of light stoppers or filters may be substituted for this purpose.

Referring to FIGS. 2 and 9, in order to switch between the first and second operational modes referred to above, the processor circuit 41 is in communication with first and second switching devices shown generally at 156 and 168 respectively in FIG. 9. The processor circuit 41 is programmed to control the first switching device 156 to interchange the blue bandpass filter 152 and the color balance filter 154 in the path of the input radiation received by the first optical subsystem 134. Similarly, the processor circuit is programmed to control the second switching device 168 to interchange the NIR LP filter 164 and the light stopper 166 in the path of the input radiation received by the second optical subsystem 136. The first and second switching devices may include solenoid switches 158 and 170 respectively, and control devices 160 and 172 for actuating the solenoid switches 158 and 170 respectively. Alternatively, other types of switching devices may be substituted.

Still referring to FIGS. 2 and 9, in this embodiment the optical system 132 further includes a combiner shown generally at 173, locatable to direct radiation transmitted by the first and second optical subsystems 134 and 136 along a common optical path 175.

More particularly, in this embodiment the combiner 173 includes a dichroic reflecting device 174 locatable to transmit radiation transmitted by the first optical subsystem 134 along the path and to reflect radiation transmitted by the second optical subsystem 136 along the path. In the present embodiment, the dichroic reflecting device transmits electromagnetic radiation shorter than 750 nm, but reflects radiation longer than 750 nm. The dichroic reflecting device thus transmits visible wavelengths received from the first optical subsystem 134 along the path 175, and reflects NIR wavelengths received from the second optical subsystem 136 along the path.

The optical system 132 also includes a lens 176 locatable in the optical path 175, to focus the radiation transmitted by the first and second optical subsystems 134 and 136 onto an exit port 178. More particularly, in this embodiment the exit port 178 includes an open end of the optical fiber bundle 55 shown in FIG. 2, in order to transmit radiation passed by the first optical subsystem 134 and the second optical subsystem 136 through the endoscope 59 to the object 63.

Referring to FIG. 9, the apparatus 130 further includes at least one electromagnetic radiation source, shown generally at 148, for providing the white light illumination component 146 and the excitation component 142 to the first optical subsystem 134, and for providing the NIR component 144 to the second optical subsystem 136.

More particularly, in this embodiment the electromagnetic radiation source 148 includes a lamp 180, which in this embodiment is a 100 W mercury arc lamp, model 6281 from Oriel Instruments, Stratford, Conn., USA, having an arc size of approximately 0.25 mm. Alternatively, a xenon arc lamp, a metal halide lamp or any other suitable lamp or other radiation source may be substituted, although it is preferable that a single source be able to provide all necessary illumination for both reflectance and fluorescence imaging. If an arc lamp is used, then preferably it has a small arc size, such as the 0.25 mm arc size of the lamp 180 in the present embodiment, as such a small arc size facilitates ultimate focusing of the light onto a small fiber bundle. Alternatively, the lamp may be omitted entirely, and the apparatus 130 may simply provide an optical system for spectral modification of existing light sources, although it is preferable that the color balance filter 154, if provided, be designed to correspond to the particular type of lamp used. As a further alternative, the at least one electromagnetic radiation source may include two or more electromagnetic radiation sources.

In this embodiment the electromagnetic radiation source 148 further includes an elliptical reflector 182. The lamp 180 is positioned at a focal point of the elliptical reflector 182.

Referring to FIGS. 9, 10 and 11, the electromagnetic radiation source 148 further includes a beam splitter 184 operable to receive input electromagnetic radiation, to reflect the white light illumination component 146 and the excitation component 142 for receipt by the first optical subsystem 134 and to transmit the NIR component 144 for receipt by the second optical subsystem 136. Thus, in this embodiment the lamp 180 is operable to provide the input electromagnetic radiation to the beam splitter 184. Either the lamp 180, or the beam splitter 184, or both, may be viewed as examples of an electromagnetic radiation source locatable to produce the input electromagnetic radiation for receipt by the optical system 132.

More particularly, the beam splitter 184 receives the input electromagnetic radiation from the lamp 180 and the elliptical reflector 182. In this embodiment the beam splitter includes a cold mirror, which reflects visible light but transmits near infrared radiation. The beam splitter 184 is positioned to reflect visible light, which includes both the white light illumination component 146 shown in FIG. 11 and the excitation component 142 shown in FIG. 10, for receipt by the first optical subsystem 134.

The beam splitter 184 transmits near infrared and longer wavelengths of the input radiation, which include the NIR component 144 shown in FIG. 10, for receipt by the second optical subsystem 136. More particularly, in this embodiment the optical system 132 includes a redirecting device 188 locatable to receive the NIR component 144 from the beam splitter 184, and to redirect the NIR component to the second optical subsystem 136. In this embodiment the redirecting device 188 includes an optical fiber bundle. Alternatively the redirecting device 188 may include a liquid light guide such as that shown in broken outline at 189, or any other suitable redirecting device.

The optical system 132 may further include various additional optical elements, if desired. For example, in this embodiment the first optical subsystem 134 includes a lens 190, or more particularly a plano-convex lens, for collimating the input radiation received from the beam splitter 184 through the filtering device 150 toward the dichroic reflecting device 174 and lens 176. Similarly, the second optical subsystem 136 includes a lens 192 for collimating the input radiation received from the redirecting device 188 through the filtering device 162 toward the dichroic reflecting device 174.

Thus, referring to FIGS. 9, 10 and 11, in this embodiment the optical system 132 is operable to produce, as the excitation component 142, radiation having blue and shorter wavelengths. The optical system is therefore operable to produce, as the excitation component, a short wavelength component sufficiently short to cause fluorescence in the object 63, which in this embodiment is tissue. Likewise, the optical system is operable to produce, as the NIR component 144, a long wavelength component longer than fluorescent emission wavelengths of the object. In this embodiment the fluorescent emission wavelengths typically include wavelengths from 450 nm to 750 nm, and thus, in the present embodiment the NIR component is produced at wavelengths of 750 nm and longer.

As shown in FIG. 10, the optical system 132 is operable to produce the first spectral distribution 138 to have an intensity at the fluorescent emission wavelengths sufficiently below an intensity of fluorescent radiation emitted by the object, i.e. tissue, in response to the short wavelength component, to permit detection of the fluorescent radiation. More particularly, in this embodiment the first spectral distribution has negligible intensity at fluorescent emission wavelengths, and more particularly, has negligible intensity between 450 and 750 nm. This facilitates full wavelength range fluorescence spectral measurement of the tissue, as the negligible illumination intensity at fluorescent emission wavelengths results in negligible measurement errors caused by reflectances at these wavelengths.

Thus, as shown in FIG. 10, in this embodiment the first spectral distribution consists essentially of the short and long wavelength components, the short wavelength component consisting essentially of radiation having wavelengths between about $4\frac{1}{2} \times 10^2$ nm and about $4 \times 10^2$ nm, and the long wavelength component consisting essentially of radiation having wavelengths between about $7\frac{1}{2} \times 10^2$ nm and at least about $9 \times 10^2$ nm. Therefore, in this embodiment, the negligible intensity of the first spectral distribution 138 at the green and red fluorescent emission wavelengths prevents reflections by the tissue at these wavelengths which would introduce measurement errors into measurements of the intensity of fluorescence of the tissue.

Similarly, referring to FIGS. 9 and 11, the optical system 132 is operable to produce, as the white light illumination component 146, visible light.

Operation

Figure 12:
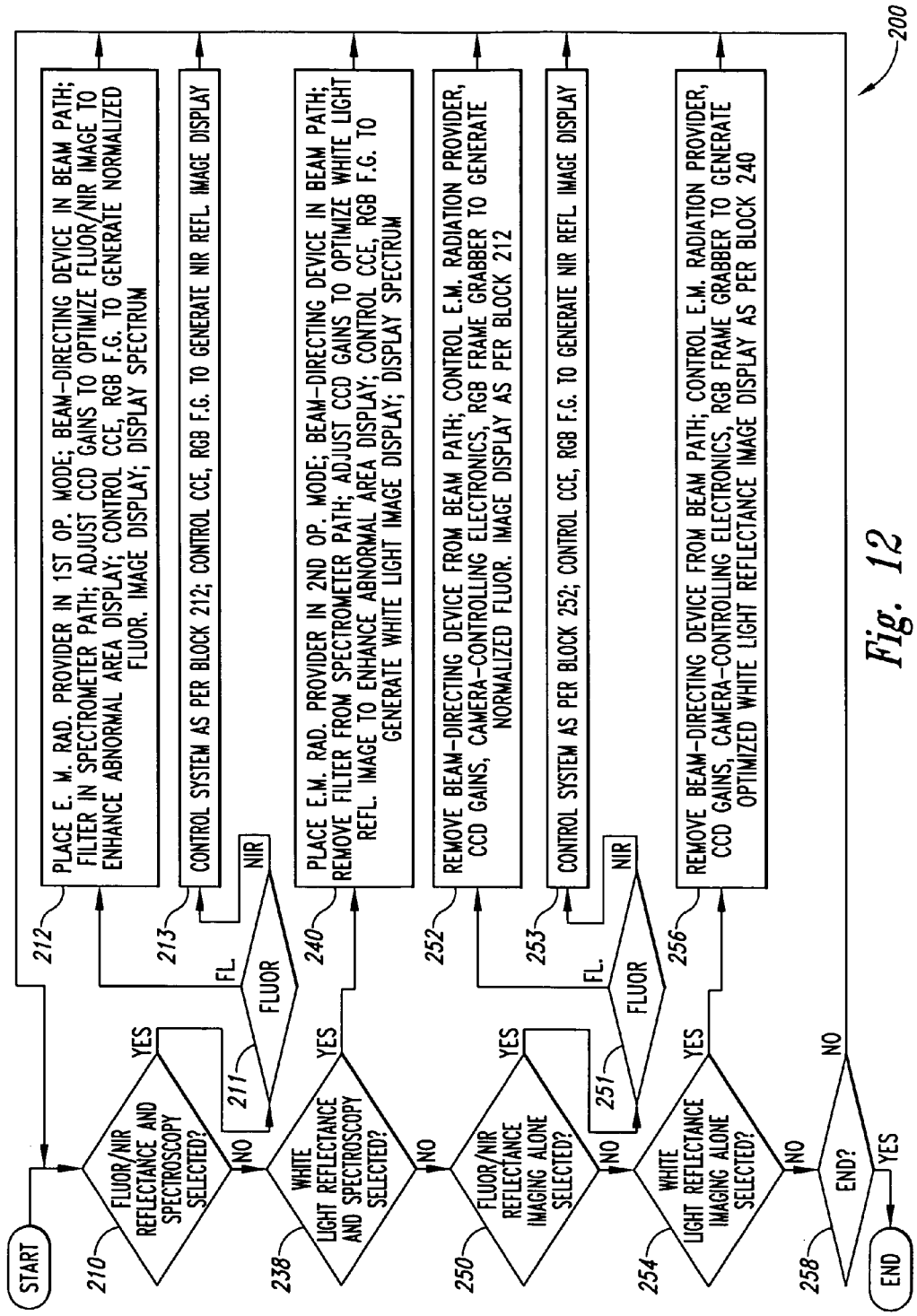
FIG. 12 is a flowchart of a measurement routine executed by a processor circuit of the system shown in FIG. 2.

Referring to FIGS. 2 and 12, a measurement routine executed by the processor circuit 41 is shown generally at 200 in FIG. 12. In this embodiment, the measurement routine 200 is stored on a computer-readable storage medium 202 shown in FIG. 2 accessible by the processor circuit 41, such as a hard disk drive or a compact disc, for example. Alternatively, any other suitable media, or any alternative methods or structures for generating a signal embodied in a carrier wave comprising code segments for directing a processor circuit to perform equivalent functions to those described herein may be substituted.

In this embodiment, the measurement routine 200 includes various blocks of instructions codes which configure the processor circuit 41 to communicate with the first and second measuring devices 44 and 46 and the electromagnetic radiation provider 53 shown in FIG. 2, to control such devices to perform fluorescence and reflectance imaging and spectroscopy. The measurement routine 200 is executed upon receiving user input at the computer 43 shown in FIG. 2, at a user input device 204, which in this embodiment is a keyboard. Alternatively, other user input devices may be substituted.

Generally, the measurement routine 200 configures or programs the processor circuit 41 to control the beam-directing device 52 to cause the first and second adjacent groups 54 and 56 of rays of the electromagnetic radiation beam 58 to be directed for receipt by the first and second measuring devices 44 and 46 respectively. The measurement routine also configures the processor circuit to control the electromagnetic radiation provider 53 to selectively produce the first and second spectral distributions 138 and 140 of electromagnetic radiation for fluorescence/NIR reflectance imaging and white light reflectance imaging respectively, the first spectral distribution including the excitation component 142 received from the first optical subsystem 134 of the optical system 132 and the NIR component 144 received from the second optical subsystem 136 of the optical system, and the second spectral distribution including the white light illumination component 146 received from the first optical subsystem. In addition, the measurement routine configures the processor circuit to selectively adjust a gain of the imaging device, which in this embodiment is the CCD camera 50, in at least one wavelength range relative to the gain of the imaging device in at least one other wavelength range to produce an improved image of the object 63, and to measure a spectrum of radiation from a point in an area of the object appearing in the optimized image. The measurement routine further configures the processor circuit to control the electromagnetic radiation provider 53 and the CCD camera 50 to produce a first signal in response to radiation reflected by tissue in a first near infrared wavelength band, and to produce a second signal in response to radiation reflected by the tissue in a second near infrared wavelength band selected such that a ratio of an absorption coefficient of oxyhemoglobin to an absorption coefficient of deoxyhemoglobin in the second wavelength band is different than the ratio in the first wavelength band, the first and second signals being operable for use in producing an oxygenation image of the tissue.

The measurement routine 200 begins with a first block of codes shown at 210 in FIG. 12, which directs the processor circuit 41 to determine whether user input indicating a selection of a combined fluorescence/NIR reflectance imaging and spectroscopy mode has been received at the user input device 204.

If such user input has been received, block 211 directs the processor circuit 41 to determine whether the user input received at block 210 is indicative of a selection of simultaneous normalized fluorescence imaging and spectroscopy, or alternatively, a selection of simultaneous NIR reflectance imaging and spectroscopy. In this embodiment, the physical measurements for both fluorescence and NIR reflectance imaging are performed simultaneously in a single fluorescence/NIR reflectance imaging modality, although in the present embodiment the monitor 51 shown in FIG. 2 will display only one type of image (fluorescence or NIR reflectance) at any given time.

If at block 211 the user input indicates a selection of simultaneous normalized fluorescence imaging and spectroscopy, block 212 directs the processor circuit 41 to control the electromagnetic radiation provider 53, the CCD camera 50, the beam-directing device 52, and the spectrometer 48, as follows.

Referring to FIGS. 9, 10 and 12, block 212 first directs the processor circuit 41 to select and produce the first spectral distribution 138 for fluorescence/NIR reflectance imaging, the first spectral distribution 138 including the excitation component 142 received from the first optical subsystem 134 and the NIR component 144 received from the second optical subsystem 136. In this regard, block 212 directs the processor circuit to cause the first and second optical subsystems 134 and 136 shown in FIG. 9 to function in the first operational mode. More particularly, block 212 directs the processor circuit to activate the lamp 180, and to signal the control devices 160 and 172 to place the solenoid switches 158 and 170 respectively in retracted positions, such that the blue BP filter 152 is placed in the path of radiation passing through the first optical subsystem 134 and the NIR LP filter 164 is placed in the path of radiation passing through the second optical subsystem 136.

Thus, the beam splitter 184 receives input radiation including the excitation, NIR and white light illumination components, from the lamp 180. The beam splitter 184 provides visible light, and therefore provides the excitation and white light illumination components 142 and 146, to the first optical subsystem 134. The beam splitter provides near infrared radiation, and therefore provides the NIR component 144, to the second optical subsystem 136. The white light illumination and excitation components 146 and 142 are received from the beam splitter at the first optical subsystem 134, which transmits the excitation component 142, which in this embodiment is blue light between 400 and 450 nm, to the combiner 173. The NIR component 144 is received from the beam splitter, via the redirecting device 188, at the second optical subsystem 136, which transmits the NIR component 144, which in this embodiment is NIR radiation longer than 750 nm, to the combiner 173.

The combiner 173, which in this embodiment is the dichroic reflecting device 174, directs the radiation transmitted by the first and second optical subsystems along the common optical path 175. More particularly, the dichroic reflecting device 174 transmits the excitation component 142 received from the first optical subsystem 134, and reflects the NIR component 144 received from the second optical subsystem 136, along the common optical path 175, through the lens 176, to the exit port 178. Thus, in the first operational mode, the optical system 132 transmits the excitation component 142 from the first optical subsystem 134 and the NIR component 144 from the second optical subsystem 136.

Referring back to FIGS. 2 and 10, the excitation component 142 and the NIR component 144 of the first spectral distribution 138 are then conveyed from the exit port 178 to the endoscope 59 and ultimately to the tissue being imaged, via the optical fiber bundle 55.

Figure 13:
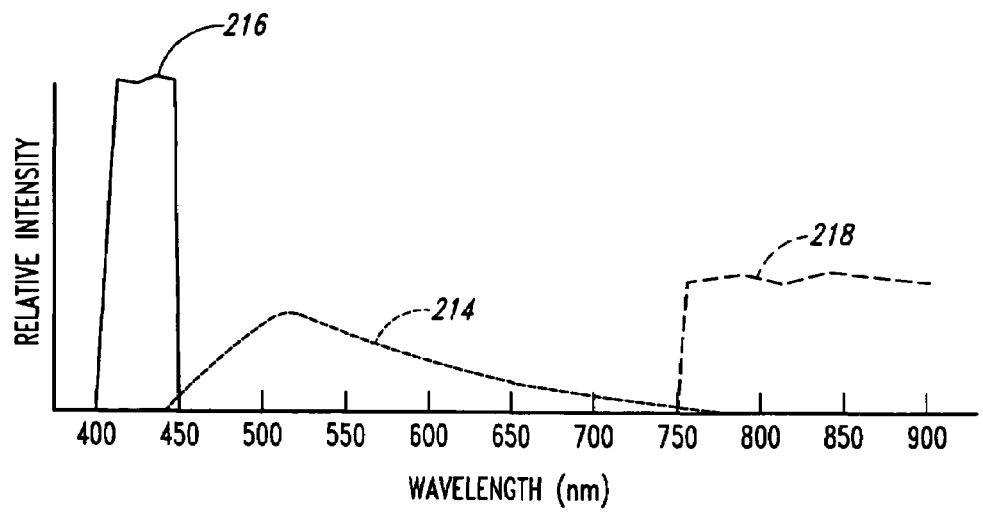
FIG. 13 is a graphical representation of radiation reflected and fluorescently emitted by an object when illuminated with the first spectral distribution shown in FIG. 10.

Referring to FIG. 13, in response to the excitation component 142, the tissue begins to fluoresce, thereby emitting a fluorescence component 214 at fluorescent wavelengths generally longer than those of the excitation component 142. Such fluorescent emissions are typically between 450 and 750 nm and tend to peak in the green wavelength range, at approximately 510 to 530 nm. Diseased or abnormal tissues exhibit considerably lower fluorescence emission intensity at these wavelengths than normal tissues. The tissue also reflects at least some of the excitation component energy that it does not absorb and fluorescently re-emit, thereby producing a reflected blue component such as that shown at 216.

In response to the NIR component 144, the tissue reflects a significant proportion of such near infrared radiation, thereby producing a reflected NIR component such as that shown at 218. Normal and diseased tissues produce such NIR reflectance with intensities that are much more similar to each other than the intensities of fluorescence of normal and diseased tissues, although there are measurable differences between the NIR reflectances of normal and diseased tissues, as discussed in greater detail below.

Thus, in response to irradiation with the excitation and NIR components, the tissue emits the fluorescence component 214 and reflects the reflected blue and NIR components 216 and 218. These three components are received by the endoscope 59, conveyed to the housing 62 via the coherent optical fiber bundle of the imaging channel 66 of the endoscope, and are received at the input port 64 of the housing to form the electromagnetic radiation beam 58.

Referring to FIGS. 2 and 12, block 212 then directs the processor circuit 41 to cause the first and second adjacent groups 54 and 56 of rays of the electromagnetic radiation beam 58 to be directed for receipt by the first and second measuring devices 44 and 46 respectively. More particularly, block 212 directs the processor circuit to direct the first group of rays for receipt by the first measuring device, by controlling the motion mechanism 61 to locate the reflective surface 60 of the beam-directing device 52 in the optical path of the electromagnetic beam 58 received from imaging channel 66 of the endoscope 59. The reflective surface 60 reflects the first group 54 of rays from the beam 58 to the first measurement port 70 for receipt by the spectrometer 48, while permitting the second group 56 of rays to bypass the reflective surface for receipt by the CCD camera 50. More particularly, the first group 54 of rays is reflected or directed within the housing to the lens 71 which focuses the first group of rays onto the first measurement port 70, which thus acts as a spectrometer port of the housing. The second group of rays is directed toward and received at the imaging device, i.e. the CCD camera. The first and second adjacent groups 54 and 56 of rays are thus received at the first and second measuring devices, namely, a spectroscopy device and an imaging device respectively.

Referring to FIGS. 2, 4 and 12, the radiation direction system 80 shown in FIG. 4 then directs respective wavelength ranges of incident radiation in the second group 56 of rays onto respective corresponding detector areas 81 in the CCD camera 50, as described above in connection with FIGS. 4 and 6.

Block 212 directs the processor circuit 41 to selectively adjust a gain of an imaging device in at least one wavelength range relative to a gain of the imaging device in at least one other wavelength range to produce an improved image of an object. To achieve this, in the present embodiment block 212 directs the processor circuit to signal the camera controlling electronics 49 shown in FIG. 2, to selectively adjust the gain settings of the individual detectors 87, 88 and 89 of the CCD camera 50 (although in this embodiment, the detector 86 is not used in this modality and therefore its gain setting need not be adjusted). More particularly, in this embodiment the processor circuit is directed to control the camera controlling electronics 49 to adjust the NIR wavelength range signal of the CCD camera 50 by adjusting the gain of the third and fourth detectors 88 and 89, and to adjust the green wavelength range signal by adjusting the gain of the second detector 87, to produce a desired NIR-to-green signal ratio for fluorescence imaging of the tissue being viewed by the endoscope 59. These NIR and green gain levels are set to a first set of gain levels, to enhance display of abnormal areas of the tissue in the fluorescence image, as described in greater detail above in connection with the gain adjustment capability of the CCD camera. More particularly, in this embodiment the green gain level of the second detector 87 is set to a very high value to compensate for the low intensity of fluorescence of the tissue, while the NIR gain levels of the third and fourth detectors 88 and 89 are set to moderate values in view of the moderate intensity of NIR reflectance by the tissue. Although in the present embodiment only the signal from the fourth detector 89 is used to normalize the fluorescence image, alternatively, the signal from the third detector 88 may be used for this purpose, or as a further alternative, the signals from both the third and fourth detectors 88 and 89 may be used, as described in greater detail below. In addition, the signals produced by the third and fourth detectors 88 and 89 may be used to produce a tissue oxygenation image of the tissue, as discussed below.

Thus, referring to FIGS. 2, 4, 13, and 14, as the second group 56 of rays, comprising the green fluorescence component 214, the reflected blue component 216 and the reflected NIR component 218, is received at the CCD camera 50, the reflected blue component 216 is received entirely at the first detector 86 due to the effect of the first partially reflecting device 90. The second detector 87 receives a portion of the green fluorescence component having wavelengths between 500 and 600 nm, due to the operation of the first and second partially reflecting devices 90 and 92 and the BP filter 104. The third detector 88 receives a portion of the reflected NIR component 218 that lies in the first NIR wavelength band 116 (750 to 800 nm), due to the operation of the first, second and third partially reflecting devices 90, 92 and 94 and the BP filter 106. The third detector 88 also receives a portion of the fluorescence component having wavelengths between 600 nm and 750 nm, although this component has a much smaller intensity than the first NIR wavelength band 116 portion of the reflected NIR component 218 received by the third detector. The fourth detector 89 receives a portion of the reflected NIR component 218 that lies in the second NIR wavelength band 118 (800 nm to 900 nm), due to the operation of the first, second and third partially reflecting devices 90, 92 and 94, the reflector 95 and the BP filter 108.

Figure 14:
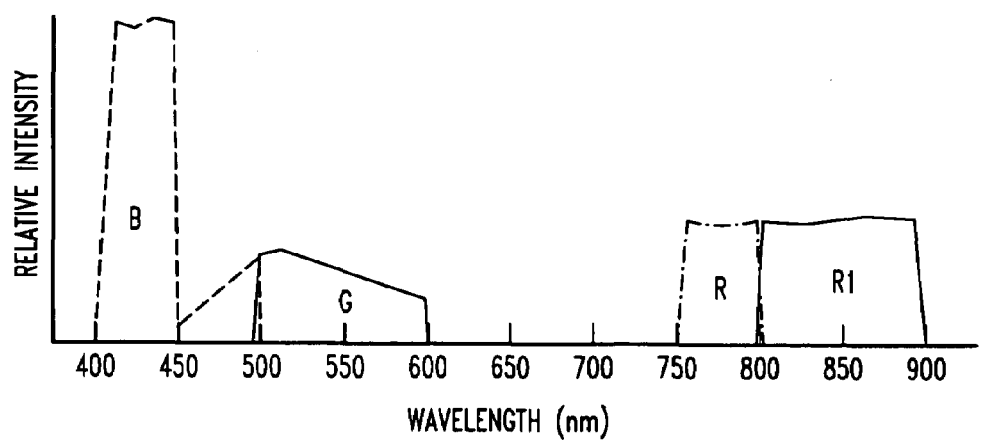
FIG. 14 is a graphical representation of detection spectral profiles for the imaging channels shown in FIG. 6 when the imaging device shown in FIG. 4 receives the radiation shown in FIG. 13 (fluorescence/NIR reflectance imaging mode)

FIG. 14 illustrates the detection spectral profile for each imaging channel (B, G, R, R1), resulting from the convolution of the spectral response of each individual imaging channel (as shown in FIG. 6) and the spectrum of the remitted radiation from the tissue in the fluorescence/NIR reflectance imaging mode (as shown in FIG. 13). However, the signal of the first detector 86 is discarded in this imaging modality. The second, third and fourth detectors 87, 88 and 89 produce signals in response to the 500 to 600 nm portion of the fluorescence component 214, the first NIR wavelength band 116 portion of the reflected NIR component 218 and the second NIR wavelength band 118 portion of the reflected NIR component 218 respectively, such signals being produced in proportion to the gain settings set by the processor circuit at block 212.

Referring to FIGS. 2 and 12, these signals produced by the second, third and fourth detectors 87, 88 and 89 are received at the camera controlling electronics 49 shown in FIG. 2.

Block 212 then directs the processor circuit 41 to control the camera controlling electronics 49 to cause the signals produced by the second and fourth detectors to be received at a green channel input 215 and a red channel input 217 respectively of a display device, which in this embodiment is the RGB color frame grabber 47. The NIR image signals received at the red channel input 217 are more accurate for fluorescence image normalization purposes than visible red light images, as the respective reflectances of normal and abnormal tissues at NIR wavelengths are even more similar than at visible red wavelengths. Block 212 directs the processor circuit to control the camera controlling electronics and the RGB color frame grabber to produce data signals representing improved, digitized fluorescence images, in response to the signals produced by the second and fourth detectors 87 and 89. The RGB color frame grabber 47 communicates the data signals produced in response to the signals received at the green channel input 215 to the color monitor 51 to produce a green fluorescence image of the tissue on the monitor, and similarly communicates the data signals produced in response to the signals received at the red channel input 217 to the color monitor to produce a red image of the tissue on the monitor, simultaneously with the display of the green fluorescence image. Thus, the resulting superposition on the monitor 51 of these green and red images is a normalized fluorescence image 234 of the tissue.

Thus, as explained in greater detail above, if normal tissue appears dark in the green fluorescence image due to geometric factors, then such tissue will also appear dark in the red channel NIR image and will thus appear dark in the normalized fluorescence image 234, which is a superposition of these two images. However, if tissue appears dark in the green fluorescence image because of abnormality or disease, such tissue is likely to appear brighter in the red channel NIR image, and therefore appears red in the normalized fluorescence image 234.

Referring to FIGS. 8, 12 and 13, block 212 then directs the processor circuit 41 to measure a spectrum of radiation from a point in an area of the object appearing in the improved image, i.e. the normalized fluorescence image 234. More particularly, block 212 directs the processor circuit to signal the control device and solenoid switch of the filter 128 of the spectrometer 48 shown in FIG. 8, to cause the filter 128 to extend into the path of radiation received at the entrance slit 126 of the spectrograph 127 from the first measurement port 70 via the optical fiber bundle 122. The filter 128 thus blocks the reflected blue component 216 from the first group 54 of rays, with the result that only the fluorescence component 214 and the reflected NIR component 218 are received by the spectrograph 127.

Figure 15:
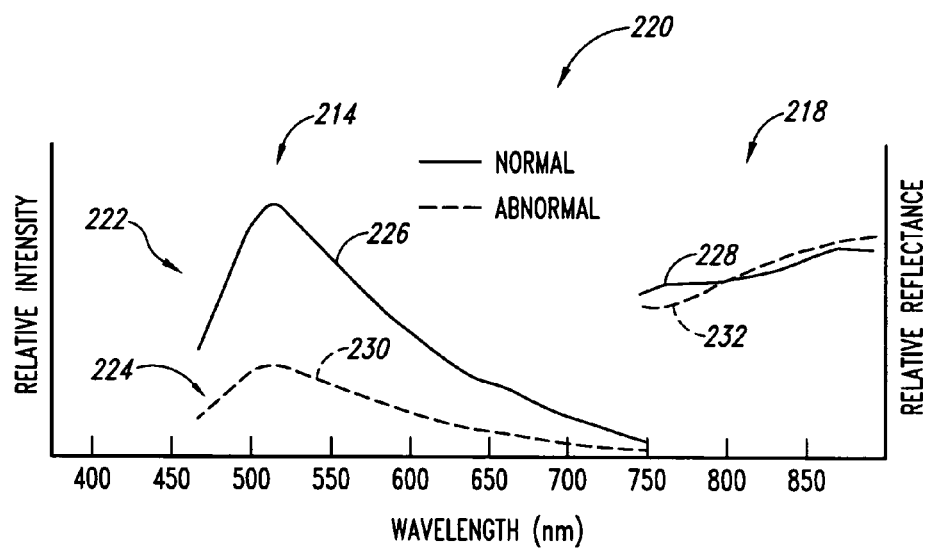
FIG. 15 is a graphical representation of fluorescence spectral distributions produced by normal and by abnormal tissue, and of NIR reflectance spectral distributions produced by normal tissue and by abnormal tissue, when illuminated with the first spectral distribution shown in FIG. 10.

Referring to FIGS. 8, 12, 13 and 15, block 212 then directs the processor circuit 41 to receive signals from the spectrometer 48 representing the spectral distribution of the fluorescence component 214 and the reflected NIR component 218, and to control the monitor 45 to display a fluorescence/NIR reflectance spectral distribution image 220 thereon. For example, for illustrative purposes, FIG. 15 shows a superposition of two separate spectral distribution images 222 and 224 corresponding to two different points in the tissue measured at two different respective times. The first spectral distribution image 222, shown as a solid line, corresponds to normal tissue, and has a fluorescence component 226 and a reflected NIR component 228. The second spectral distribution image 224, shown as a broken line, corresponds to abnormal tissue, and has a fluorescence component 230 of significantly lower intensity than the fluorescence component 226 corresponding to normal tissue. The second spectral distribution image 224 also has a reflected NIR component 232 whose intensity is similar to that of the reflected NIR component 228 corresponding to normal tissue. However, although the differences between the NIR reflected components 228 and 232 are much smaller than the differences between the fluorescence components 226 and 230, there are measurable differences between the two NIR reflected components of the spectra reflecting the tissue oxygenation status changes between normal and abnormal tissues. Below 800 nm, the normal tissue NIR reflectance is higher than that of the abnormal tissue, while above 800 nm the reverse is true.

Thus, referring back to FIG. 2, an operator (not shown) of the endoscope 59 is able to simultaneously view the normalized fluorescence image 234 on the monitor 51, and the fluorescence/NIR reflectance spectral distribution image 220 on the monitor 45. It will be appreciated that the reflective surface 60 of the beam-directing device 52, by directing the first group 54 of rays for receipt by the spectrometer 48, causes a black spot 236 to appear in the normalized fluorescence image 234, at a location corresponding to the first group 54 of rays. The spectrum is thus measured from a point in the tissue, corresponding to the black spot 236, in an area 237 of the tissue appearing in the improved image, i.e. the normalized fluorescence image 234.

Thus, by observing the location of the black spot 236 in the fluorescence image 234, the operator of the endoscope 59 immediately knows that the fluorescence/NIR reflectance spectral distribution image 220 on the monitor 45 is a spectrum of radiation emitted by the tissue at the point of the black spot 236 in the area 237 appearing in the normalized fluorescence image 234. The operator may therefore use the black spot 236 analogously to a target sight, to ensure that the fluorescence/NIR reflectance spectral distribution image 220 does in fact represent a spectrum of the desired point in the tissue area 237. In this manner, the operator of the endoscope may manipulate the endoscope so that the black spot 236 appears in an area 237 in the normalized fluorescence image 234 that is red and therefore suspicious, thereby allowing the operator to view a fluorescence/NIR reflectance spectral distribution image 220 corresponding to the suspicious red area, to confirm whether it is in fact diseased, and even to diagnose the particular disease. The operator is thus able to view a higher diagnostic sensitivity fluorescence image than previously possible, having a higher red-to-green signal ratio for example, while relying on the greater diagnostic specificity of spectroscopy to avoid or reduce false positive diagnoses which might otherwise result from such higher red-to-green signal ratio. If desired, the operator may further improve on this diagnostic specificity by executing a spectral analysis algorithm (not shown), which may be stored in the storage medium 202 for execution by the processor circuit 41.

Block 212 further directs the processor circuit 41 to continue to produce successive fluorescence/NIR reflectance spectral distribution images 220 and normalized fluorescence images 234 in real time in response to the electromagnetic radiation beam 58 received from the endoscope 59, until user input representing a new selection is received.

If, on the other hand, at block 211 it was determined that the user input indicated a selection of simultaneous NIR reflectance imaging and spectroscopy, block 213 configures the processor circuit 41 to produce an oxygenation image of the tissue in response to first and second signals produced by the third and fourth detectors 88 and 89, while simultaneously causing a reflectance spectrum of the tissue to be displayed on the monitor 45. To achieve this, block 213 first directs the processor circuit to ensure that the system 40 is configured for the fluorescence/NIR reflectance imaging modality with spectroscopy, in accordance with block 212. In this regard, if the system 40 had previously been carrying out simultaneous normalized fluorescence imaging and spectroscopy, no further re-configuration of the system is required for this initial step of block 213; otherwise, however, block 213 directs the processor circuit to control the electromagnetic radiation provider 53 to select and produce the first spectral distribution 138, to selectively adjust the gains of the detectors 87, 88 and 89, and to control the beam-directing device 52, the filter 128 of the spectrometer 48 and the monitor 45 to display the fluorescence/NIR reflectance spectral distribution image 220 thereon, all as described above in connection with block 212.

Referring to FIGS. 2, 4, 5, 12 and 13, in response to the NIR component 144 of the first spectral distribution 138, which in this embodiment includes radiation wavelengths between 750 nm and 900 nm, the tissue reflects such wavelengths to produce the reflected NIR component 218. As described above in connection with block 212, the reflected NIR component is conveyed to the radiation direction system 80 shown in FIG. 4, by the endoscope 59 shown in FIG. 2. As described above, the radiation direction system 80 (or more particularly, the first, second and third partially reflecting devices 90, 92 and 94 and the BP filter 106) is configured to direct, to the third detector 88, the radiation reflected by the tissue in the first NIR wavelength band 116 (750–800 nm), in which the absorption coefficient of deoxyhemoglobin is greater than that of oxyhemoglobin. Similarly, the radiation system 80 (in particular, the first, second and third partially reflecting devices 90, 92 and 94, the reflector 95 and the BP filter 108) is configured to direct, to the fourth detector 89, the radiation reflected by the tissue in the second NIR wavelength band 118 (800–900 nm), in which the absorption coefficient of oxyhemoglobin is greater than the absorption coefficient of deoxyhemoglobin.

The third detector 88 produces a first signal in response to the radiation reflected by the tissue in the first NIR wavelength band 116. Similarly, the fourth detector 89 produces a second signal in response to the radiation reflected by the tissue in the second NIR wavelength band 118. these first and second signals are received at the camera controlling electronics 49 shown in FIG. 2. In the present embodiment, the gain levels of the third and fourth detectors are left unchanged from those used for normalized fluorescence imaging. Alternatively, if desired, block 213 may be modified to direct the processor circuit to control the camera controlling electronics to set the gain levels of the third and fourth detectors to a second set of gain levels, to further enhance display of abnormal areas of the tissue in the resulting NIR reflectance image of the object.

Block 213 then directs the processor circuit to produce the oxygenation image of the tissue in response to these first and second signals produced by the third and fourth detectors 88 and 89. To achieve this, in this embodiment block 213 directs the processor circuit to control the camera controlling electronics to cause the first signals to be provided to a first color channel input of a multicolor display device, and to cause the second signals to be provided to a second color channel input of the display device. More particularly, the processor circuit is directed to control the camera controlling electronics to cause the signals produced by the third detector 88 to be provided to the green channel input 215 of the RGB color frame grabber 47, and to cause the signals produced by the fourth detector 89 to be provided to the red channel input 217 of the RGB color frame grabber 47. Block 213 directs the processor circuit to control the camera controlling electronics and the RGB color frame grabber to produce data signals representing improved, digitized NIR reflectance images, in response to the signals produced by the third and fourth detectors 88 and 89. The RGB color frame grabber 47 communicates these data signals to the color monitor 51 to simultaneously produce, on the monitor, a green image of the tissue representing reflectance intensity of the tissue in the first NIR wavelength band 116 and a red image of the tissue representing reflectance intensity of the tissue in the second NIR wavelength band 118. Thus, the resulting superposition on the monitor 51 of these green and red images is a normalized NIR reflectance image 235 of the tissue.

Due to the greater oxyhemoglobin content of normal tissues relative to diseased tissues and the corresponding greater deoxyhemoglobin content of diseased tissues, normal tissues will tend to appear brighter than diseased tissues in the green image, while diseased tissues will tend to appear brighter than normal tissues in the red image. Tissues which are partly obstructed from view due to geometrical factors will appear dark in both the green and red images. Thus, in the normalized NIR reflectance image 235, diseased tissues will tend to be displayed as red areas in a background of green normal tissue.

As with the normalized fluorescence image 234, the black spot 236 also appears at the center of the normalized NIR reflectance image 235, due to the re-direction by the beam-directing device 52 of the first group of rays 54 of the electromagnetic radiation beam 58, for receipt by the spectrometer 48. Thus, as with simultaneous normalized fluorescence imaging and spectroscopy, the operator of the endoscope may manipulate the endoscope so that the black spot 236 appears in an area in the normalized NIR reflectance image 235 that is red and therefore suspicious, thereby allowing the operator to view a NIR reflectance spectral distribution image 220 corresponding to the suspicious red area on the monitor 51, to confirm whether the suspicious area is diseased, and optionally, to diagnose the particular disease.

Block 213 further directs the processor circuit 41 to continue to produce successive NIR reflectance spectral distribution images 220 and normalized NIR reflectance images 235 in real time in response to the electromagnetic radiation beam 58 received from the endoscope 59, until user input representing a new selection is received.

Referring to FIGS. 2 and 12, if no user input representing selection of combined fluorescence imaging/NIR reflectance imaging and spectroscopy was detected at block 210, block 238 directs the processor circuit 41 to determine whether user input indicating a selection of a combined white light reflectance imaging and spectroscopy mode has been received at the user input device 204.

If such user input has been received, block 240 directs the processor circuit 41 to control the electromagnetic radiation provider 53, the CCD camera 50, the beam-directing device 52, and the spectrometer 48, as follows.

Referring to FIGS. 9, 11 and 12, block 240 first directs the processor circuit 41 to select and produce the second spectral distribution 140 for white light reflectance imaging, the second spectral distribution 140 including white light illumination component 146 received from the first optical subsystem 134. In this regard, block 240 directs the processor circuit to cause the first and second optical subsystems 134 and 136 shown in FIG. 9 to function in the second operational mode. More particularly, block 240 directs the processor circuit to activate the lamp 180, and to signal the control devices 160 and 172 to place the solenoid switches 158 and 170 respectively in extended positions, such that the color balance filter 154 is placed in the path of radiation passing through the first optical subsystem 134 and the light stopper 166 is placed in the path of radiation passing through the second optical subsystem 136.

Thus, the beam splitter 184 receives input radiation including the excitation, NIR and white light illumination components, from the lamp 180. The beam splitter 184 provides visible light, and therefore provides the excitation and white light illumination components 142 and 146, to the first optical subsystem 134. The beam splitter provides near infrared radiation, and therefore provides the NIR component 144, to the second optical subsystem 136. The white light illumination and excitation components 146 and 142 are received from the beam splitter at the first optical subsystem 134, which transmits the white light illumination component 146 shown in FIG. 11, which in this embodiment is a flat spectral distribution of visible light ranging from 400 nm to 700 nm, to the combiner 173. The NIR component 144 is received from the beam splitter, via the redirecting device 188, at the second optical subsystem 136, which blocks all such received near infrared radiation. Therefore, in the second operational mode, the combiner 173 does not receive any radiation from the second optical subsystem 136.

The combiner 173, or more precisely the dichroic reflecting device 174, transmits the white light illumination component 146 received from the first optical subsystem 134 along the common optical path 175, through the lens 176, to the exit port 178. Thus, in the second operational mode, the optical system 132 transmits the white light illumination component 146 from the first optical subsystem 134 while blocking the NIR component 144.

Referring back to FIGS. 2 and 11, the white light illumination component 146 of the second spectral distribution 140 is then conveyed from the exit port 178 to the endoscope 59 and ultimately to the tissue being imaged, via the optical fiber bundle 55.

Figure 16:
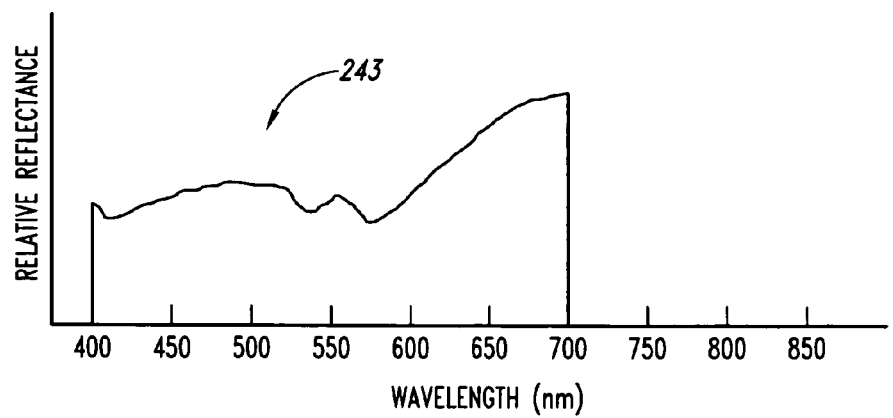
FIG. 16 is a graphical representation of radiation reflected by an object when illuminated with the second spectral distribution shown in FIG. 11.

Referring to FIGS. 2, 11, and 16, in response to illumination of the tissue with the white light illumination component 146, the tissue reflects a white light reflectance imaging component shown at 243 in FIG. 16, whose intensity at the wavelengths of the white light illumination component 146 varies in proportion to the natural reflectance characteristics, i.e. the color, of the tissue. This white light reflectance imaging component is received by the endoscope 59 and conveyed to the input port 64 of the housing 62 via the coherent optical fiber bundle of the imaging channel 66 of the endoscope, to form the electromagnetic radiation beam 58.

Referring to FIGS. 2 and 12, block 240 then directs the processor circuit 41 to cause the first and second adjacent groups 54 and 56 of rays to be directed for receipt by the first and second measuring devices 44 and 46 respectively. To achieve this, block 240 directs the processor circuit to control the motion mechanism 61 to place the beam-directing device 52 in the optical path of the electromagnetic beam 58 received from the endoscope 59, so that the first group 54 of rays is reflected by the reflective surface 60 to the first measurement port 70 for receipt by the spectrometer 48, and the second group 56 of rays bypasses the reflective surface for receipt by the CCD camera 50.

Referring back to FIGS. 2, 4 and 12, block 240 directs the processor circuit 41 to selectively adjust a gain of the imaging device, which in this embodiment is the CCD camera 50, in at least one wavelength range relative to a gain of the imaging device in at least one other wavelength range to produce an improved image of an object. More particularly, block 240 directs the processor circuit to signal the camera controlling electronics 49 shown in FIG. 2, to selectively adjust the gain settings of the individual detectors 86, 87 and 88 of the CCD camera 50. In this embodiment the processor circuit is directed to adjust the red, green and blue wavelength range gain levels of the CCD camera 50 by adjusting the gains of the first, second and third detectors 86, 87 and 88, to produce a desired color balance for white light reflectance imaging of the tissue being viewed by the endoscope 59. These red, green and blue gain levels are set to a third set of gain levels, to enhance display of abnormal areas of the tissue in the resulting white light reflectance image, as described in greater detail above in connection with the gain adjustment capability of the CCD camera. Typically, this set of gain levels comprises moderate gain values for all three detectors because the reflected radiation has moderate intensity in each of the blue, green and red wavelength ranges. The fourth detector 89 does not produce any signals, as the tissue is not being illuminated with, and is therefore not reflecting, any radiation in the wavelength range between 800 nm and 900 nm.

Figure 17:
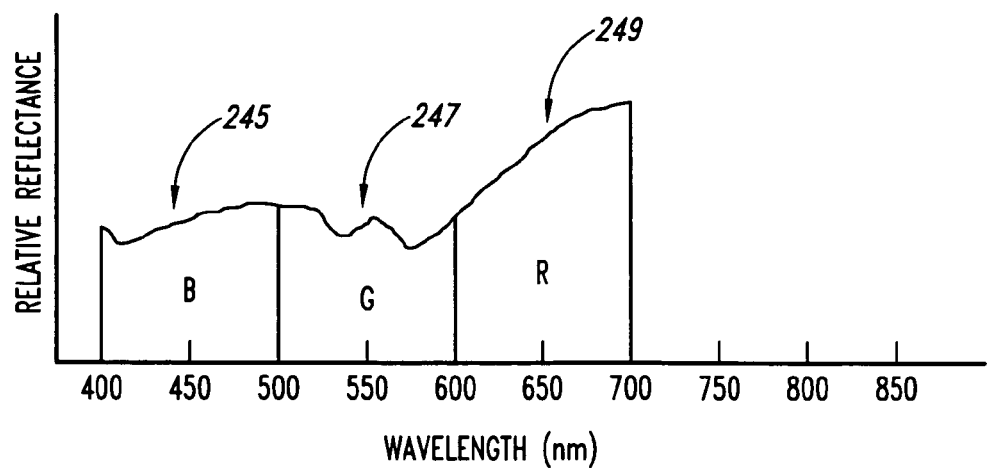
FIG. 17 is a graphical representation of the detection spectral profiles for the imaging channels shown in FIG. 6 when the imaging device shown in FIG. 4 receives the radiation shown in FIG. 16 (white light reflectance imaging mode)

Thus, referring to FIGS. 2, 4, 11, 16, and 17, as the second group 56 of rays, comprising the white light reflectance imaging component 243 produced by the tissue in response to illumination with the white light illumination component 146, is received at the CCD camera 50, the first detector 86 receives a blue portion 245 of the white light reflectance imaging component 243 having wavelengths between 400 and 500 nm, due to the operation of the first partially reflecting device 90. The second detector 87 receives a green portion 247 of the white light reflectance imaging component 243 having wavelengths between 500 and 600 nm, due to the operation of the first and second partially reflecting devices 90 and 92 and the BP filter 104. The third detector 88 receives a red portion 249 of the white light reflectance imaging component 243 having wavelengths between 600 and 700 nm, due to the operation of the first, second and third partially reflecting devices 90, 92 and 94 and the BP filter 106. The detectors 86, 87 and 88 produce signals in response to the blue (245), green (247) and red (249) portions respectively, such signals being produced in proportion to the gain settings set by the processor circuit at block 240. FIG. 17 illustrates the detection spectral profile for each imaging channel (B, G, R), resulting from the convolution of the spectral response of each individual imaging channel (as shown in FIG. 6) and the spectrum of the remitted radiation from the tissue in white light reflectance imaging mode.

Referring to FIGS. 2 and 12, these signals produced by the first, second and third detectors 86, 87 and 88 are received at the camera controlling electronics 49 shown in FIG. 2.

Block 240 directs the processor circuit 41 to control the camera controlling electronics 49 to communicate these signals produced by the first, second and third detectors 86, 87 and 88 to a blue channel input 219, the green channel input 215 and the red channel input 217 respectively of the RGB color frame grabber 47. Block 240 directs the processor circuit to control the camera controlling electronics and the RGB color frame grabber to produce data signals representing an improved, digitized white light reflectance image 246 of the tissue, in response to the signals produced by the first, second and third detectors 86, 87 and 88. The RGB color frame grabber 47 communicates these data signals to the color monitor 51 to display the white light reflectance image 246 thereon.

Referring to FIGS. 8 and 12, block 240 then directs the processor circuit 41 to measure a spectrum of radiation from a point in an area of the object appearing in the improved image, i.e. the white light reflectance image 246. More particularly, block 240 directs the processor circuit to signal the control device and solenoid switch of the filter 128 of the spectrometer 48 shown in FIG. 8, to cause the filter 128 to retract out of the path of radiation received at the entrance slit 126 of the spectrograph 127 from the first measurement port 70 via the optical fiber bundle 122. The first group 54 of rays of the electromagnetic radiation beam, which in this mode is the white light reflectance imaging component 243, is thus received by the spectrograph 127 in an unfiltered state.

Referring to FIGS. 2, 8 and 12, block 240 then directs the processor circuit 41 to receive signals from the spectrometer 48 representing the spectral distribution of the white light reflectance imaging component 243, and to control the monitor 45 to display a white light reflectance spectral distribution image 241 thereon in response to the signals received from the spectrometer.

Thus, referring back to FIG. 2, an operator (not shown) of the endoscope 59 is able to simultaneously view the white light reflectance image 246 on the monitor 51, and the white light reflectance spectral distribution image 241 on the monitor 45. As described above in connection with block 212, the operator may use the black spot 236 appearing at the center of the white light reflectance image 246 in the monitor 51 to indicate the precise point, in the area 237 of the tissue, that is being measured by the spectrometer 48 to produce the visible reflectance spectral distribution image 241 on the monitor 45.

Block 240 further directs the processor circuit to continue to produce white light reflectance spectral distribution images 241 and white light reflectance images 246 in real time in response to the beam 58 received from the endoscope 59, until user input representing a new selection is received.

Referring to FIGS. 2 and 12, if no user input representing selection of combined white light reflectance imaging and spectroscopy was detected at block 238, block 250 directs the processor circuit 41 to determine whether user input indicating a selection of a fluorescence/NIR reflectance imaging mode without spectroscopy has been received at the user input device 204.

If such user input has been received, block 251 directs the processor circuit 41 to determine whether the user input received at block 250 is indicative of a selection of normalized fluorescence imaging, or NIR reflectance imaging. In this embodiment, as discussed above in connection with blocks 210 to 213, the physical measurements for both fluorescence and NIR reflectance imaging are performed simultaneously in a single fluorescence/NIR reflectance imaging modality.

Referring to FIGS. 2, 4 and 12, if at block 251 the user input indicates a selection of normalized fluorescence imaging without spectroscopy, block 252 directs the processor circuit 41 to control the electromagnetic radiation provider 53 to function in the first operational mode, as described above in connection with block 212. Block 252 further directs the processor circuit to signal the camera controlling electronics 49 to adjust the gain levels of the detectors of the CCD camera 50 to improve the resulting normalized fluorescence image to enhance display of abnormal areas of the tissue, also as described above in connection with block 212. However, in this embodiment block 252 directs the processor circuit to control the motion mechanism 61 to remove the beam-directing device 52 from the optical path of the electromagnetic radiation beam 58 received from the endoscope 59, so that both the first and second adjacent groups 54 and 56 of rays are received at the CCD camera 50. Block 252 then directs the processor circuit to control the camera controlling electronics 49 and the RGB color frame grabber 47 to produce the normalized fluorescence image 234 of the object, as discussed above in connection with block 212. Due to the removal of the beam-directing device 52 from the optical path of the electromagnetic beam 58, the black spot 236 does not appear in the normalized fluorescence image 234 in this mode. Block 252 directs the processor circuit to continue monitoring such signals to produce successive normalized fluorescence images 234 in real time, until user input representing a new selection is received.

If, on the other hand, at block 251, the user input indicates a selection of NIR reflectance imaging without spectroscopy, block 253 directs the processor circuit 41 to control the motion mechanism 61 to remove the beam-directing device 52 from the optical path of the electromagnetic radiation beam 58 received from the endoscope 59, so that both the first and second adjacent groups 54 and 56 of rays are received at the CCD camera 50. Otherwise, block 253 directs the processor circuit to control the camera controlling electronics 49, the RGB color frame grabber 47, and the electromagnetic radiation provider 53 to produce the NIR reflectance image 235 of the object, as discussed above in connection with block 213. Again, due to the removal of the beam-directing device 52 from the optical path of the electromagnetic beam 58, the black spot 236 does not appear in the NIR reflectance image 235 in this mode. Block 253 directs the processor circuit to continue monitoring such signals to produce successive NIR reflectance images 235 in real time, until user input representing a new selection is received.

If no user input representing selection of fluorescence/NIR reflectance imaging without spectroscopy was detected at block 250, block 254 directs the processor circuit 41 to determine whether user input indicating a selection of a white light reflectance imaging mode without spectroscopy has been received at the user input device 204.

Referring to FIGS. 2, 4 and 12, if such user input is detected at block 254, block 256 directs the processor circuit 41 to control the electromagnetic radiation provider 53 to function in the second operational mode, as described above in connection with block 240. Block 256 further directs the processor circuit to signal the camera controlling electronics 49 to adjust the gain levels of the detectors of the CCD camera 50 to improve the resulting white light reflectance image to enhance display of abnormal areas of the tissue, also as described above in connection with block 240. Block 256 then directs the processor circuit to signal the motion mechanism 61 to remove the beam-directing device 52 from the optical path of the electromagnetic radiation beam 58, as described above in connection with block 252. Block 256 then directs the processor circuit to receive data signals from RGB color frame grabber 47 representing a digital image in response to signals received at the blue, green and red channels of the RGB color frame grabber from the first, second and third detectors 86, 87 and 88 of the CCD camera respectively. Block 256 directs the processor circuit to produce and display the digital image, which is the white light reflectance image 246 of the tissue, on the monitor 51, as described above in connection with block 240. Due to the removal of the beam-directing device 52 from the optical path of the electromagnetic beam 58, the black spot 236 does not appear in the white light reflectance image 246 in this mode. Block 256 directs the processor circuit to continue monitoring such signals to produce successive white light reflectance images 246 in real time, until user input representing a new selection is received.

If no user input representing selection of white light reflectance imaging without spectroscopy was detected at block 254, block 258 directs the processor circuit 41 to determine whether user input indicating the imaging process is to be ended has been received at the user input device 204. If so, the measurement routine 200 is ended. If not, the processor circuit is directed back to block 210 to continue monitoring for user input indicating a new selection.

Alternatives

The present invention encompasses various alternatives to the systems, methods, etc., discussed above, including the exemplary alternatives discussed in this section. These alternatives are exemplary only; other suitable alternatives are also within the scope of the present invention.

Figure 20:
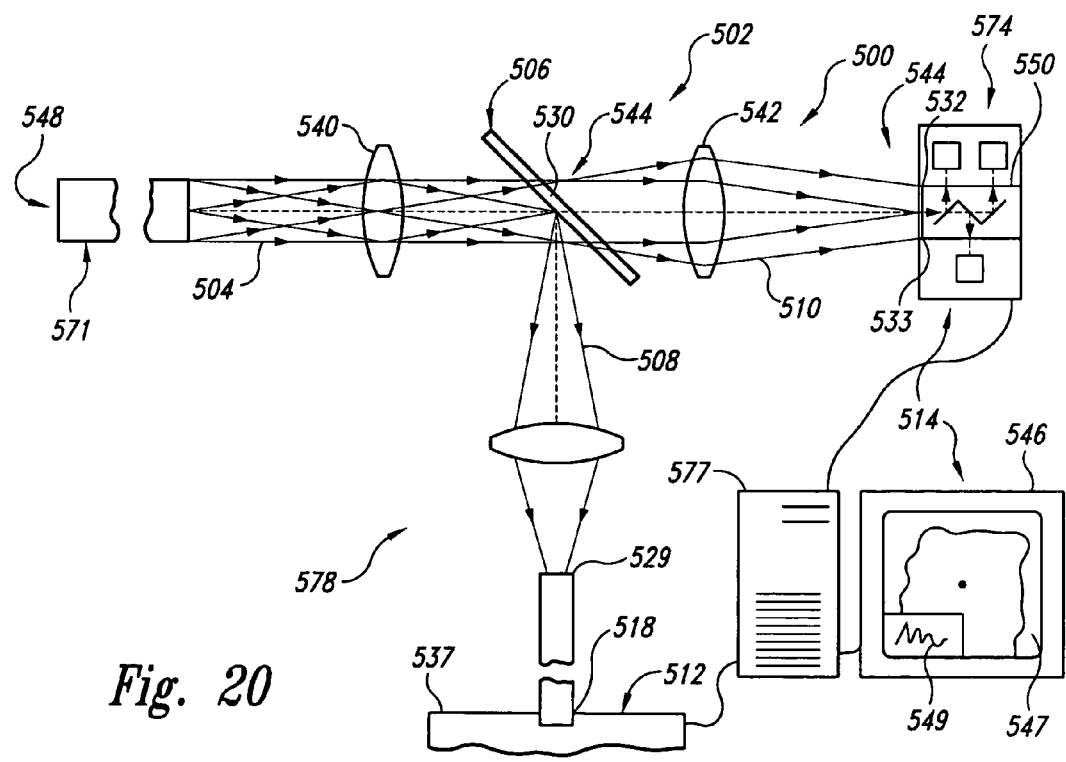
FIG. 20 is a schematic representation of an apparatus for facilitating contemporaneous measurements of electromagnetic radiation with multiple measuring devices wherein the beam separator is disposed at a conjugate image plane with the imaging device.
Figure 21:
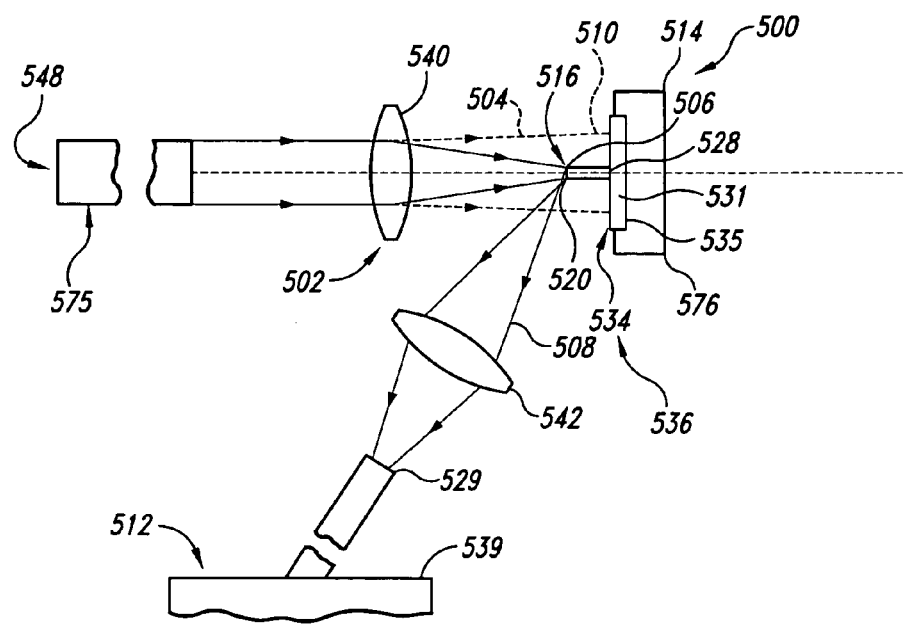
FIG. 21 is a schematic representation of an apparatus for facilitating contemporaneous measurements of electromagnetic radiation with multiple measuring devices wherein the beam separator is located immediately in front of the imaging device.
Figure 22:
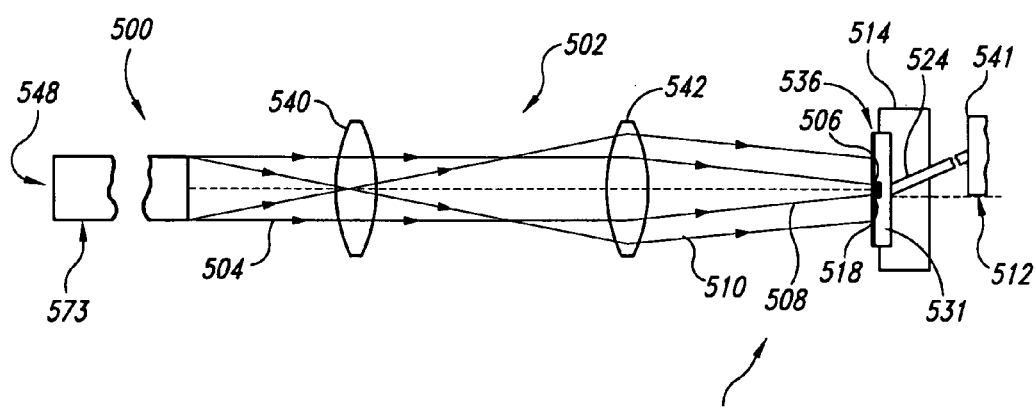
FIG. 22 is a schematic representation of an apparatus for facilitating contemporaneous measurements of electromagnetic radiation with multiple measuring devices wherein the beam separator is disposed within the imaging device.

Turning to some exemplary alternatives, FIGS. 20–24 schematically depict some further alternative embodiments. Turning first to FIGS. 20–22, the Figures depict a light beam detection system 500 comprising an area 502 sized to receive light beam 504. As with certain other embodiments depicted in other Figures herein, light beam 504 is typically a detection light beam emanating from (e.g., reflected from, transmitted through or fluorescing or phosphorescing from) a sample or object, such as a human organ or skin, or a computer chip. Light beam 504 can be any other desired light beam, such as a light beam from a light source to be sampled. The light beam detection system 500 can be any desired detection system, such as endoscope 59 depicted in several Figures, or microscope 571 depicted in FIG. 20, telescope 573 depicted in FIG. 22, camera 575 depicted in FIG. 21, digital imaging system 574 depicted in FIG. 20 and film imaging system 576, depicted in FIG. 21.

A beam separator 506 is disposed in area 502 to separate a small portion of light beam 504 from a remainder of light beam 504 to provide separated light beam 508 and remainder light beam 510. The beam separator 506 transmits separated light beam 508 to spectroscopy device 512 while remainder light beam 510 proceeds to an imaging device 514. Small portion indicates a small enough percentage of the total light in light beam 504 to provide both an accurate spectrum and an accurate image. The small portion can, for example, be a small cross section of light beam 504 or a small percentage of light taken from a large cross-section of light beam 504. Exemplary beam separators, as noted elsewhere herein, include beam splitters, small mirrors and lenses. If desired, beam separator 506 can transmit a bulk of the light beam 504 to an imaging device while permitting a small portion of the light to continue on to a spectroscopy device. If desired, as depicted in FIG. 20 and discussed in exemplary detail in relation to FIGS. 4, 7, 23 and 24, the imaging device can comprise an image separator 550.

Spectroscopy device 512 is optically connected to beam separator 506 to receive separated light beam 508 and to provide a spectrum (or spectra) therefrom. Spectroscopy device 512 can be any desired instrument for measuring and reporting spectra, including, if desired, displaying the spectrum in graphical or numerical form. Suitable spectroscopy devices include, for example, spectrometers 48 (e.g., FIG. 2) such as a scanning monochromater coupled with a single channel detector, spectroradiometers 537 (e.g., FIG. 20), spectrographs 539 (e.g., FIG. 21), and interferometer based spectrometers 541 (e.g., FIG. 22) such as a FT (Fourier transform) type spectrometer, or other desired devices.

Imaging device 514 is disposed in area 502 to operably receive remainder light beam 510 and to provide an image therefrom. As used in this context, imaging device 514 includes an imaging detector that is operably linked to an image controller or generator that can be remotely located. Imaging device 514 can also indicate the entire device, or a channel that obtains the image then transports it to a remotely located detector/device. Exemplary imaging devices include both pixelated detectors 532 (as depicted in, e.g., FIGS. 20 and 22), such as a CCD, an intensified CCD, a CMOS (complementary metal-oxide semi-conductors), a CID (charge injection device), a photodiode array, a photomultiplier array, and non-pixelated detectors 534 (as depicted in, e.g., FIG. 21) such as a film camera.

In FIGS. 20 and 21, spectroscopy device 512 is located outside of light beam 504. In FIG. 22, spectroscopy device 512 is located in light beam 504. In FIG. 21 beam separator 506 comprises light redirection device 516, which is sized and located to intercept a small area of light beam 504 and change the direction of such small area of light beam 504 toward spectroscopy device 512. In FIGS. 21 and 22, light redirection device 516 imparts a small residual image 528 in remainder light beam 510 that corresponds to the location of light redirection device 516 in light beam 504. In some embodiments, light redirection device 516 and small residual image 528 are located substantially in the radial center of light beam 504. Light redirection device 516 can be disposed, however, at any desired location in light beam 504, from the center to the edge. Typically, the entire light redirection device 516 is located in light beam 504, but only a portion of light redirection device 516 can be so located if desired. Light redirection device 516 can be, for example, a mirror 520, a lens (depicted in previous Figures as 71), a measurement port 518 of spectroscopy device 512, a prism such as prism 119 in FIG. 7, or a light guide 524 such as light guide 524 in FIG. 22 (also depicted in FIG. 2 as 55 and in FIG. 8 as 122).

In FIGS. 21 and 22, light redirection device 516 removes substantially all light incident on light redirection device 516 from remainder light beam 510, which indicates that light redirection device 516 typically removes at least about 90%, up to 100%, of the incident light, enough to leave a strong shadow or small residual image in the remainder light beam 510.

In FIG. 20, light beam detection system 500 comprises a beam separator 506 that is a beam splitter 530. Beam splitter 530 intercepts a large portion of light beam 504 such that the beam splitter 530 does not leave a significant residual image. Avoiding such a significant residual image can be achieved, for example, because beam splitter 530 covers substantially all of light beam 504 so the remainder light beam 510 is uniform or because beam splitter 530 reflects little light as a percentage of the total light in light beam 504. Beam splitter 530 transmits substantially more than 50% of the electromagnetic radiation in light beam 504 to imaging device 514 and reflects substantially less than 50% of the electromagnetic radiation in light beam 504 to spectroscopy device 512 (or vice-versa, if the positions of spectroscopy device 512 and imaging device 514 are reversed). Typically, beam splitter 530 transmits at least about 80%, 90% or 95–97% of light beam 504 and reflects at most a corresponding percentage of light beam 504.

Continuing to discuss FIG. 20, light beam detection system 500 comprises a first focusing element, which as depicted is a first focusing lens 540, in front of beam separator 506 and a second focusing element, which as depicted is a second focusing lens 542, between beam separator 506 and imaging device 514. The first focusing element and the second focusing element provide a first conjugate image plane 544 substantially at beam separator 506 and a second conjugate image plane 544 substantially at imaging device 514. Conjugate image planes are locations along a light path where an image (for example, of the sample or an aperture diagram) are recreated. In FIGS. 21 and 22, beam separator 506 is located in substantially the same image plane 536 as imaging device 514.

Thus, in some embodiments, beam separator 506 can be located substantially in front of (upstream) and does not touch imaging device 514, while in other embodiments beam separator 506 abuts imaging device 514 and/or is behind (downstream from) imaging device 514. Similarly, beam separator 506 can be located in a conjugate image plane of the imaging device 514 or in the same conjugate image plane as the imaging device.

FIGS. 20–22 also depict an image and spectral detection system 578, which is the detection portion of light beam detection system 500, and various relational embodiments of the spectroscopy device 512 and the imaging device 514. For example, as in FIG. 22, the imaging detector can be disposed substantially coplanar with beam separator 506 for spectroscopy device 512, the imaging detector and the beam separator together sized to receive light beam 504. The imaging detector comprises detection area 531 that surrounds measurement port 518. In certain embodiments, the imaging detector and the beam separator can be side-by-side, or the beam separator can be encompassed by the imaging detector, for example where the beam separator is located substantially in the center of the imaging detector.

In FIG. 22, the beam separator is a light collection element that functions as a measurement port 518 for spectroscopy device 512 located immediately behind the imaging detector. The light collection element can also be an input end 529 of a light guide that transmits collected light to a remotely located spectroscopy device. Suitable light guides include optical fibers, fiber bundles, liquid light guides and hollow reflective light guides or lens systems.

The beam separator can also be, for example, a focusing or non-focusing element such as a mirror or a focusing element such a lens or focusing mirror that transmits collected light to a remotely located spectroscopy device. In other embodiments, where the imaging device 514 is able to determine spectra, the light collection element can comprise a portion of imaging device 514 dedicated to spectral determination. The imaging detector comprises a detection area 531 to receive light beam 504 and the beam separator can be less than about 20%, 10%, 5% to 3% or 1% or even less of the detection area 531 of the imaging detector.

FIG. 20 further depicts a display device 546 operably connected to imaging device 514 to display an image 547 from imaging device 514, and operably connected to spectroscopy device 512 to display a spectrum 549 from spectroscopy device 512. The display device 546 can be a single display device operable to contemporaneously or sequentially display both the image from imaging device 514 and the spectrum from spectroscopy device 512, or the display device can comprise multiple different displays and/or devices. Additionally, display device 546 can be operable to display, contemporaneously or sequentially, multiple images, for example of different wavelength regions or of different objects (such as a stored image of an idealized object or the object at a previous time, which image can then be compared by the physician or other user to the present image) and/or multiple spectra.

FIGS. 20–22 further depict a light collection port 548 sized to receive light beam 504 directly from a sample or light source or other light beam to be measured and sampled. If desired, an optical relay system operably connects light collection port 548 to area 502, to transmit light beam 504 to the area 502.

FIG. 20 also depicts a controller or computer 577 operably connected to system imaging device 514 and spectroscopy device 512 and containing computer-implemented programming that controls imaging device 514 and spectroscopy device 512. More than one controller can be used if desired, and the controller(s) can control any one or more of the imaging device 514, spectroscopy device 512, and other features of the system. For example, if desired, the controller can control the selection and display of different wavelength regions as discussed elsewhere herein.

Figure 23:
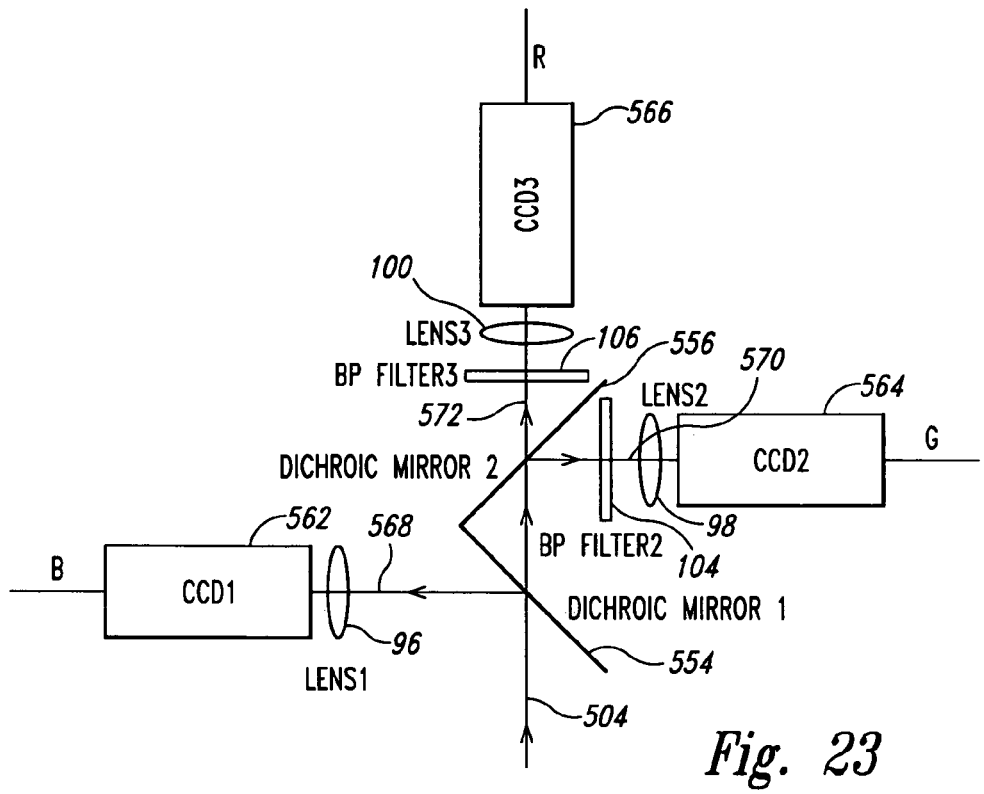
FIG. 23 is a schematic representation of an imaging device wherein the beam separators are disposed in alternating relationship.
Figure 24:
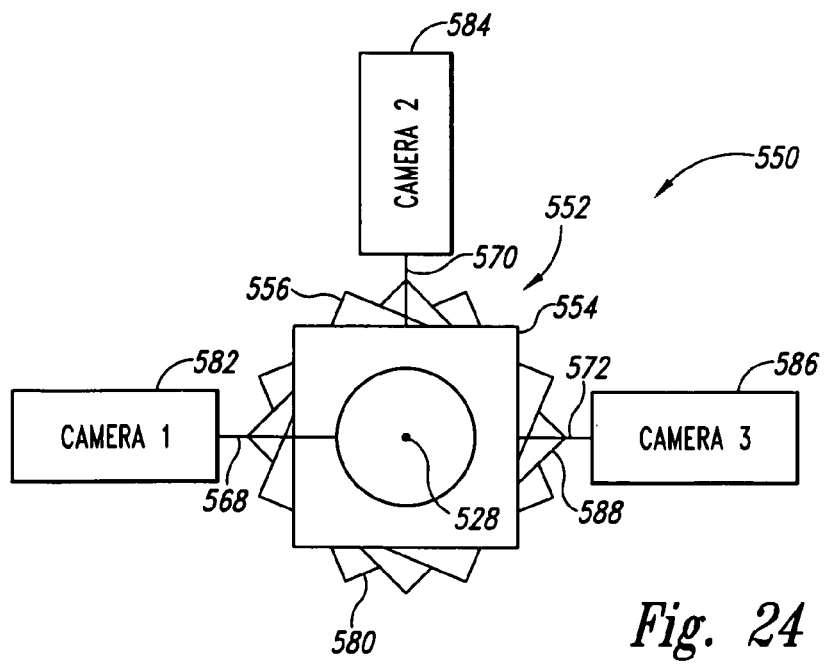
FIG. 24 is a schematic representation of an imaging device wherein the beam separators are disposed in radial relation about the light beam and an imaging device is disposed directly behind the beam separators.

Turning to FIGS. 23–24, light beam detection system 500 can comprise an image separator 550. Light beam detection systems are also depicted in FIGS. 4 and 7. Image separator 550 typically comprises a plurality of light selection elements 552 such as beam splitters 554, 556, 558, band pass filters 104, 106, long pass filters, short pass filters, prisms, or other desired optical selection elements (see also FIGS. 4 and 7), and separates the image conveyed by light beam 504 into a plurality of selected wavelength region images wherein each selected wavelength region image corresponds to a different wavelength region of the range of wavelengths in light beam 504.

As depicted in FIGS. 23 and 24, the image separator comprises a plurality of imaging beam splitters 554, 556, 558. "Imaging beam splitters" indicates beam splitters in the imaging module/device, as opposed, for example, to beam splitters located in other places in the system, such as beam splitter 530 in light beam 504 upstream of imaging device 514. Each imaging beam splitter 554, 556, 558 in FIGS. 23 and 24 selects for a different selected wavelength region, as discussed elsewhere herein, to provide the selected wavelength region images and directs the selected wavelength region images to different imaging devices. If desired, however, the different imaging devices can be different regions or detection areas of a single imaging detector.

In some embodiments, the different wavelength regions comprise at least two, three or all of UV to blue light, visible light, near-infrared light and infrared light. The different wavelength regions can also be selected to incorporate any desired wavelength ranges, such as red, blue and green, or such that specific fluorescence signals are selectively detected, for example those signals corresponding to oxy-hemoglobin and deoxyhemoglobin, or signals corresponding to two or more different states of a given object or sample, such as cancerous tissue versus non-cancerous tissue, or healthy transplanted tissue versus transplant tissue undergoing rejection.

Typically, as depicted in FIG. 20 and elsewhere, a display device 546 is operably connected to the image separator to contemporaneously or sequentially display at least two images selected from the desired wavelength ranges. Preferably, display device 546 is further able to contemporaneously or sequentially display the spectrum 549 from spectroscopy device 512.

In FIGS. 4 and 23, the imaging beam splitters are disposed linearly along light beam 504. FIG. 23 depicts an embodiment comprising three different selected wavelength regions (there can be two or more), and thus two imaging beam splitters 554, 556 are disposed alternatingly such that a first sub-set (i.e., one or more) of the imaging beam splitters direct a first set of selected wavelength region images 568, in a first direction through lens 96 to imaging device 562, a second sub-set (i.e., one or more) of the imaging beam splitters direct a second set of selected wavelength region images 570 in a second direction through lens 98 to imaging device 564, and a third sub-set (i.e., one or more) of selected wavelength region images 572 passes directly through lens 102 to imaging device 566. In the embodiment shown, the second direction is substantially 90° away from the first direction; other angles such as 45° or 180° can also be used if desired. The configuration in FIG. 23, we well as certain other configurations herein, also leads to a balanced, compact mechanical layout suitable for building a compact and lightweight camera.

In FIG. 24, three imaging beam splitters 554, 556, 558 are disposed to reflect the selected wavelength region images 568, 570, 572 in at least three different radial directions and the different imaging devices, which in this embodiment are cameras 582, 584, 586, are disposed radially about light beam 504 to receive the selected different wavelength images 568, 570, 572. In FIG. 24, imaging beam splitters 554, 556, 558 select for all but one desired, selected different wavelength region to provide a non-selected wavelength region image. The image separator further comprises an imaging detector 580 located in light beam 504 and behind the imaging beam splitters 554, 556, 558 to directly receive the non-selected wavelength region image. Thus, as shown for example in FIGS. 4, 7, 23 and 24, in some embodiments the present invention provides an imaging system able to provide a plurality of images corresponding to different wavelength regions of an initial image. The imaging system comprises an image separator comprising a light beam path and a plurality of imaging beam splitters 554, 556, 558 or other desired image separators disposed in the light beam path. Each of the imaging beam splitters 554, 556, 558 selects for different selected wavelength regions of the initial image to provide corresponding different selected wavelength region images and directing the different selected wavelength region images to different imaging devices. The imaging system typically further comprises at least one display device 546 operably connected to display at least one of the different selected wavelength region images from the different imaging devices. The different imaging devices can, for example, comprise different regions of a single imaging detector or the different imaging devices can comprise physically separate imaging detectors.

Figure 26:
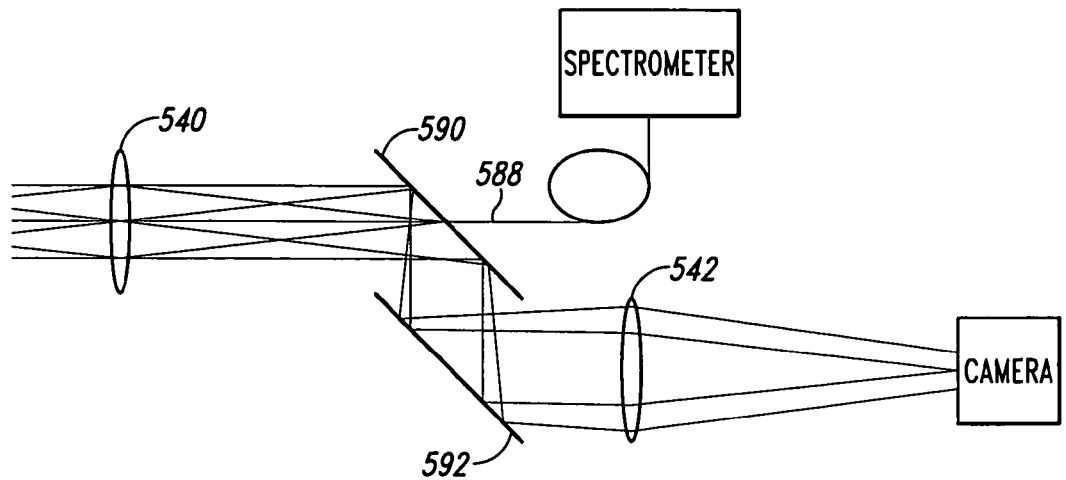
FIG. 26 is a schematic representation of an alternative embodiment of the system shown in FIG. 2.
Figure 27A:
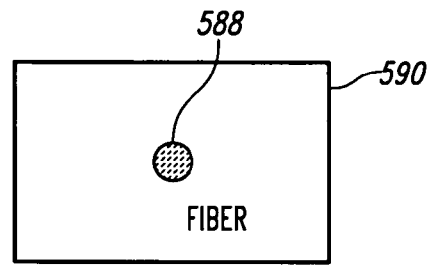
FIG. 27 is a schematic representation of a portion of the system set forth in FIG. 26.
Figure 27B:
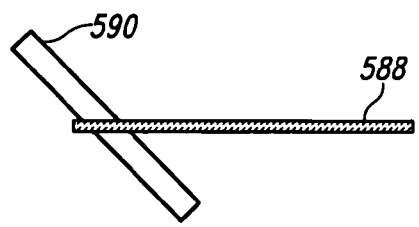

FIGS. 26–27b show another alternative configuration. Mirror 590 can be a full reflection mirror with a pre-drilled hole to hold an optical fiber 588 or other suitable optical light guide for spectral measurement sampling. Optical fiber 288 and mirror 590 are also depicted in FIGS. 27a–27b. Light collected by the fiber is sent to a spectrometer or other suitable spectral device for spectral analysis. Mirror 590 is located at about the image plane after lens 540 and the flat cut end of the fiber is always in focus to collect light signal from a defined area of the image for spectral analysis. Mirror 592 is placed in parallel to mirror 590 to bend the light beam back to its original direction and then through lens 542 to camera for image acquisition. Alternatively, Mirror 592 could be omitted and lens 542 and the camera will be located at an angle 90 degrees from the original light path (or in any other desired direction).

To get an image without the alignment black spot, and if desired no spectral measurement, mirror 590 will be moved along the surface plane of the mirror so that the end of optical fiber 588 is located outside of the light beam. Alternatively, the two mirrors could be coupled together and moved together in a direction which is not inside or parallel to the surface plane of the mirror, for example, along the light path, or perpendicular to the light path so that the fiber end is outside of the light beam. In both cases, a constant optical path length is kept when moving the mirror or the mirrors.

The two mirrors shown in FIG. 26 are at an angle of 45 degrees to the income light beam for illustration purposes only. They can be at any other desired angle. An angle closer to 90 degrees can be preferred because the end face of optical fiber 588 may then be maintained closer to parallel to the mirror surface.

In some embodiments of the present invention, such as those in FIGS. 20, 21, 22, and 26, it is possible that any dust or dirt on the surface of the mirrors therein will show up clearly in the final camera image if beam separator 506 or mirror 590 is located at an image plane. This can be solved in at least three ways. One way, as depicted in FIG. 27b, is to position the end of optical fiber 588 slightly outside of the mirror, preferably while keeping the length of the total optical path the same. This allows one to keep the end of optical fiber 588 at the focused image plane while maintaining mirror 590 slightly outside the image plane, which means that dust or dirt will not be imaged onto the camera.

A second approach is to couple the mirrors 590, 592 together and the move them together (along with the end of optical fiber 588, which would be coplanar with mirror 590) out of the focused image plane. However, in this approach, it is preferred to move mirror 590 back to the image plane when doing spectral measurement, which also would re-situate the mirrors such that any dust or dirt will be seen on the camera image.

A third approach is to put a cover glass on top of mirror 590 or beam separator 506. This way any dust or dirt will fall on the surface of the glass cover, not on mirror 590 or beam separator 506, which are at the image plane. Therefore, the dust and dirt on the cover glass, which are not at the image plane, will not be imaged onto the camera.

The present invention also provides methods of making or using the devices disclosed herein. In certain embodiments such methods comprise detecting a light beam. The methods comprise separating via (by use of) beam separator a small portion of light beam from a remainder of light beam to provide separated light beam and remainder light beam. The separated light beam is transmitted to spectroscopy device optically connected to beam separator, and remainder light beam is transmitted to an imaging device optically connected to receive remainder light beam and to provide an image therefrom. The methods can further comprise displaying on a display device a spectrum from spectroscopy device and the image from imaging device.

In some embodiments of the methods, spectroscopy device is located outside of light beam and beam separator comprises light redirection device sized and located to intercept a small area of light beam and change the direction of such small area toward spectroscopy device (or vice-versa where the light redirection device directs the light to the imaging device). The method can further comprise imparting via light redirection device a small residual image in remainder light beam corresponding to the location of light redirection device in light beam. The small residual image can be imparted substantially in the center of light beam. The methods can also comprise separating via light redirection device substantially all light incident on light redirection device from remainder light beam.

The beam separator can be a beam splitter that intercepts a large portion of light beam such that the beam splitter does not leave a significant residual image in remainder light beam, and the methods further comprise transmitting through the beam splitter substantially more than 50%, up to 80%, 90% or 99% or more, of the electromagnetic radiation in light beam to imaging device and reflecting via the beam splitter substantially less than 50% of the electromagnetic radiation in light beam to spectroscopy device.

The methods can be implemented via a pixelated detector or a non-pixelated detector. Beam separator can be located in substantially a same image plane as imaging device, substantially in front of and either not touching or abutting imaging device, or substantially behind imaging device and either not touching or abutting imaging device. The method can further comprise passing light beam through a first focusing element in front of beam separator and a second focusing element between beam separator and imaging device such that the first focusing element provides a first conjugate image plane substantially at beam separator and the second focusing element located to provides a second conjugate image plane substantially at imaging device.

The methods can comprise contemporaneously or sequentially displaying both the image(s) from imaging device and the spectrum(spectra) from spectroscopy device on a single display device. The methods can also comprise passing light beam through an image separator and separating the image into a plurality of wavelength region images corresponding to an equivalent plurality of different wavelength regions of light beam, and then displaying the wavelength region images on the display device. Such separating can comprise passing light beam through a plurality of imaging beam splitters each of which selects for different selected wavelength regions and directs the selected different wavelength regions to different imaging devices. The plurality of different imaging beam splitters can be disposed linearly or radially or otherwise as desired along light beam. The methods can further comprise selecting for all but one desired, non-selected different wavelength region and then transmitting the one desired, non-selected different wavelength region to imaging device.

The different wavelength regions can be selected to comprise at least two of UV to blue light, visible light, near-infrared light and infrared light, or other desired wavelength ranges.

The methods can be implemented, for example, via a controller operably connected to imaging device and/or spectroscopy device and containing computer-implemented programming that controls imaging device and spectroscopy device. The method can also be implemented, for example, via an endoscope, microscope, telescope or camera.

The present invention also provides methods of providing a plurality of images derived from different wavelength regions of an initial image. In certain embodiments, the methods comprise passing a light beam carrying the initial image along a light beam path in an image separator comprising a plurality of imaging beam splitters disposed in the light beam path, then selecting different selected wavelength regions of the initial image via the imaging beam splitters to provide selected wavelength region images. The selected wavelength region images are then directed to different imaging devices. The methods can further comprise selectively displaying one or more of the selected wavelength region images, along with other images or information (such as a spectrum) on a display device.

The imaging beam splitters, as well as corresponding detectors, if desired, can be disposed linearly or radially along the light beam path. For example, the imaging beam splitters can be disposed alternatingly such that a first sub-set of the imaging beam splitters direct a first set of selected different wavelength regions in a first direction and a second sub-set of the imaging beam splitters direct a second set of selected different wavelength regions in a second direction, which can be substantially 180° away from the first direction. There can also be an imaging device located in the light beam and behind the imaging beam splitters to directly receive the non-selected wavelength region image. The different wavelength regions can comprise any variety of desired of wavelength regions, as discussed elsewhere herein.

The present invention includes the various elements, systems, methods, etc., herein in means-plus-function and step-plus-function format.

Referring back to FIG. 2, although the beam-directing device 52 has been described as being movable, by virtue of the motion mechanism 61, alternatively, the beam-directing device 52 may be permanently fixed within the housing 62. As a further alternative, the beam-directing device 52 is not essential to at least some aspects or embodiments of the present invention, and in any such embodiments the beam-directing device may be omitted if desired. In either case, the CCD camera 50 may be constructed without any moving parts if desired, which tends to reduce the weight of the camera. Or, if desired, rather than providing a motion mechanism 61, the beam-directing device may be manually moved into and out of the optical path of the electromagnetic radiation beam 58 by a user of the first measuring device 44.

With respect to spectroscopy measurements, in addition to merely displaying the fluorescence and reflectance spectra on the monitor 45, additionally the processor circuit 41 may be programmed with algorithms to analyze the spectra and to suggest or diagnose particular disease types in response to the spectra. Such algorithms are preferably based on spectral studies of a statistically large number of patients.

Figure 18:
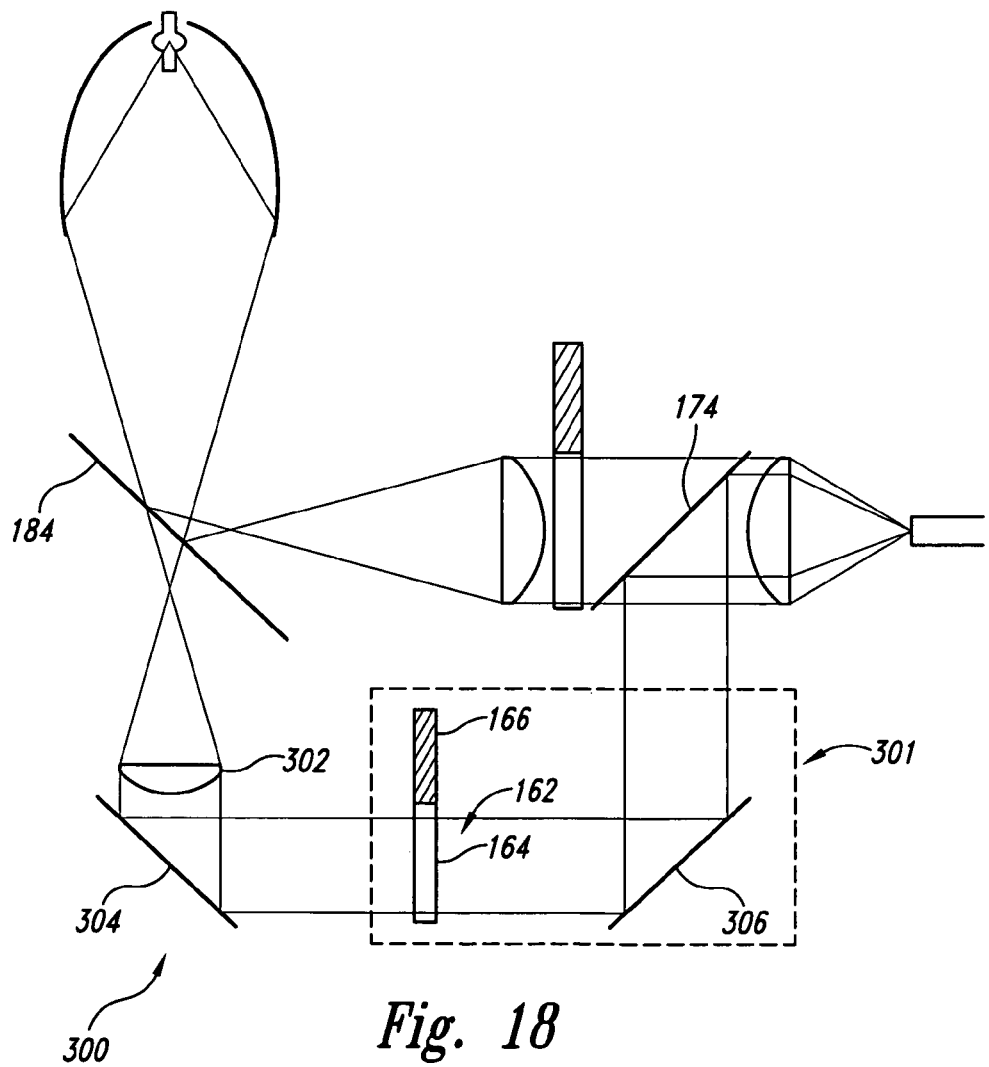
FIG. 18 is a schematic representation of an apparatus for producing illuminating radiation for fluorescence and reflectance imaging, according to a fifth embodiment of the invention.
Figure 19:
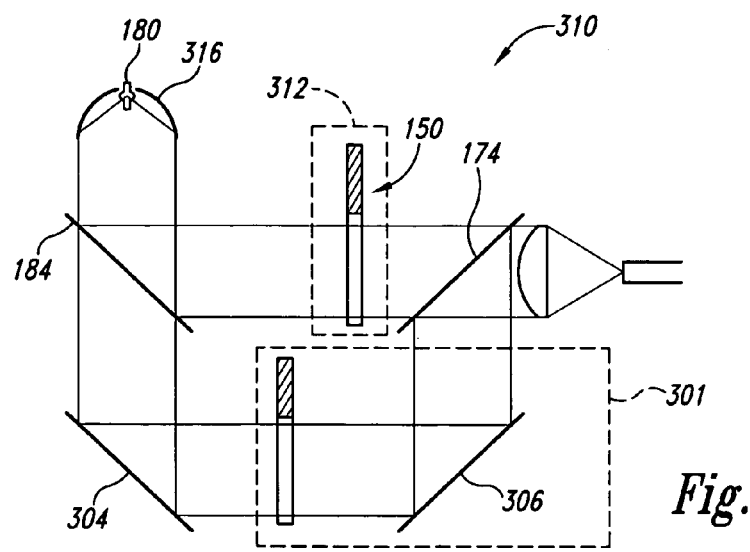
FIG. 19 is a schematic representation of an apparatus for producing illuminating radiation for fluorescence and reflectance imaging, according to a sixth embodiment of the invention.

Referring to FIGS. 9, 18 and 19, the apparatus 130 shown in FIG. 9 is merely one example of an apparatus for producing illuminating radiation for fluorescence and reflectance imaging. Alternatively, other types of apparatus 130, or other types of optical systems 132, may be substituted.

For example, in one alternative embodiment, a modified redirecting device 188 includes a liquid light guide rather than an optical fiber bundle.

Referring to FIG. 18, in a further alternative embodiment, a modified redirecting device 300 includes a lens 302 and a first reflector 304, and a modified second optical subsystem 301 includes the filtering device 162 as described above in connection with FIG. 9, and a second reflector 306. Input radiation received from the beam splitter 184 is collimated by lens 302 and is directed onto the first reflector 304, from which it is reflected through the filtering device 162 to the second reflector 306, which reflects any such radiation to the dichroic reflecting device 174.

Similarly, referring to FIGS. 9, 18 and 19, an alternative apparatus for producing illuminating radiation for fluorescence and reflectance imaging is shown generally at 310 in FIG. 19. The apparatus 310 includes an alternative first optical subsystem 312 which is similar to the first optical subsystem 134 shown in FIG. 9 but which omits the lens 190. The apparatus further includes a modified redirecting device which is similar to that shown at 300 in FIG. 18 but which omits the lens 302. The apparatus 310 also includes the modified second optical subsystem 301 shown in FIG. 18. The elliptical reflector 182 of the electromagnetic radiation source 148 is replaced with a parabolic reflector 316, at the focal point of which the lamp 180 is positioned. The electromagnetic radiation source 148 thus directs parallel rays of electromagnetic radiation to the beam splitter 184, which provides input radiation to the first and second optical subsystems as described above.

Figure 25:
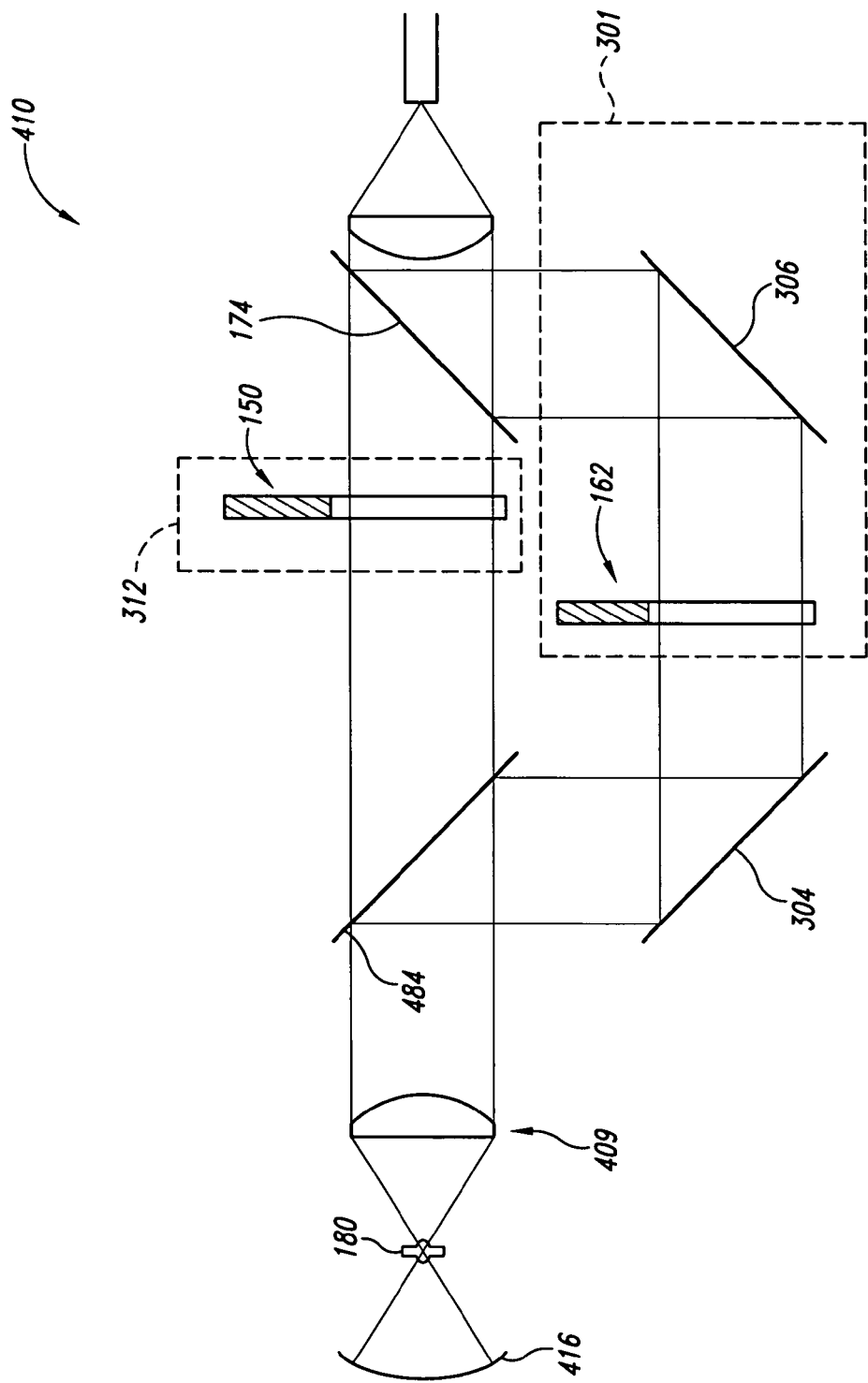
FIG. 25 is a schematic representation of an apparatus for producing illuminating radiation for fluorescence and reflectance imaging, according to another embodiment of the invention.

Similarly, referring to FIGS. 19, and 25, an alternative apparatus for producing illuminating radiation for fluorescence and reflectance imaging is shown generally at 410 in FIG. 19. The apparatus 410 includes a first optical subsystem 312, a second optical subsystem 301, a beam combiner 174, and a beam redirecting 304, which are all identical to what shown in FIG. 19. The parabolic reflector 316 of the electromagnetic radiation source 148 is replaced with a spherical reflector 416, at the focal point of which the lamp 180 is positioned. Both the reflected rays by reflector 416 and the rays that come from the lamp 180 directly are collected and collimated by condenser lens 409 and are then directed to beam splitter 484. The beam splitter 484 is a hot mirror, which transmits visible and blue light to the first optical subsystem and reflects NIR light to the second optical subsystem.

As a further example, referring back to FIG. 9, the beam splitter 184 may alternatively include a hot mirror rather than a cold mirror. The hot mirror reflects near infrared radiation but transmits visible light. In such a case, the functions of the first and second optical subsystems may be interchanged. Thus, in such an embodiment, the beam splitter 184 reflects the NIR component for receipt by the first optical subsystem. The redirecting device 188 redirects the excitation and white light illumination components for receipt by the second optical subsystem. The filtering device 150 of the first optical subsystem is substituted for the filtering device 162 of the second optical subsystem, and vice versa. These and other such variations will be apparent to one of ordinary skill in the art upon reviewing this specification and are not considered to depart from the scope of the present invention as construed in accordance with the accompanying claims.

In addition, referring back to FIGS. 2, 4, 5 and 12, alternative ways of normalizing a fluorescence image to compensate for geometrical factors may be substituted. For example, block 212 may be modified to cause the fluorescence signals produced by the second detector 87 in response to fluorescence of the tissue at wavelengths between 500 and 600 nm to be provided to a first color channel input of a multicolor display device, or more particularly, the green channel input 215 of the RGB color frame grabber 47. Similarly, block 212 may be modified to cause first NIR reflectance signals produced by the third detector 88 in response to NIR reflectance of the tissue in the first NIR wavelength range 116 (750 to 800 nm) to be provided to the red channel input 217 of the RGB color frame grabber, and to cause second NIR reflectance signals produced by the fourth detector 89 in response to NIR reflectance of the tissue in the second NIR wavelength range 118 (800 to 900 nm) to be provided to the blue channel input 219 of the RGB color frame grabber. The resulting three-channel normalized fluorescence image is brighter than the two-channel image described in connection with block 212. In such a three-channel normalized fluorescence image, normal tissue tends to appear as a green background, while the abnormal or diseased tissue appears as a bright magenta color. Alternatively, the signals of the third and fourth detectors may be interchanged among the blue and red channel inputs.

As a further alternative, block 212 may be modified to direct the processor circuit 41 to numerically normalize the green fluorescence image. More particularly, referring back to FIG. 12, in an alternative embodiment of the invention block 212 is modified to direct the processor circuit to produce ratio signals such that for each point in the tissue, a strength of the ratio signal corresponding to the point is proportional to a ratio of an intensity of reflectance of the point in a first near infrared (NIR) wavelength band to an intensity of fluorescence of the point. Modified block 212 further directs the processor circuit to cause the ratio signals to be provided to an input of a display device to produce the fluorescence image of the tissue. For example, this may be achieved by producing a normalized monochromatic image in which the brightness of each individual pixel in the image corresponding to each respective point in the tissue is proportional to the ratio of the signal of the fourth detector 89 (or alternatively the third detector 88) produced in response to the NIR component 218 reflected by that point, to the signal of the fluorescence component 214 emitted by that point. It will be appreciated that this ratio will be higher for diseased or abnormal tissues than for normal tissues and therefore, diseased tissues will appear as bright spots on a dark background representing normal tissue.

Or, referring back to FIG. 12, in a further alternative embodiment of the invention, block 212 is modified to direct the processor circuit to cause the ratio signals to be provided to a first color channel input of a multicolor display device, which in this embodiment is the blue channel input 219 of the RGB color frame grabber 47 to produce a blue image of the tissue, while simultaneously, fluorescence signals produced by the second detector 87 in response to fluorescence of the tissue are provided to the green channel input 215 to produce a green image of the tissue, and the NIR reflectance signals produced by the fourth detector 89 (or alternatively the third detector 88) are provided to the red channel input 217 to produce a red image of the tissue on the monitor 51. In the resulting normalized fluorescence image, normal tissue tends to appear as a brighter cyanic-green background, while the abnormal or diseased tissue appears as a bright magenta color.

Similarly, referring to FIGS. 2, 4, 5 and 12, other ways of producing a normalized NIR reflectance image of the tissue, indicative of its oxygenation status, may be substituted. For example, a modified block 213 directs the processor circuit to numerically normalize the NIR reflectance image 235 by, for each point in the tissue, causing a corresponding pixel of a multi-pixel display device to be illuminated with a brightness proportional to a ratio of a strength of a first signal corresponding to the point to a strength of a second signal corresponding to the point. More particularly, a digital image may be produced in which the brightness of each individual pixel in the image corresponding to each respective point in the tissue is proportional to the ratio of the strength of the signal produced by the fourth detector 89 in response to the NIR reflectance of the tissue in the second NIR wavelength band 118, to the strength of the signal produced by the third detector 88 in response to the NIR reflectance of the tissue in the first NIR wavelength band 116. It will be appreciated that this ratio will be higher for diseased or abnormal tissues than for normal tissues, and thus, in the resulting digital image, diseased tissues will appear as bright areas against a dark background of normal tissues.

As a further example, an alternative modified block 213 directs the processor circuit to produce the oxygenation image by producing third signals or ratio signals in the above manner, and causing the third signals to be provided to a third color channel input of the display device. More particularly, the further-modified block 213 directs the processor circuit to cause a signal as described above, produced in response to the ratio of NIR reflectance in the second NIR wavelength band 118 to that in the first NIR wavelength band 116, to be provided to the blue channel input 219 to produce a blue image of the tissue, while simultaneously, the signal produced by the third detector 88 may be used to produce a green image of the tissue and the signal produced by the fourth detector 89 may be used to produce a red image of the tissue on the monitor 51. In the resulting normalized NIR reflectance image, normal tissue tends to appear as a brighter cyanic-green background, while the abnormal or diseased tissue appears as a bright magenta color.

Also, referring back to FIGS. 2 and 12, although blocks 212 and 213 have been described as alternately displaying the normalized fluorescence image 234 and the normalized NIR reflectance image 235 respectively on the monitor 51, alternatively, these images may be simultaneously displayed, as the physical measurements required to produce the images 234 and 235 are performed simultaneously in the main embodiment described above. Therefore, in an alternative embodiment, an additional monitor (not shown) is provided, along with an additional RGB color frame grabber (not shown). A modified block 212 is executed to cause the normalized fluorescence image 234 to be displayed on the monitor 51 as described above in connection with block 212, and to simultaneously control the camera controlling electronics 49 and the additional RGB color frame grabber to cause the normalized NIR reflectance image 235 to be displayed on the additional monitor, as described above in connection with block 213. Thus, the operator of the endoscope 59 may simultaneously observe the fluorescence/NIR reflectance spectral distribution image 220 on the monitor 45, the normalized fluorescence image 234 on the monitor 51, and the normalized NIR reflectance image 235 on the additional monitor, for improved diagnostic capability.

More generally, while specific embodiments of the invention have been described and illustrated throughout this specification, such embodiments should be considered illustrative of the invention only and not as limiting the scope of the invention as construed in accordance with the accompanying claims.

What is claimed is:

1. A system means for detecting a light beam comprising:
an area means for receiving the light beam;
a means for spatially separating the light beam disposed in the area means to separate a small spatial portion of the light beam from an adjacent remainder of the light beam to provide a separated light beam and a remainder light beam and means to transmit the separated light beam to a means for spectroscopy;
a means for imaging disposed in the area means to operably receive the remainder light beam to provide an image therefrom; and,
a means for spectroscopy optically connected to the means for separating the light beam to receive the separated light beam to provide a spectrum therefrom, wherein the means for spectroscopy is located outside of the light beam and the means for spatially separating the light beam comprises a means for light redirection sized and located to intercept a small area of the light beam and change the direction of such small area toward the means for spectroscopy, and wherein the means for light redirection separates substantially all light incident thereon from the remainder light beam and imparts a small residual image in the remainder light beam corresponding to the location of the means for light redirection in the light beam.

2. A system means for detecting a light beam comprising:
an area means for receiving the light beam;
a means for spatially separating the light beam disposed in the area means to separate a small spatial portion of the light beam from a an adjacent remainder of the light beam to provide a separated light beam and a remainder light beam and means to transmit the separated light beam to a means for spectroscopy;
a means for imaging disposed in the area means to operably receive the remainder light beam to provide an image therefrom; and,
a means for spectroscopy optically connected to the means for separating the light beam to receive the separated light beam to provide a spectrum therefrom, wherein the means for spatially separating the light beam is a means for splitting the light beam that transmits at least about 80% of the light beam and reflects at least about 20% of the light beam.

3. The means for detecting a light beam of claim 1 or 2 wherein the means for detecting a light beam further comprises a means for displaying operably connected to the means for imaging to display an image from the means for imaging.

4. The means for detecting a light beam of claim 1 or 2 wherein the system further comprises a means for displaying operably connected to the means for spectroscopy to display a spectrum from the means for spectroscopy.

5. The means for detecting a light beam of claim 1 or 2 wherein the system further comprises a means for image separating comprising a plurality of means for selecting light that separates the image into a plurality of selected wavelength region images wherein each selected wavelength region image corresponds to a different wavelength region of the range of wavelengths in the light beam.

6. The means for detecting a light beam of claim 1 or 2 wherein the means for detecting comprises a means for controlling operably connected to an imaging detector and the means for spectroscopy and containing computer-implemented programming that controls the means for imaging and the means for spectroscopy.

* * * * *